United States Patent
Goodman et al.

(10) Patent No.: US 7,153,936 B2
(45) Date of Patent: *Dec. 26, 2006

(54) SEMAPHORIN GENE FAMILY

(75) Inventors: Corey S. Goodman, Berkeley, CA (US); Alex L. Kolodkin, Berkeley, CA (US); David Matthes, Berkeley, CA (US); David R. Bentley, Berkeley, CA (US); Timothy O'Connor, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 806 days.

This patent is subject to a terminal disclaimer.

(21) Appl. No.: 10/067,632

(22) Filed: Feb. 4, 2002

(65) Prior Publication Data

US 2003/0166849 A1  Sep. 4, 2003

Related U.S. Application Data

(60) Continuation of application No. 09/060,610, filed on Apr. 15, 1998, now Pat. No. 6,344,544, which is a continuation of application No. 08/835,268, filed on Apr. 8, 1997, now Pat. No. 5,807,826, which is a division of application No. 08/121,713, filed on Sep. 13, 1993, now Pat. No. 5,639,856.

(51) Int. Cl.
 *C07K 1/00* (2006.01)
 *C07K 14/00* (2006.01)
 *A61K 38/00* (2006.01)

(52) U.S. Cl. ............ 530/350; 530/399; 435/69.1; 435/70.1

(58) Field of Classification Search ............ None
 See application file for complete search history.

(56) References Cited

U.S. PATENT DOCUMENTS

| | | | |
|---|---|---|---|
| 5,416,197 A | | 5/1995 | Raper et al. |
| 5,639,856 A | * | 6/1997 | Goodman et al. .......... 530/326 |
| 5,807,826 A | | 9/1998 | Goodman et al. |
| 6,013,781 A | * | 1/2000 | Goodman et al. ......... 536/23.1 |

FOREIGN PATENT DOCUMENTS

WO  93/00365  1/1993

OTHER PUBLICATIONS

Waterson et al., Nature Genetics 1(2): 114-23, May 1992.
Kolodkin et al. Neuron, 9:831-45, 1992.
Genbank Accession No. Mg1187.
Genbank Accession No. X57318.
Genbank Accession No. M35707.
Genbank Accession No. X62984 (Harbitz et al).
Hames et al, Nucleic acid hybridisation, a practical approach, published 1985 by IRL Press (Oxford) pp. 81, 82, 93-95.
Aguado et al, J. Gen. Virol., vol. 73, issued Nov. 1992, pp. 2887-2902.
Smith et al, J. Gen. Virol., vol. 72, issued 1991, pp. 1349-1376.
Goodman and Shatz, "Developmental Mechanisms that Generate Precise Patterns of Neuronal Connectivity", Cell, vol. 72/Neuron, vol. 10 (Suppl.), 77-98 (1993).
Raper, "Repulsive Cues in Axonal Guidance", an abstract presented at the GIBCO-BRL Symposium on Genes and Development/Function of Brain on Jul. 26, 1993.
Luo et al., Cell, 75:217-227 (1993).
Raper and Kapfhammer, Neuron, 2:21-29 (1990).
Schnell and Schwab, Nature, 343:269-272 (1990).
Schwab and Caroni, J. Neuroscience, 8(7):2381-2393 (1988).
Kolodkin et al., Cell, vol. 75 (1993) 1389-1399.
Jessell et al., Principles of Neural Science (3rd edition)(1991) chapter 18.
Saneto et al., Neuro chemistry (Chap. 2) (1987) pp. 27-63.
Patel, Biochem. Soc. Trans. (1989) 17(5) 931.
McMartin, Biochem. Soc. Trans (1989) 17(5) pp. 931-934.
Bundgaard et al., Biochem. Soc. Trans., (1989) 17(5) pp. 947-949.

* cited by examiner

*Primary Examiner*—Janet L. Andres
*Assistant Examiner*—Chang-Yu Wang
(74) *Attorney, Agent, or Firm*—Townsend and Townsend and Crew LLP

(57) ABSTRACT

A novel class of proteins, semaphorins, nucleic acids encoding semaphorins, semaphorin peptides, and methods of using semaphorins and semaphorin-encoding nucleic acids are disclosed. Semaphorin peptides and receptor agonists and antagonists provide potent modulators of nerve cell growth and regeneration. The invention provides pharmaceutical compositions, methods for screening chemical libraries for regulators of cell growth/differentiation; semaphorin gene-derived nucleic acids for use in genetic mapping, as probes for related genes, and as diagnostic reagents for genetic neurological disease; specific cellular and animal systems for the development of neurological disease therapy.

1 Claim, No Drawings

SEMAPHORIN GENE FAMILY

This application is a continuation of U.S. application Ser. No. 09/060,610, filed Apr. 15, 1998 now U.S. Pat. No. 6,344,544, which is a continuation of U.S. application Ser. No. 08/835,268, filed Apr. 8, 1997, now U.S. Pat. No. 5,807,826, which is a division of U.S. application Ser. No. 08/121,713, filed Sep. 13, 1993, now U.S. Pat. No. 5,639,856.

The research carried out in the subject application was supported in part by grants from the National Institutes of Health. The government may have rights in any patent issuing on this application.

INTRODUCTION

1. Technical Field

The technical field of this invention concerns peptides, polypeptides, and polynucleotides involved in nerve cell growth.

2. Background

The specificity of the wiring of the nervous system—the complex pattern of specific synaptic connections—begins to unfold during development as the growing tips of neurons—the growth cones—traverse long distances to find their correct targets. Along their journey, they are confronted by and correctly navigate a series of choice points in a remarkably unerring way to ultimately contact and recognize their correct target.

The identification of growth cone guidance cues is to a large extent, the holy grail of neurobiology. These are the compounds that tell neurons when to grow, where to grow, and when to stop growing. The medical applications of such compounds and their antagonists are enormous and include modulating neuronal growth regenerative capacity, treating neurodegenerative disease, and mapping (e.g. diagnosing) genetic neurological defects.

Over decades of concentrated research, various hypotheses of chemo-attractants and repellant, labeled pathways, cell adhesion molecules, etc. have been evoked to explain guidance. Recently, several recent lines of experiments suggest repulsion may play an important role in neuron guidance and two apparently unrelated factors ("Neurite Growth Inhibitor" and "Collapsin") capable of inhibiting or collapsing growth cones have been reported.

Relevant Literature

For a recent review of much of the literature in this field, see Goodman and Shatz (1993) Cell 72/Neuron 10, 77–98. A description of grasshopper fasciclin IV (now called G-Semaphorin I) appears in Kolodkin et al. (1992) Neuron 9, 831–845. Recent reports on Collapsin and Neurite Growth Inhibitor include Raper and Kapfhammer (1990) Neuron 4, 21–29, an abstract presented by Raper at the GIBCO-BRL Symposium on "Genes and Development/Function of Brain" on Jul. 26, 1993 and Schwab and Caroni (1988) J Neurosci 8, 2381 and Schnell and Schwab (1990) Nature 343, 269, respectively.

SUMMARY OF THE INVENTION

A novel class of proteins, semaphorins, nucleic acids encoding semaphorins, and methods of using semaphorins and semaphorin-encoding nucleic acids are disclosed. Semaphorins include the first known family of human proteins which function as growth cone inhibitors and a family of proteins involved in viral, particularly pox viral, pathogenesis and oncogenesis. Families of semaphorin-specific receptors, including receptors found on nerve growth cones and immune cells are also disclosed.

The invention provides agents, including semaphorin peptides, which specifically bind semaphorin receptors and agents, including semaphorin receptor peptides, which specifically bind semaphorins. These agents provide potent modulators of nerve cell growth, immune responsiveness and viral pathogenesis and find use in the treatment and diagnosis of neurological disease and neuro-regeneration, immune modulation including hypersensitivity and graft-rejection, and diagnosis and treatment of viral and oncological infection/diseases.

Semaphorins, semaphorin receptors, semaphorin-encoding nucleic acids, and unique portions thereof also find use variously in screening chemical libraries for regulators of semaphorin or semaphorin receptor-mediated cell activity, in genetic mapping, as probes for related genes, as diagnostic reagents for genetic neurological, immunological and oncological disease and in the production of specific cellular and animal systems for the development of neurological, immunological, oncological and viral disease therapy.

DESCRIPTION OF SPECIFIC EMBODIMENTS

The present invention discloses novel families of proteins important in nerve and immune cell function: the semaphorins and the semaphorin receptors. The invention provides agents, including semaphorin peptides, which specifically bind semaphorin receptors and agents, including semaphorin receptor peptides, which specifically bind semaphorins. These agents find a wide variety of clinical, therapeutic and research uses, especially agents which modulate nerve and/or immune cell function by specifically mimicing or interfering with semaphorin-receptor binding. For example, selected semaphorin peptides shown to act as semaphorin receptor antagonists are effective by competitively inhibiting native semaphorin association with cellular receptors. Thus, depending on the targeted receptor, these agents can be used to block semaphorin mediated neural cell growth cone repulsion or contact inhibition. Such agents find broad clinical application where nerve cell growth is indicated, e.g. traumatic injury to nerve cells, neurodegenerative disease, etc. A wide variety of semaphorin- and semaphorin receptor-specific binding agents and methods for identifying, making and using the same are described below.

Binding agents of particular interest are semaphorin peptides which specifically bind and antagonize a semaphorin receptor and semaphorin receptor peptides which specifically bind a semaphorin and prevent binding to a native receptor. While exemplified primarily with semaphorin peptides, much of the following description applies analogously to semaphorin receptor peptides.

The semaphorin peptides of the invention comprise a unique portion of a semaphorin and have semaphorin binding specificity. A "unique portion" of a semaphorin has an amino acid sequence unique to that disclosed in that it is not found in any previously known protein. Thus a unique portion has an amino acid sequence length at least long enough to define a novel peptide. Unique semaphorin portions are found to vary from about 5 to about 25 residues, preferably from 5 to 10 residues in length, depending on the particular amino acid sequence. Unique semaphorin portions are readily identified by comparing the subject semaphorin portion sequences with known peptide/protein sequence data bases. Preferred unique portions derive from the semaphorin domains (which exclude the Ig-like, intracellular and transmembrane domains as well as the signal sequences) of the disclosed semaphorin sequences, especially regions that bind the semaphorin receptor, especially that of the human varieties. Preferred semaphorin receptor unique portions derive from the semaphorin binding domains, especially regions with residues which contact the semaphorin ligand, especially that of the human varieties. Particular preferred peptides are further described herein.

The subject peptides may be free or coupled to other atoms or molecules. Frequently the peptides are present as a portion of a larger polypeptide comprising the subject peptide where the remainder of the polypeptide need not be semaphorin- or semaphorin receptor-derived. Alternatively, the subject peptide may be present as a portion of a "substantially full-length" semaphorin domain or semaphorin receptor sequence which comprises or encodes at least about 200, preferably at least about 250, more preferably at least about 300 amino acids of a disclosed semaphorin/receptor sequence. Thus the invention also provides polypeptides comprising a sequence substantially similar to that of a substantially full-length semaphorin domain or a semaphorin receptor. "Substantially similar" sequences share at least about 40%, more preferably at least about 60%, and most preferably at least about 80% sequence identity. Where the sequences diverge, the differences are generally point insertions/deletions or conservative substitutions, i.e. a cysteine/threonine or serine substitution, an acidic/acidic or hydrophobic/hydrophobic amino acid substitution, etc.

The subject semaphorin peptides/polypeptides are "isolated", meaning unaccompanied by at least some of the material with which they are associated in their natural state. Generally, an isolated peptide/polypeptide constitutes at least about 1%, preferably at least about 10%, and more preferably at least about 50% by weight of the total peptide/protein in a given sample. By pure peptide/polypeptide is intended at least about 90%, preferably at least 95%, and more preferably at least about 99% by weight of total peptide/protein. Included in the subject peptide/polypeptide weight are any atoms, molecules, groups, or polymers covalently coupled to the subject semaphorin/receptor peptide/polypeptide, especially peptides, proteins, detectable labels, glycosylations, phosphorylations, etc.

The subject peptides/polypeptides may be isolated or purified in a variety of ways known to those skilled in the art depending on what other components are present in the sample and to what, if anything, the peptide/polypeptide is covalently linked. Purification methods include electrophoretic, molecular, immunological and chromatographic techniques, especially affinity chromatography and RP-HPLC in the case peptides. For general guidance in suitable purification techniques, see Scopes, R., Protein Purification, Springer-Verlag, NY (1982).

The subject peptides/polypeptides generally comprise naturally occurring amino acids but D-amino acids or amino acid mimetics coupled by peptide bonds or peptide bond mimetics may also be used. Amino acid mimetics are other than naturally occurring amino acids that conformationally mimic the amino acid for the purpose of the requisite semaphorin/receptor binding specificity. Suitable mimetics are known to those of ordinary skill in the art and include β-γ-δ amino and imino acids, cyclohexylalanine, adamantylacetic acid, etc., modifications of the amide nitrogen, the α-carbon, amide carbonyl, backbone modifications, etc. See, generally, Morgan and Gainor (1989) Ann. Repts. Med. Chem 24, 243–252; Spatola (1983) Chemistry and Biochemistry of Amino Acids, Peptides and Proteins, Vol VII (Weinstein) and Cho et. al (1993) Science 261, 1303–1305 for the synthesis and screening of oligocarbamates.

The subject semaphorin peptides/polypeptides have a "semaphorin binding specificity" meaning that the subject peptide/polypeptide retains a molecular conformation specific to one or more of the disclosed semaphorins and specifically recognizable by a semaphorin-specific receptor, antibody, etc. As such, a semaphorin binding specificity may be provided by a semaphorin-specific immunological epitope, lectin binding site, etc., and preferably, a receptor binding site. Analogously, the semaphorin receptor peptides/polypeptides have a "semaphorin receptor binding specificity" meaning that these peptides/polypeptides retain a molecular conformation specific to one or more of the disclosed semaphorin receptors and specifically recognizable by a semaphorin, a receptor-specific antibody, etc.

"Specific binding" is empirically determined by contacting, for example a semaphorin-derived peptide with a mixture of components and identifying those components that preferentially bind the semaphorin. Specific binding is most conveniently shown by competition with labeled ligand using recombinant semaphorin peptide either in vitro or in cellular expression systems as disclosed herein. Generally, specific binding of the subject semaphorin has binding affinity of $10^{-6}$M, preferably $10^{-8}$M, more preferably $10^{-10}$M, under in vitro conditions as exemplified below.

The peptides/polypeptides may be modified or joined to other compounds using physical, chemical, and molecular techniques disclosed or cited herein or otherwise known to those skilled in the relevant art to affect their semaphorin binding specificity or other properties such as solubility, membrane transportability, stability, binding specificity and affinity, chemical reactivity, toxicity, bioavailability, localization, detectability, in vivo half-life, etc. as assayed by methods disclosed herein or otherwise known to those of ordinary skill in the art. For example, point mutations are introduced by site directed mutagenesis of nucleotides in the DNA encoding the disclosed semaphorin polypeptides or in the course of in vitro peptide synthesis.

Other modifications to further modulate binding specificity/affinity include chemical/enzymatic intervention (e.g. fatty acid-acylation, proteolysis, glycosylation) and especially where the peptide/polypeptide is integrated into a larger polypeptide, selection of a particular expression host, etc. In particular, many of the disclosed semaphorin peptides contain serine and threonine residues which are phosphorylated or dephosphorylated. See e.g. methods disclosed in Roberts et al. (1991) Science 253, 1022–1026 and in Wegner et al. (1992) Science 256, 370–373. Amino and/or carboxyl termini may be functionalized e.g., for the amino group, acylation or alkylation, and for the carboxyl group, esterification or amidification, or the like. Many of the disclosed semaphorin peptides/polypeptides also contain glycosylation sites and patterns which may disrupted or modified, e.g. by enzymes like glycosidases or used to purify/identify the receptor, e.g. with lectins. For instance, N or O-linked glycosylation sites of the disclosed semaphorin peptides may be deleted or substituted for by another basic amino acid such as Lys or His for N-linked glycosylation alterations, or deletions or polar substitutions are introduced at Ser and Thr residues for modulating O-linked glycosylation. Glycosylation variants are also produced by selecting appropriate host cells, e.g. yeast, insect, or various mammalian cells, or by in vitro methods such as neuraminidase digestion. Useful expression systems include COS-7, 293, BHK, CHO, TM4, CV1, VERO-76, HELA, MDCK, BRL 3A, W138, Hep G2, MMT 060562, TRI cells, baculovirus systems, for examples. Other covalent modifications of the disclosed semaphorin peptides/polypeptides may be introduced by reacting the targeted amino acid residues with an organic derivatizing (e.g. methyl-3-[(p-azido-phenyl)dithio] propioimidate) or crosslinking agent (e.g. 1,1-bis(diazoacetyl)-2-phenylethane) capable of reacting with selected side chains or termini. For therapeutic and diagnostic localization, semaphorins and peptides thereof may be labeled directly (radioisotopes, fluorescers, etc.) or indirectly with an agent capable of providing a detectable signal, for example, a heart muscle kinase labeling site.

The following are 14 classes of preferred semaphorin peptides where bracketed positions may be occupied by any one of the residues contained in the brackets and "X" signifies that the position may be occupied by any one of the 20 naturally encoded amino acids (see, Table 1). These enumerated peptides maintain highly conserved structures which provide important semaphorin binding specificities;

(a) [AspGlu]Cys[GlnLysArgAlaAsn]Asn[TyrPheVal]Ile (SEQ ID NO:1)
Cys[GlnLysArgAlaAsn]Asn[TyrPheVal]Ile[ArgLysGlnThr] (SEQ ID NO:2)

(b) CysGlyThr[AsnGly][AlaSerAsn][TyrPheHisGly][LysArgHisAsnGln] (SEQ ID NO:3)
CysGlyThr[AsnGly][AlaSerAsn]XaaXaaPro (SEQ ID NO:4)
CysGlyThr[AsnGly]XaaXaaXaaProXaa[CysAsp] (SEQ ID NO:5)
CysGlyThrXaaXaaXaaXaaProXaa[CysAsp]XaaXaa[TyrIle] (SEQ ID NO:6)

(c) [ArgIleGlnVal][GlyAla][LeuValLys][CysSer]Pro[PheTyr][AspAsn] (SEQ ID NO:7)
[CysSer]Pro[PheTyr][AspAsn]Pro[AspGluArgLys][HisLeuAsp] (SEQ ID NO:8)
GlyXaa[GlyAla]Xaa[CysSer]ProTyr[AspAsn]Pro (SEQ ID NO:9)

(d) Leu[PheTyr]Ser[GlyAla]Thr[ValAsnAla]Ala (SEQ ID NO:10)
Leu[PheTyr]SerXaaThrXaaAla[AspGlu][PheTyr] (SEQ ID NO:11)
[PheTyr]Ser[GlyAla]Thr[ValAsnAla]Ala[AspGlu][PheTyr] (SEQ ID NO:12)

(e) Leu[AsnAsp][AlaLys]ProAsnPheVal (SEQ ID NO:13)

(f) PhePhePheArgGlu (SEQ ID NO:14)
PhePhe[PheTyr]ArgGlu[ThrAsn] (SEQ ID NO:15)
PhePheArgGlu[ThrAsn]Ala (SEQ ID NO:16)
Phe[PheTyr]ArgGlu[ThrAsn]Ala (SEQ ID NO:17)
TyrPhePhe[PheTyr]ArgGlu (SEQ ID NO:18)
[PheTyr]PhePhe[PheTyr]ArgGlu (SEQ ID NO:19)
[PheTyr][PheTyr][PheTyr]ArgGlu[ThrAsn]Ala (SEQ ID NO:20)
[IleVal][PhrTyr]Phr[PhrTyr][PheTyr]ArgGlu (SEQ ID NO:21)
Asp[LysPheTyr]Val[PheTyr][PheTyIleLeu][PheTyrIleLeu][PheTyr](SEQ ID NO:22)
[ValIle][PheTyr][PheTyrIleLeu][PheTyrIleLeu]Phe[ArgThr]Xaa[ThrAsn](SEQ ID NO:23)
[ValIle][PheTyr][PheTyrIleLeu][PheTyrIleLeu][PheTyr][ArgThr][GluAspVal][ThrAsn] (SEQ ID NO:24)

(g) Glu[PheTyr]IleAsn[CysSer]GlyLys (SEQ ID NO:25)
[PheTyr]IleAsnCysGlyLys[AlaValIle] (SEQ ID NO:26)

(h) Arg[ValIle][AlaGly][ArgGln][ValIle]CysLys (SEQ ID NO:27)
Arg[ValIle]Xaa[ArgGln][ValIle]CysXaaXaaAsp (SEQ ID NO:28)

GlyLys[ValAlaIle]XaaXaaXaaArg[ValAlaIle]XaaXaaXaaCysLys (SEQ ID NO:29)

(i) [ArgLysAsn]Trp[ThrAlaSer][ThrAlaSer][PheTyrLeu]Leu[LysArg] (SEQ ID NO:30)
[PheTyr]Leu[LysArg][AlaSer]ArgLeu[AsnIle]Cys (SEQ ID NO:3 1)
[AsnIle]CysSer[IleVal][ProSer]Gly (SEQ ID NO:32)
Trp[ThrAlaSer][ThrAlaSer][PheTyrLeu]LeuLys[AlaSerValIleLeu]XaaLeu (SEQ ID NO:33)
Trp[ThrAlaSer][ThrAlaSer]XaaLeuLysXaaXaaLeuXaaCys (SEQ ID NO:34)
TrpXaa[ThrSer]XaaLeuLysXaaXaaLeuXaaCys (SEQ ID NO:35)

(j) [PheTyr][PheTyr][AsnAsp]GluIleGlnSer (SEQ ID NO:36)
[PheTyr]Pro[PheTyr][PheTyr][PheTyr][AsnAsp]Glu (SEQ ID NO:37)

(k) GlySerAla[ValIleLeu]CysXaa[PheTyr] (SEQ ID NO:38)
SerAla[ValIleLeu]CysXaa[PheTyr]XaaMet (SEQ ID NO:39)

(l) AsnSer[AsnAla]TrpLeu[ProAla]Val (SEQ ID NO:40)

(m) [ValLeuIle]Pro[GluAspTyrSerPhe]ProArgProGly (SEQ ID NO:41)
[ValLeuIle]ProXaaPro[ArgAla]ProGlyXaaCys (SEQ ID NO:42)
Pro[GluAspTyrSerPhe]ProArgProGly[ThrGlnSer]Cys (SEQ ID NO:43)

(n) AspPro[HisPheTyr]Cys[AlaGly]Trp (SEQ ID NO:44)
Pro[HisPheTyr]Cys[AlaGly]TrpAsp (SEQ ID NO:45)
AspProXaaCys[AlaGly]TrpAsp (SEQ ID NO:46)
CysXaaXaaXaaXaaAspProXaaCysXaaTrpAsp (SEQ ID NO:47)
CysXaaXaaXaaAspProXaaCysXaaTrpAsp (SEQ ID NO:48)
CysXaaXaaAspProXaaCysXaaTrpAsp (SEQ ID NO:49)
CysXaaXaaCysXaaXaaXaaXaaAspXaaXaaCysXaaTrpAsp (SEQ ID NO:50)
CysXaaXaaCysXaaXaaXaaAspXaaXaaCysXaaTrpAsp (SEQ ID NO:51)
CysXaaXaaCysXaaXaaAspXaaXaaCysXaaTrpAsp (SEQ ID NO:52).

The following peptides represent particularly preferred members of each class:

(a) AspCysGlnAsnTyrIle (SEQ ID NO:67)
(b) CysGlyThr[AsnGly][AlaSer]XaaXaaPro (SEQ ID NO:68)
(c) GlyXaa[SerCys]ProTyrAspPro (SEQ ID NO:69)
(d) LeuTyrSerGlyThr[ValAsnAla]Ala (SEQ ID NO:70)
(e) LeuAsnAlaProAsnPheVal (SEQ ID NO:71)
(f) [PheTyr]PhePhe[PheTyr]ArgGlu (SEQ ID NO:19)
(g) Glu[PheTyr]IleAsn[CysSer]GlyLys (SEQ ID NO:25)
(h) Arg[ValIle]AlaArgValCysLys (SEQ ID NO:72)
(i) Trp[ThrAla][ThrSer][PheTyr]LeuLys[AlaSer]ArgLeu (SEQ ID NO:73)
(j) ProPheTyrPhe[AsnAsp]GluIeGlnSer (SEQ ID NO:74)
(k) GlySerAlaValCysXaa[PheTyr] (SEQ ID NO:75)
(l) AsnSerAsnTrpLeu[ProAla]Val (SEQ ID NO:76)
(m) Pro[GluAsp]ProArgProGly[ThrGlnSer]Cys (SEQ ID NO:77)
(n) AspProTyrCys[AlaGly]TrpAsp (SEQ ID NO:78).

The following 14 classes are preferred peptides which exclude semaphorin peptides encoded in open reading frames of Variola major or Vaccinia viruses.

(a) [AspGlu]Cys[GlnLysArgAlaAsn]Asn[TyrPheVal]Ile (SEQ ID NO:01)
Cys[GlnLysArgAlaAsn]Asn[TyrPheVal]Ile[ArgLysGlnThr] (SEQ ID NO:02)

(b) CysGlyThr[AsnGly][AlaSer][TyrPheHisGly][LysArgHisAsnGln] (SEQ ID NO:79)
CysGlyThr[AsnGly][AlaSerAsn][TyrPheHis][LysArgHisAsnGln] (SEQ ID NO:80)
CysGlyThr[AsnGly][AlaSer]XaaXaaPro (SEQ ID NO:81)
(c)[ArgleGlnVal][GlyAla][LeuValLys][CysSer]Pro[PheTyr][AspAsn] (SEQ ID NO:07)
[CysSer]Pro[PheTyr][AspAsn]Pro[AspGluArgLys][HisLeuAsp] (SEQ ID NO:08)
GlyXaa[GlyAla]Xaa[CysSer]ProTyr[AspAsn]Pro (SEQ ID NO:09)
(d) Leu[PheTyr]Ser[GlyAla]Thr[ValAsnAla]Ala (SEQ ID NO:10)
Leu[PheTyr]SerXaaThrXaaAla[AspGlu][PheTyr] (SEQ ID NO:11)
[PheTyr]Ser[GlyAla]Thr[ValAsnAla]Ala[AspGlu][PheTyr] (SEQ ID NO:12)
(e) Leu[AsnAsp][AlaLys]ProAsnPheVal (SEQ ID NO:13)
(f) PhePhePheArgGlu (SEQ ID NO:14)
PhePhe[PheTyr]ArgGlu[ThrAsn] (SEQ ID NO:15)
PhePheArgGlu[ThrAsn]Ala (SEQ ID NO:16)
Phe[PheTyr]ArgGlu[ThrAsn]Ala (SEQ ID NO:17)
TyrPhePhe[PheTyr]ArgGlu (SEQ ID NO:18)
[PheTyr]PhePhe[PheTyr]ArgGlu (SEQ ID NO:19)
[PheTyr][PheTyr][PheTyr]ArgGlu[ThrAsn]Ala (SEQ ID NO:20)
[IleVal][PheTyr]Phe[PheTyr][PheTyr]ArgGlu (SEQ ID NO :21)
Asp [LysPheTyr]Val [PheTyr][PheTyrLeu][PheTyrIleLeu][PheTyr] (SEQ ID NO:22)
Asp[LysPheTyr]Val[PheTyr][PheTyrIleLeu][PheTyrIle][PheTyr] (SEQ ID NO:82)
[ValIle][PheTyr][PheTyrLeu][PheTyrIleLeu]Phe[ArgThr]Xaa[ThrAsn] (SEQ ID NO:83)
[ValIle][PheTyr][PheTyrIleLeu][PheTyrIle]Phe[ArgThr]Xaa[ThrAsn] (SEQ ID NO:84)
[ValIle][PheTyr][PheTyrIleLeu][PheTyrIleLeu]PheArgXaa[ThrAsn] (SEQ ID NO:85)
[ValIle][PheTyr][PheTyrLeu][PheTyrIleLeu][PheTyr][ArgThr][GluAspVal][ThrAsn] (SEQ ID NO: 86)
(g) Glu[PheTyr]IleAsn[CysSer]GlyLys (SEQ ID NO:25)
[PheTyr]IleAsnCysGlyLys[AlaValIle] (SEQ ID NO:26)
(h) Arg[ValIle][AlaGly][ArgGln][ValIle]CysLys (SEQ ID NO:27)
Arg[ValIle]Xaa[ArgGln][ValIle]CysXaaXaaAsp (SEQ ID NO:28)
GlyLys[ValAlaIle]XaaXaaXaaArg[ValAlaIle]XaaXaaXaaCysLys (SEQ ID NO:29)
(i) [ArgLysAsn]Trp[ThrAla][ThrAlaSer][PheTyrLeu]Leu[LysArg] (SEQ ID NO:87)
[PheTyr]Leu[LysArg][AlaSer]ArgLeu[AsnIle]Cys (SEQ ID NO:31)
[AsnIle]CysSer[IleVal][ProSer]Gly (SEQ ID NO:32)
Trp[ThrAla][ThrAlaSer][PheTyrLeu]LeuLys[AlaSerValIleLeu]XaaLeu (SEQ ID NO:88)
Trp[ThrAlaSer][ThrAlaSer][PheTyrLeu]LeuLys[AlaSerIleLeu]XaaLeu (SEQ ID NO:89)
Trp[ThrAla][ThrAlaSer]XaaLeuLysXaaXaaLeuXaaCys (SEQ ID NO:90)
(j) [PheTyr][PheTyr][AsnAsp]GluIleGlnSer (SEQ ID NO:36)
[PheTyr]Pro[PheTyr][PheTyr][PheTyr][AsnAsp]Glu (SEQ ID NO:37)
(k) GlySerAla[ValIleLeu]CysXaa[PheTyr] (SEQ ID NO:38)
SerAla[ValIle]CysXaa[PheTyr]XaaMet (SEQ ID NO:39)
(l) AsnSer[AsnAla]TrpLeu[ProAla]Val (SEQ ID NO:40)

(m) [ValLeuIle]Pro[GluAspTyrSerPhe]ProArgProGly (SEQ ID NO:41)
[ValLeuIle]ProXaaProArgProGlyXaaCys (SEQ ID NO:91)
Pro[GluAspTyrSerPhe]ProArgProGly[ThrGlnSer]Cys (SEQ ID NO:43)
(n) AspPro[HisPheTyr]Cys[AlaGly]Trp (SEQ ID NO:44)
Pro[HisPheTyr]Cys[AlaGly]TrpAsp (SEQ ID NO:45)
AspProXaaCys[AlaGly]TrpAsp (SEQ ID NO:46)
CysXaaXaaXaaXaaAspProXaaCysXaaTrpAsp (SEQ ID NO:47)
CysXaaXaaXaaAspProXaaCysXaaTrpAsp (SEQ ID NO:48)
CysXaaXaaAspProXaaCysXaaTrpAsp (SEQ ID NO:49)
CysXaaXaaCysXaaXaaXaaXaaAspXaaXaaCysXaaTrpAsp (SEQ ID NO:50)
CysXaaXaaCysXaaXaaXaaAspXaaXaaCysXaaTrpAsp (SEQ ID NO :51)
CysXaaXaaCysXaaXaaAspXaaXaaCysXaaTrpAsp (SEQ ID NO:52).

The following 2 classes are preferred peptides which exclude semaphorin peptides encoded in open reading frames of Variola major or Vaccinia viruses Grasshopper Semaphorin I.
(f) TyrPhePhe[PheTyr]ArgGlu (SEQ ID NO:18)
Asp[LysTyr]Val[PheTyr][PheTyrLeu][PheTyrIleLeu][PheTyr] (SEQ ID NO:92)
Asp[LysTyr]Val[PheTyr][PheTyrIleLeu][PheTyrIle][PheTyr] (SEQ ID NO:93)
[ValIle]Tyr[PheTyrLeu][PheTyrIleLeu]Phe[ArgThr]Xaa[ThrAsn] (SEQ ID NO:94)
[ValIle]Tyr[PheTyrIleLeu][PheTyrIle]Phe[ArgThr]Xaa[ThrAsn] (SEQ ID NO:95)
[ValIle]Tyr[PheTyrIleLeu][PheTyrIleLeu]PheArgXaa[ThrAsn] (SEQ ID NO:96)
Val[PheTyr][PheTyrLeu][PheTyrIleLeu][PheTyr][ArgThr][GluAspVal][ThrAsn] (SEQ ID NO: 97)
Val[PheTyr][PheTyrIleLeu][PheTyrIle][PheTyr][ArgThr][GluAspVal][ThrAsn] (SEQ ID NO: 98)
Val[PheTyr][PheTyrIleLeu][PheTyrIleLeu][PheTyr]Arg[GluAspVal][ThrAsn] (SEQ ID NO: 99)
(n) CysXaaXaaXaAspProXaaCysXaaTrpAsp (SEQ ID NO:48)
CysXaaXaaAspProXaaCysXaaTrpAsp (SEQ ID NO:49)
CysXaaXaaCysXaaXaaXaaAspXaaXaaCysXaaTrpAsp (SEQ ID NO:51)
CysXaaXaaCysXaaXaaAspXaaXaaCysXaaTrpAsp (SEQ ID NO:52).

The following 5 classes include peptides which encompass peptides encoded in open reading frames of Variola major or Vaccinia viruses. Accordingly, in the event that these viral peptides are not novel per se, the present invention discloses a hitherto unforseen and unforseeable utility for these peptides as immunosuppressants and targets of anti-viral therapy.
(b) CysGlyThr[AsnGly][AlaSerAsn][TyrPheHisGly][LysArgHisAsnGln] (SEQ ID NO:03)
CysGlyThr[AsnGly][AlaSerAsn]XaaXaaPro (SEQ ID NO:04)
CysGlyThr[AsnGly]XaaXaaXaaProXaa[CysAsp] (SEQ ID NO:05)
CysGlyThrXaaXaaXaaXaaProXaa[CysAsp]XaaXaa[TyrIle] (SEQ ID NO:06)
(f) Asp[LysPheTyr]Val[PheTyr][PheTyrIleLeu][PheTyrIleLeu][PheTyr] (SEQ ID NO:22)
[ValIle][PheTyr][PheTyrIleLeu][PheTyrIleLeu]Phe[ArgThr]Xaa[ThrAsn] (SEQ ID NO:23)

Val[PheTyr][PheTyrIleLeu][PheTyrIleLeu][PheTyr]
[ArgThr][GluAspVal][ThrAsn] (SEQ ID NO: 100)
(i) [ArgLysAsn]Trp[ThrAlaSer][ThrAlaSer][PheTyrLeu]
Leu[LysArg] (SEQ ID NO:30)
Trp[ThrAlaSer][ThrAlaSer][PheTyrLeu]LeuLys[AlaSer-
ValIleLeu]XaaLeu (SEQ ID NO: 33)
Trp[ThrAlaSer][ThrAlaSer]XaaLeuLysXaaXaaLeuXaa-
Cys (SEQ ID NO:34)
TrpXaa[ThrSer]XaaLeuLysXaaXaaLeuXaaCys (SEQ ID
NO:35)
(k) SerAla[ValIleLeu]CysXaa[PheTyr]XaaMet (SEQ ID
NO:39)
(m) [ValLeuIle]ProXaaPro[ArgAla]ProGlyXaaCys (SEQ
ID NO:42).

The disclosed semaphorin sequence data are used to define a wide variety of other semaphorin- and semaphorin receptor-specific binding agents using immunologic, chromatographic or synthetic methods available to those skilled in the art.

Of particular significance are peptides comprising unique portions of semaphorin-specific receptors and polypeptides comprising a sequence substantially similar to that of a substantially full-length semaphorin receptor. Using semaphorin peptides, these receptors are identified by a variety of techniques known to those skilled in the art where a ligand to the target receptor is known, including expression cloning as set out in the exemplification below. For other examples of receptor isolation with known ligand using expression cloning, see, Staunton et al (1989) Nature 339, 61; Davis et al (1991) Science 253, 59; Lain et al (1992) Cell 68, 775; Gearing et al (1989) EMBO 8, 3667; Aruffo and Seed (1987) PNAS 84, 8573 and references therein. Generally, COS cells are transfected to express a cDNA library or PCR product and cells producing peptides/polypeptides which bind a semaphorin/receptor peptide/polypeptide are isolated. For neurosemaphorin receptors, fetal brain cDNA libraries are preferred; for immunosemaphorin receptors, libraries derived from activated lymphoid or myeloid cell lines or tissue derived from sites of inflammation or delayed-type hypersensitivity are preferred; and for semaphorin and semaphorin receptor variants used by tumor cells to evade immune surveillance or suppress an immune response (oncosemaphorins), libraries derived from cancerous tissue or tumor cell lines resistant to the host immune system are preferred. Alternatively, PCR primers based upon known semaphorin/receptor sequences such as those disclosed herein are used to amplify PCR product from such tissues/cells. Other receptor/ligand isolation methods using immobilized ligand or antibody are known to those skilled in the art.

Semaphorin receptor peptides with receptor binding specificity are identified by a variety of ways including having conserved consensus sequences with other semaphorin receptors, by crosslinking to ligand or receptor-specific antibody, or preferably, by screening such peptides for semaphorin binding or disruption of semaphorin-receptor binding. Methods for identifying semaphorin receptor peptides with the requisite binding activity are described herein or otherwise known to those skilled in the art. By analogous methods, semaphorin receptor peptides are used to define additional semaphorin peptides with semaphorin binding specificity, particularly receptor specificity.

The various semaphorin and semaphorin receptor peptides are used to define functional domains of semaphorins, identify compounds that associate with semaphorins, design compounds capable of modulating semaphorin-mediated nerve and immune cell function, and define additional semaphorin and semaphorin receptor-specific binding agents. For example, semaphorin mutants, including deletion mutants are generated from the disclosed semaphorin sequences and used to identify regions important for specific protein-ligand or protein-protein interactions, for example, by assaying for the ability to mediate repulsion or preclude aggregation in cell-based assays as described herein. Further, x-ray crystallographic data of the disclosed protein are used to rationally design binding molecules of determined structure or complementarity for modulating growth cone growth and guidance.

Additional semaphorin- and receptor-specific agents include specific antibodies that can be modified to a monovalent form, such as Fab, Fab', or Fv, specifically binding oligopeptides or oligonucleotides and most preferably, small molecular weight organic receptor antagonists. For example, the disclosed semaphorin and receptor peptides are used as immunogens to generate semaphorin- and receptor-specific polyclonal or monoclonal antibodies. See, Harlow and Lane (1988) Antibodies, A Laboratory Manual, Cold Spring Harbor Laboratory, for general methods. Anti-idiotypic antibody, especially internal imaging anti-ids are also prepared using the disclosures herein.

In addition to semaphorin and semaphorin-receptor derived polypeptides and peptides, other prospective agents are screened from large libraries of synthetic or natural compounds. For example, numerous means are available for random and directed synthesis of saccharide, peptide, and nucleic acid based compounds. Alternatively, libraries of natural compounds in the form of bacterial, fungal, plant and animal extracts are available or readily producible. Additionally, natural and synthetically produced libraries and compounds are readily modified through conventional chemical, physical, and biochemical means. See, e.g. Houghten et al. and Lam et al (1991) Nature 354, 84 and 81, respectively and Blake and Litzi-Davis (1992), Bioconjugate Chem 3, 510.

Useful agents are identified with a range of assays employing a compound comprising the subject peptides or encoding nucleic acids. A wide variety of in vitro, cell-free binding assays, especially assays for specific binding to immobilized compounds comprising semaphorin or semaphorin receptor peptide find convenient use. While less preferred, cell-based assays may be used to determine specific effects of prospective agents on semaphorin-receptor binding may be assayed. Optionally, the intracellular C-terminal domain is substituted with a sequence encoding a oligopeptide or polypeptide domain that provides a detectable intracellular signal upon ligand binding different from the natural receptor. Useful intracellular domains include those of the human insulin receptor and the TCR, especially domains with kinase activity and domains capable of triggering calcium influx which is conveniently detected by fluorimetry by preloading the host cells with Fura-2. More preferred assays involve simple cell-free in vitro binding of candidate agents to immobilized semaphorin or receptor peptides, or vice versa. See, e.g. Fodor et al (1991) Science 251, 767 for light directed parallel synthesis method. Such assays are amenable to scale-up, high throughput usage suitable for volume drug screening.

Useful agents are typically those that bind to a semaphorin or disrupt the association of a semaphorin with its receptor. Preferred agents are semaphorin-specific and do not cross react with other neural or lymphoid cell membrane proteins. Useful agents may be found within numerous chemical classes, though typically they are organic compounds; preferably small organic compounds. Small organic compounds have a molecular weight of more than 150 yet less than about 4,500, preferably less than about 1500, more preferably, less than about 500. Exemplary classes include peptides, saccharides, steroids, heterocyclics, polycyclics, substituted aromatic compounds, and the like.

Selected agents may be modified to enhance efficacy, stability, pharmaceutical compatibility, and the like. Structural identification of an agent may be used to identify, generate, or screen additional agents. For example, where peptide agents are identified, they may be modified in a variety of ways as described above, e.g. to enhance their proteolytic stability. Other methods of stabilization may include encapsulation, for example, in liposomes, etc.

The subject binding agents may be prepared in a variety of ways known to those skilled in the art. For example, peptides under about 60 amino acids can be readily synthesized today using conventional commercially available automatic synthesizers. Alternatively, DNA sequences may be prepared encoding the desired peptide and inserted into an appropriate expression vector for expression in a prokaryotic or eukaryotic host. A wide variety of expression vectors are available today and may be used in conventional ways for transformation of a competent host for expression and isolation. If desired, the open reading frame encoding the desired peptide may be joined to a signal sequence for secretion, so as to permit isolation from the culture medium. Methods for preparing the desired sequence, inserting the sequence into an expression vector, transforming a competent host, and growing the host in culture for production of the product may be found in U.S. Pat. Nos. 4,710,473, 4,711,843 and 4,713,339.

For therapeutic uses, the compositions and agents disclosed herein may be administered by any convenient way, preferably parenterally, conveniently in a pharmaceutically or physiologically acceptable carrier, e.g., phosphate buffered saline, saline, deionized water, or the like. Typically, the compositions are added to a retained physiological fluid such as blood or synovial fluid. For CNS administration, a variety of techniques are available for promoting transfer of the therapeutic across the blood brain barrier including disruption by surgery or injection, drugs which transciently open adhesion contact between CNS vasculature endothelial cells, and compounds which fascilitate translocation through such cells. As examples, many of the disclosed therapeutics are amenable to directly injected or infused, contained within implants e.g. osmotic pumps, grafts comprising appropriately transformed cells. Generally, the amount administered will be empirically determined, typically in the range of about 10 to 1000 µg/kg of the recipient. For peptide agents, the concentration will generally be in the range of about 50 to 500 µg/ml in the dose administered. Other additives may be included, such as stabilizers, bactericides, etc. These additives will be present in conventional amounts.

The invention provides isolated nucleic acid sequences encoding the disclosed semaphorin and semaphorin receptor peptides and polypeptides, including sequences substantially identical to sequences encoding such polypeptides. An "isolated" nucleic acid sequence is present as other than a naturally occurring chromosome or transcript in its natural state and typically is removed from at least some of the nucleotide sequences with which it is normally associated with on a natural chromosome. A complementary sequence hybridizes to a unique portion of the disclosed semaphorin sequence under low stringency conditions, for example, at 50° C. and SSC (0.9 M saline/0.09 M sodium citrate) and that remains bound when subject to washing at 55° C with SSC. Regions of non-identity of complementary nucleic acids are preferably or in the case of homologous nucleic acids, a nucleotide change providing a redundant codon. A partially pure nucleotide sequence constitutes at least about 5%, preferably at least about 30%, and more preferably at least about 90% by weight of total nucleic acid present in a given fraction.

Unique portions of the disclosed nucleic acid sequence are of length sufficient to distinguish previously known nucleic acid sequences. Thus, a unique portion has a nucleotide sequence at least long enough to define a novel oligonucleotide. Preferred nucleic acid portions encode a unique semaphorin peptide. The nucleic acids of the invention and portions thereof, other than those used as PCR primers, are usually at least about 60 bp and usually less than about 60 kb in length. PCR primers are generally between about 15 and 100 nucleotides in length.

Nucleotide (cDNA) sequences encoding several full length semaphorins are disclosed herein. The invention also provides for the disclosed sequences modified by transitions, transversions, deletions, insertions, or other modifications such as alternative splicing and also provides for genomic semaphorin sequences, and gene flanking sequences, including regulatory sequences; included are DNA and RNA sequences, sense and antisense. Preferred DNA sequence portions include portions encoding the preferred amino acid sequence portions disclosed above. For antisense applications where the inhibition of semaphorin expression is indicated, especially useful oligonucleotides are between about 10 and 30 nucleotides in length and include sequences surrounding the disclosed ATG start site, especially the oligonucleotides defined by the disclosed sequence beginning about 5 nucleotides before the start site and ending about 10 nucleotides after the disclosed start site. Other especially useful semaphorin mutants involve deletion or substitution modifications of the disclosed cytoplasmic C-termini of transmembrane semaphorins. Accordingly, semaphorin mutants with semaphorin binding affinities but with altered intracellular signal transduction capacities are produced.

For modified semaphorin-encoding sequences or related sequences encoding proteins with semaphorin-like functions, there will generally be substantial sequence identity between at least a segment thereof and a segment encoding at least a portion of the disclosed semaphorin sequence, preferably at least about 60%, more preferably at least 80%, most preferably at least 90% identity. Homologous segments are particularly within semaphorin domain-encoding regions and regions encoding protein domains involved in protein-protein, particularly semaphorin-receptor interactions and differences within such segments are particularly conservative substitutions.

Typically, the invention's semaphorin peptide encoding polynucleotides are associated with heterologous sequences. Examples of such heterologous sequences include regulatory sequences such as promoters, enhancers, response elements, signal sequences, polyadenylation sequences, etc., introns, 5' and 3' noncoding regions, etc. Other useful heterologous sequences are known to those skilled in the art or otherwise disclosed references cited herein. According to a particular embodiment of the invention, portions of the semaphorin encoding sequence are spliced with heterologous sequences to produce soluble, secreted fusion proteins, using appropriate signal sequences and optionally, a fusion partner such as β-Gal.

The disclosed sequences are also used to identify and isolate other natural semaphorins and analogs. In particular, the disclosed nucleic acid sequences are used as hybridization probes under low-stringency or PCR primers, e.g. oligonucleotides encoding functional semaphorin domains are $^{32}$P-labeled and used to screen λcDNA libraries at low stringency to identify similar cDNAs that encode proteins with related functional domains. Additionally, nucleic acids encoding at least a portion of the disclosed semaphorin are used to characterize tissue specific expression of semaphorin as well as changes of expression over time, particularly during organismal development or cellular differentiation.

The semaphorin encoding nucleic acids can be subject to alternative purification, synthesis, modification, sequencing, expression, transfection, administration or other use by methods disclosed in standard manuals such as Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley-Interscience, NY, N.Y., 1992) or that are otherwise known in the art. For example, the nucleic acids can be modified to alter stability, solubility, binding affinity and specificity, etc. semaphorin-encoding sequences can be selectively methylated, etc. The nucleic acid sequences of the present invention may also be modified with a label capable of providing a detectable signal, either directly or indirectly. Exemplary labels include radioisotopes, fluorescers, biotinylation, etc.

The invention also provides vectors comprising nucleic acids encoding semaphorin peptides, polypeptides or analogs. A large number of vectors, including plasmid and viral vectors, have been described for expression in a variety of eukaryotic and prokaryotic hosts. Advantageously, vectors may also include a promotor operably linked to the semaphorin-encoding portion. Vectors will often include one or more replication systems for cloning or expression, one or more markers for selection in the host, e.g. antibiotic resistance. The inserted semaphorin coding sequences may be synthesized, isolated from natural sources, prepared as hybrids, etc. Suitable host cells may be transformed/transfected/infected by any suitable method including electroporation, CaCl$_2$ mediated DNA uptake, viral infection, microinjection, microprojectile, or other methods.

Appropriate host cells include bacteria, archebacteria, fungi, especially yeast, and plant and animal cells, especially mammalian cells. Of particular interest are *E. coli, B. subtilis, Saccharomyces cerevisiae*, SF9 cells, C129 cells, 293 cells, Neurospora, and CHO, COS, HeLa cells, immortalized mammalian myeloid and lymphoid cell lines, and pluripotent cells, especially mammalian ES cells and zygotes. Preferred replication systems include M13, ColE1, SV40, baculovirus, lambda, adenovirus, AAV, BPV, etc. A large number of transcription initiation and termination regulatory regions have been isolated and shown to be effective in the transcription and translation of heterologous proteins in the various hosts. Examples of these regions, methods of isolation, manner of manipulation, etc. are known in the art. Under appropriate expression conditions, host cells can be used as a source of recombinantly produced semaphorins or analogs.

For the production of stably transformed cells and transgenic animals, nucleic acids encoding the disclosed semaphorins may be integrated into a host genome by recombination events. For example, such a sequence can be microinjected into a cell, and thereby effect homologous recombination at the site of an endogenous gene, an analog or pseudogene thereof, or a sequence with substantial identity to an semaphorin-encoding gene. Other recombination-based methods such as nonhomologous recombinations, deletion of endogenous gene by homologous recombination, especially in pluripotent cells, etc., provide additional applications. Preferred transgenics and stable transformants overexpress the disclosed receptor gene and find use in drug development and as a disease model. Alternatively, knockout cells and animals find use in development and functional studies. Methods for making transgenic animals, usually rodents, from ES cells or zygotes are known to those skilled in the art.

The compositions and methods disclosed herein may be used to effect gene therapy. See, e.g. Zhu et al. (1993) Science 261, 209–211; Gutierrez et al. (1992) Lancet 339, 715–721. For example, cells are transfected with semaphorin sequences operably linked to gene regulatory sequences capable of effecting altered semaphorin expression or regulation. To modulate semaphorin translation, cells may be transfected with complementary antisense polynucleotides. For gene therapy involving the transfusion of semaphorin transfected cells, administration will depend on a number of variables that are ascertained empirically. For example, the number of cells will vary depending on the stability of the transfused cells. Transfusion media is typically a buffered saline solution or other pharmacologically acceptable solution. Similarly the amount of other administered compositions, e.g. transfected nucleic acid, protein, etc., will depend on the manner of administration, purpose of the therapy, and the like.

The following examples are offered by way of illustration and not by way of limitation.

EXAMPLES

I. Isolation and Characterization of Grasshopper Semaphorin I (SEQ ID NOS: 57 and 58(Previously Referred to as Fasciclin IV)

In order to identify cell surface molecules that function in selective fasciculation, a series of monoclonal antibody (MAb) screens was conducted. The immunogen used for most of these screens was membranes from the longitudinal connectives (the collection of longitudinal axons) between adjacent segmental ganglia of the nervous system of the larval grasshopper. From these screens, MAb 3B11 and 8C6 were used to purify and characterize two surface glycoproteins, fasciclin I and fasciclin II, see, Bastiani et al., 1987; the genes encoding both were subsequently cloned, see, Snow et al. 1989, Zinn et al. 1988, and Harrelson and Goodman, 1988.

Another MAb isolated during these screens, MAb 6F8, was chosen for the present study because, just as with fasciclin I and fasciclin II, the antigen recognized by this MAb is expressed on a different but overlapping subset of axon pathways in the developing CNS. The 6F8 antigen appears to be localized on the outside of cell surfaces, as indicated by MAb binding when incubated both in live preparations, and in fixed preparations in which no detergents have been added. Because the 6F8 antigen is a surface glycoprotein expressed on a subset of axon fascicles (see below), we call it fasciclin IV.

Fasciclin IV expression begins early in embryonic development before axonogenesis. At 29% of development, expression is seen on the surface of the midline mesectodermal cells and around 5–7 neuroblasts and associated ectodermal cells per hemisegment. This expression is reminiscent of the mesectodermal and neuroblast-associated expression observed with both fasciclin I and fasciclin II; however, in each case, the pattern resolves into a different subset of neuroblasts and associated ectodermal cells.

At 32% of development, shortly after the onset of axonogenesis in the CNS, fasciclin IV expression is seen on the surface of the axons and cell bodies of the three pairs of MP4, MP5, and MP6 midline progeny, the three U motoneurons, and on several unidentified neurons in close proximity to the U's. This is in contrast to fasciclin II, which at this stage is expressed on the MP1 and dMP2 neurons, and fasciclin I, which is expressed on the U neurons but not on any midline precursor progeny.

The expression of fasciclin IV on a subset of axon pathways is best observed around 40% of development, after the establishment of the first longitudinal and commissural axon pathways. At this stage, the protein is expressed on two longitudinal axon fascicles, a subset of commissural axon fascicles, a tract extending anteriorly along the midline, and a subset of fascicles in the segmental nerve (SN) and intersegmental nerve (ISN) roots.

Specifically, fasciclin IV is expressed on the U fascicle, a longitudinal pathway (between adjacent segmental neuromeres) pioneered in part by the U neurons, and on the A/P longitudinal fascicle (in part an extension of the U fascicle within each segmental neuromere). In addition, fasciclin IV is also expressed on a second narrower, medial, and more ventral longitudinal pathway. The U axons turn and exit the CNS as they pioneer the ISN; the U's and many other axons within the ISN express fasciclin IV. The continuation of the U fascicle posterior to the ISN junction is also fasciclin IV-positive. The specificity of fasciclin IV for distinct subsets of longitudinal pathways can be seen by comparing fasciclin IV and fasciclin II expression in the same embryo; fasciclin IV is expressed on the U and A/P pathways whereas fasciclin II is expressed on the MP1 pathway.

The axons in the median fiber tract (MFT) also express fasciclin IV. The MFT is pioneered by the three pairs of progeny of the midline precursors MP4, MP5, and MP6. The MFT actually contains three separate fascicles. The axons of the two MP4 progeny pioneer the dorsal MFT fascicle and then bifurcate at the posterior end of the anterior commissure; whereas the axons of the two MP6 progeny pioneer the ventral MFT fascicle and then bifurcate at the anterior end of the posterior commissure. Fasciclin IV is expressed on the cell bodies of the six MP4, MP5, and MP6 neurons, and on their growth cones and axons as they extend anteriorly in the MFT and bifurcate in one of the two commissures. However, this expression is regional in that once these axons bifurcate and begin to extend laterally across the longitudinal pathways and towards the peripheral nerve roots, their expression of fasciclin IV greatly decreases. Thus, fasciclin IV is a label for the axons in the MFT and their initial bifurcations in both the anterior and posterior commissures. It appears to be expressed on other commissural fascicles as well. However, the commissural expression of fasciclin IV is distinct from the transient expression of fasciclin II along the posterior edge of the posterior commissure, or the expression of fasciclin I on several different commissural axon fascicles in both the anterior and posterior commissure (Bastiani et al., 1987; Harrelson and Goodman, 1988).

Fasciclin IV is also expressed on a subset of motor axons exiting the CNS in the SN. The SN splits into two major branches, one anterior and the other posterior, as it exits the CNS. Two large bundles of motoneuron axons in the anterior branch express fasciclin IV at high levels; one narrow bundle of motoneuron axons in the posterior branch expresses the protein at much lower levels. Fasciclin IV is also expressed on many of the axons in the ISN.

The CNS and nerve root expression patterns of fasciclin IV, fasciclin I, and fasciclin II around 40% of embryonic development are summarized below. Although there is some overlap in their patterns (e.g., both fasciclin IV and fasciclin I label the U axons), these three surface glycoproteins label distinct subsets of axon pathways in the developing CNS.

Fasciclin IV is Expressed on Epithelial Bands in the Developing Limb Bud

Fasciclin IV is expressed on the developing limb bud epithelium in circumferential bands; at 34.5% of development these bands can be localized with respect to constrictions in the epithelium that mark presumptive segment boundaries. In addition to a band just distal to the trochanter/coxa segment boundary, bands are also found in the tibia, femur, coxa, and later in development a fifth band is found in the tarsus. Fasciclin IV is also expressed in the nascent chordotonal organ in the dorsal aspect of the femur. The bands in the tibia, trochanter, and coxa completely encircle the limb. However, the femoral band is incomplete, containing a gap on the anterior epithelia of this segment.

The position of the Ti1 axon pathway with respect to these bands of fasciclin IV-positive epithelia suggests a potential role for fasciclin IV in guiding the Ti1 growth cones. First, the band of fasciclin IV expression in the trochanter, which is approximately three epithelial cell diameters in width when encountered by the Ti1 growth cones, is the axial location where the growth cones reorient from proximal migration to circumferential branch extension. The Tr1 cell, which marks the location of the turn, lies within this band, usually over the central or the proximal cell tier. Secondly, although there is a more distal fasciclin IV expressing band in the femur, where a change in Ti1 growth is not observed, there exists a gap in this band such that fasciclin IV expressing cells are not traversed by the Ti1 growth cones. The Ti1 axons also may encounter a fasciclin IV expressing region within the coxa, where interactions between the growth cones, the epithelial cells, and the Cx1 guidepost cells have not yet been investigated. In addition to its expression over the surface of bands of epithelial cells, fasciclin IV protein, as visualized with MAb 6F8, is also found on the basal surface of these cells in a punctate pattern. This punctate staining is not an artifact of the HRP immunocytochemistry since fluorescent visualization of MAb 6F8 is also punctate. The non-neuronal expression of fasciclin IV is not restricted to limb buds. Circumferential epithelial bands of fasciclin IV expression are also seen on subesophageal mandibular structures and on the developing antennae.

MAb Directed Against Fasciclin IV can Alter the Formation of the Ti1 Axon Pathway in the Limb Bud The expression of fasciclin IV on an epithelial band at a key choice point in the formation of the Ti1 axon pathway led us to ask whether this protein is involved in growth cone guidance at this location. To answer this question, we cultured embryos, or epithelial fillets (e.g., O'Connor et al., 1990), during the 5% of development necessary for normal pathway formation, either in the presence or absence of MAb 6F8 or 6F8 Fab fragments. Under the culture conditions used for these experiments, defective Ti1 pathways are observed in 14% of limbs (Chang et al., 1992); this defines the baseline of abnormalities observed using these conditions. For controls we used other MAbs and their Fab fragments that either bind to the surfaces of these neurons and epithelial cells (MAb 3B11 against the surface protein fasciclin I) or do not (MAb 4D9 against the nuclear protein engrailed; Patel et al., 1989). To assess the impact of MAb 6F8 on Ti1 pathway formation, we compared the percentage of aberrant pathways observed following treatment with MAb 6F8 to that observed with MAbs 3B11 and 4D9. Our cultures began at 32% of development when the Ti1 growth cones have not yet reached the epithelium just distal to the trochanter/coxa boundary and therefore have not encountered epithelial cells expressing fasciclin IV. Following approximately 30 hours in culture (~4% of development), embryos were fixed and immunostained with antibodies to HRP in order to visualize the Ti1 axons and other neurons in the limb bud. Criteria for scoring the Ti1 pathway, and the definition of "aberrant", are described in detail in the Experimental Procedures.

Although MAb 6F8 does not arrest pathway formation, several types of distinctive, abnormal pathways are observed. These defects generally begin where growth cones first contact the fasciclin IV expressing cells in the trochanter. Normally, the Ti1 neurons each have a single axon, and the axons of the two cells are fasciculated in that portion of the pathway within the trochanter. Following treatment with MAb 6F8, multiple long axon branches are observed within, and proximal to, the trochanter. Two major classes of pathways are taken by these branches; in 36% of aberrant limbs, multiple, long axon branches extend ventrally in the region distal to the Cx1 cells which contains the band of fasciclin IV expressing epithelial cells. In the ventral region of the trochanter, these branches often independently turn proximally to contact the Cx1 cells, and thus complete the pathway in this region.

In the second major class of pathway defect, seen in 47% of aberrant limbs, axon branches leave the trochanter at abnormal, dorsal locations, and extend proximally across the trochanter/coxa boundary. These axons then veer ventrally, often contacting the Cx1 neurons. The remaining 17% of defects include defasciculation distal to the trochanter, axon branches that fail to turn proximally in the ventral trochanter and continue into the posterior compartment of the limb, and axon branches which cross the trochanter/coxa boundary and continue to extend proximally without a ventral turn.

When cultured in the presence of MAb 6F8, 43% of limbs exhibited malformed Ti1 pathways (n=381) as compared to 11% with MAb 3B11 (n=230) and 5% with MAb 4D9 (n=20). These percentages are pooled from treatments with MAbs concentrated from hybridoma supernatant, IgGs isolated from these supernatants, and Fab fragments isolated from these IgG preparations (see Experimental Procedures). The frequency of malformed Ti1 pathways and the types of defects observed showed no significant variation regardless of the method of antibody preparation or type of antibody used. Since Fabs show similar results as IgGs, the effects of MAb 6F8 are not due to cross linking by the bivalent IgG.

In summary, following treatment with MAb 6F8, the Ti1 pathway typically exhibits abnormal morphology beginning just distal to the trochanter and at the site of fasciclin IV expression. The two most common types of Ti1 pathway defects described above occur in 36% of experimental limbs (treated with MAb 6F8), but are seen in only 4% of control limbs (treated with MAbs 3 B11 and 4D9).

Fasciclin IV cDNAs Encode a Novel Integral Membrane Protein

Grasshopper fasciclin IV was purified by passing crude embryonic grasshopper lysates over a MAb 6F8 column. After affinity purification, the protein was eluted, precipitated, denatured, modified at cysteines, and digested with either trypsin or Lys-C. Individual peptides were resolved by reverse phase HPLC and microsequenced using standard methods.

The amino acid sequences derived from these proteolytic fragments were used to generate oligonucleotide probes for PCR experiments, resulting in products that were used to isolate cDNA clones from the Zinn embryonic grasshopper cDNA library (Snow et al., 1988). Sequence analysis of these cDNAs reveals a single open reading frame (ORF) encoding a protein with two potential hydrophobic stretches of amino acids: an amino-terminal signal sequence of 20 residues and (beginning at amino acid 627) a potential transmembrane domain of 25 amino acids. Thus, the deduced protein has an extracellular domain of 605 amino acids, a transmembrane domain, and a cytoplasmic domain of 78 amino acids. The calculated molecular mass of the mature fasciclin IV protein is 80 kd and is confirmed by Western blot analysis of the affinity purified and endogenous protein as described below. The extracellular domain of the protein includes 16 cysteine residues that fall into three loose clusters but do not constitute a repeated domain and are not similar to other known motifs with cysteine repeats. There are also six potential sites for N-linked glycosylation in the extracellular domain. Treatment of affinity purified fasciclin IV with N-Glycanase demonstrates that fasciclin IV does indeed contain N-linked oligosaccharides. Fasciclin IV shows no sequence similarity when compared with other proteins in the PIR data base using BLASTP (Altschul et al., 1990), and is therefore a novel type I integral membrane protein.

A polyclonal antiserum directed against the cytoplasmic domain of the protein encoded by the fasciclin IV cDNA was used to stain grasshopper embryos at 40% of development. The observed staining pattern was identical to that seen with MAb 6F8. On Western blots, this antiserum recognizes the protein we affinity purified using MAb 6F8 and then subjected to microsequence analysis. Additionally, the polyclonal serum recognizes a protein of similar molecular mass from grasshopper embryonic membranes. Taken together these data indicate that the sequence we have obtained is indeed fasciclin IV.

Four other cell surface proteins that label subsets of axon pathways in the insect nervous system (fasciclin I, fasciclin II, fasciclin III, and neuroglian) are capable of mediating homophilic cell adhesion when transfected into S2 cells in vitro (Snow et al., 1989; Elkins et al., 1990b; Grenningloh et al., 1990). To ask whether fasciclin IV can function as a homophilic cell adhesion molecule, the fasciclin IV cDNA with the complete ORF was placed under the control of the inducible metallothionein promoter (Bunch et al., 1988), transfected into S2 cells, and assayed for its ability to promote adhesion in normally non-adhesive S2 cells. Following induction with copper, fasciclin IV was synthesized in these S2 cells as shown by Western blot analysis and cell surface staining of induced S2 cells with the polyclonal antiserum described above.

We observed no evidence for aggregation upon induction of fasciclin IV expression, thus suggesting that, in contrast to the other four proteins, fasciclin IV does not function as a homophilic cell adhesion molecule. Alternatively, fasciclin IV-mediated aggregation might require some further post-translational modification, or co-factor, not supplied by the S2 cells, but clearly this protein acts differently in the S2 cell assay than the other four axonal glycoproteins previously tested. This is consistent with the pattern of fasciclin IV expression in the embryonic limb since only the epithelial cells and not the Ti1 growth cones express fasciclin IV, and yet antibody blocking experiments indicate that fasciclin IV functions in the epithelial guidance of these growth cones.

Such results suggest that fasciclin IV functions in a heterophilic adhesion or signaling system.

Discussion

Fasciclin IV is expressed on groups of axons that fasciculate in the CNS, suggesting that, much like other insect axonal glycoproteins, it functions as a homophilic cell adhesion molecule binding these axons together. Yet, in the limb bud, fasciclin IV is expressed on a band of epithelium but not on the growth cones that reorient along this band, suggesting a heterophilic function. That fasciclin IV functions in a heterophilic rather than homophilic fashion is supported by the lack of homophilic adhesion in S2 cell aggregation assays. In contrast, fasciclin I, fasciclin II, fasciclin III, and neuroglian all can function as homophilic cell adhesion molecules (Snow et al., 1989; Elkins et al., 1990b; Grenningloh et al., 1990).

cDNA sequence analysis indicates that fasciclin IV is an integral membrane protein with a novel sequence not related to any protein in the present data base. Thus, fasciclin IV represents a new type of protein that functions in the epithelial guidance of pioneer growth cones in the developing limb bud. Given its expression on a subset of axon pathways in the developing CNS, fasciclin IV functions in the guidance of CNS growth cones as well.

The results from the MAb blocking experiments illuminate several issues in Ti1 growth cone guidance and axon morphogenesis in the limb. First, the most striking change in growth cone behavior in the limb is the cessation of proximal growth and initiation of circumferential extension of processes upon encountering the trochanter/coxa boundary region (Bentley and Caudy, 1983; Caudy and Bentley, 1987). This could be because the band of epithelial cells within the trochanter promotes circumferential growth, or because the cells comprising the trochanter/coxa boundary and the region just proximal to it are non-permissive or aversive for growth cone migration, or both. The extension of many axon branches across the trochanter/coxa boundary following treatment with MAb 6F8 suggests that the trochanter/coxa boundary cells, which do not express fasciclin IV, are not aversive or non-permissive. Thus the change in behavior at the boundary appears to be due to the ability of fasciclin IV expressing epithelial cells to promote circumferential extension of processes from the Ti1 growth cones.

Secondly, treatment with MAb 6F8 results in frequent defasciculation of the axons of the two Ti1 neurons, and also formation of abnormal multiple axon branches, within the trochanter over fasciclin IV-expressing epithelial cells. Previous studies have shown that treatment with antibodies against ligands expressed on non-neural substrates (Landmesser et al., 1988), or putative competitive inhibitors of substrate ligands (Wang and Denburg, 1992) can promote defasciculation and increased axonal branching. Our results suggest that Ti1 axon:axon fasciculation and axon branching also are strongly influenced by interactions with substrate ligands, and that fasciclin IV appears to be a component of this interaction within the trochanter.

Thirdly, despite the effects of MAb 6F8 on axon branching, and on crossing the trochanter/coxa boundary, there remains a pronounced tendency for branches to grow ventrally both within the trochanter and within the distal region of the coxa. Consequently, all signals which can promote ventral migration of the growth cones have not been blocked by MAb 6F8 treatment. Antibody treatment may have a threshold effect in which ventral growth directing properties of fasciclin IV are more robust, and less incapacitated by treatment, than other features; alternatively, guidance information promoting ventral migration may be independent of fasciclin IV. Time lapse video experiments to determine how the abnormal pathways we observe actually form can resolve these issues.

These results demonstrate that fasciclin IV functions as a guidance cue for the Ti1 growth cones just distal to the trochanter/coxa boundary, is required for these growth cones to stop proximal growth and spread circumferentially, and that the function of fasciclin IV in Ti1 pathway formation result from interactions between a receptor/ligand on the Ti1 growth cones and fasciclin IV on the surface of the band of epithelial cells results in changes in growth cone morphology and subsequent reorientation. Fasciclin IV appears to elicit this change in growth cone morphology and orientation via regulation of adhesion, a signal transduction function, or a combination of the two.

Experimental Procedures

Immunocytochemistry

Grasshopper embryos were obtained from a colony maintained at the U.C. Berkeley and staged by percentage of total embryonic development (Bentley et al., 1979). Embryos were dissected in PBS, fixed for 40 min in PEM-FA [0.1 M PIPES (pH6.95), 2.0 mM EGTA, 1.0 mM $MgSO_4$, 3.7% formaldehyde], washed for 1 hr with three changes in PBT (1× PBS, 0.5% Triton X-100, 0.2% BSA), blocked for 30 min in PBT with 5% normal goat serum, and incubated overnight at 4° C. in primary antibody. PBSap (1× PBS, 0.1% Saponin, 0.2% BSA) was used in place of PBT with MAb 8G7. Antibody dilutions were as follows: MAb 6F8 1:1, polyclonal antisera directed against a fasciclin IV bacterial fusion protein (#98-3) 1:400; MAb 8G7 1:4; MAb 8C6 1:1. The embryos were washed for one hour in PBT with three changes, blocked for 30 min, and incubated in secondary antibody for at least 2 hr at room temperature. The secondary antibodies were HRP-conjugated goat anti-mouse and anti-rat IgG (Jackson Immunoresearch Lab), and were diluted 1:300. Embryos were washed in PBT for one hour with three changes and then reacted in 0.5% diaminobenzidine (DAB) in PBT. The reaction was stopped with several washes in PBS and the embryos were cleared in a glycerol series (50%, 70%, 90%), mounted and viewed under Nomarski or bright field optics. For double-labelled preparations the first HRP reaction was done in PBT containing 0.06% NiCl, followed by washing, blocking, and incubation overnight in the second primary antibody. The second antibody was visualized with a DAB reaction as described above. Embryos cultured in the presence of monoclonal antibodies were fixed and incubated overnight in goat anti-HRP (Jackson Immunoresearch Labs) conjugated to RITC (Molecular Probes), washed for one hour in PBT with three changes, mounted in 90% glycerol, 2.5% DABCO (Polysciences), and viewed under epifluorescence. S2 cells were stained with polyclonal sera #98-3 diluted 1:400 and processed as described previously (Snow et al., 1989).

Monoclonal Antibody Blocking Experiments

In order to test for functional blocking, monoclonal antibody reagents were prepared as follows. Hybridoma supernatant was brought to 20% with $H_2O$-saturated $(NH_4)_2SO_4$, incubated in ice 1 hr, and spun at 15,000 g at 4° C. for 20 min. The supernatant was brought to 56% with $H_2O$-saturated $(NH_4)_2SO_4$, incubated overnight at 4° C., spun as above. The pellet was resuspended in PBS using approximately 1/40 volume of the original hybridoma supernatant (often remaining a slurry) and dialyzed against 1× PBS overnight at 4° C. with two changes. This reagent is referred to as "concentrated hybridoma supernatant." Purified IgG was obtained by using Immunopure Plus Immobilized Protein A IgG Purification Kit (Pierce) to isolate IgG from the concentrated hybridoma supernatant. Fab fragments were obtained using the ImmunoPure Fab Preparation Kit (Pierce) from the previously isolated IgGs. For blocking experiments each reagent was diluted into freshly made supplemented RPMI culture media (O'Connor et al., 1990) and dialyzed overnight at 4° C. against 10 volumes of the same culture media. Dilutions were as follows: concentrated hybridoma supernatant 1:4; purified IgG 150 mg/ml; Fab 75 mg/ml.

Embryos for culture experiments were carefully staged to between 31 and 32% of development. As embryos in each clutch typically differ by less that 1% of embryonic development from each other, the growth cones of the Ti1 neurons at the beginning of the culture period were located approximately in the mid-femur, well distal to the trochanter/coxa segment boundary. From each clutch at least two limbs were filleted and the Ti1 neurons labelled with the lipophillic dye Di I (Molecular Probes) as described (O'Connor et al., 1990) in order to confirm the precise location of the Ti1 growth cones. Prior to culturing, embryos were sterilized and dissected (Chang et al., 1992). The entire amnion and dorsal membrane was removed from the embryo to insure access of the reagents during culturing. Embryos were randomly divided into groups and cultured in one of the blocking reagents described above. Cultures were incubated with occasional agitation at 30° C. for 30 hrs. At the end of the culture period embryos were fixed and processed for analysis as described above in immunocytochemistry.

For each culture experiment, the scoring of the Ti1 pathway in each limb was confirmed independently by a second observer. There was no statistically significant variation between the two observers. Limbs from MAb cultured embryos were compared to representative normal limbs from non-MAb cultured embryos and were scored as abnormal if any major deviation from the normal Ti1 pathway was observed. The Ti1 pathway was scored as abnormal for one or more of the following observed characteristics: (1) defasciculation for a minimum distance of approximately 25 mm anywhere along the pathway, (2) multiple axon branches that extended ventrally within the trochanter, (3) presence of one or more axon branches that crossed the trochanter/coxa boundary dorsal to the Cx1 cells, but then turned ventrally in the coxa and contacted the Cx1 cells, (4) the presence of axon branches that crossed the trochanter/coxa segment boundary, did not turn ventrally, but continued proximally toward the CNS, and (5) failure of ventrally extended axons within the trochanter to contact and reorient proximally to the Cx1 cells. For each MAb tested, the data are presented as a percentage of the abnormal Ti1 pathways observed.

Protein Affinity Purification and Microsequencing

Grasshopper fasciclin IV was purified by passing crude embryonic grasshopper lysate (Bastiani et al., 1987) over an Affi-Gel 15 column (Bio Rad) conjugated with the monoclonal antibody 6F8. Protein was eluted with 50 mM DEA (pH 11.5), 0.1% Lauryldimethylamine oxide (Cal Bio Chem), and 1 mM EDTA. Protein was then precipitated, denatured, modified at cysteines, and digested with either trypsin or Lys-C (Boehringer-Mannheim). Individual peptides were resolved by RP-HPLC and microsequenced (Applied Biosystems 4771 Microsequencer) using standard chemistry.

PCR Methods

DNA complementary to poly(A)+RNA from 45%–50% grasshopper embryos was prepared (Sambrook et al., 1989). PCR was performed using Perkin Elmer Taq polymerase (Saiki et al., 1988), and partially degenerate (based on grasshopper codon bias) oligonucleotides in both orientations corresponding to a portion of the protein sequence of several fasciclin IV peptides as determined by microsequencing. These oligonucleotides were designed so as not to include all of the peptide-derived DNA sequence, leaving a remaining 9–12 base pairs that could be used to confirm the correct identity of amplified products. All possible combinations of these sequences were tried. 40 cycles were performed, the parameters of each cycle as follows: 96° for one min; a sequentially decreasing annealing temperature (2° C./cycle, starting at 65° C. and ending at 55° C. for remaining 35 cycles) for 1 min; and at 72° C. for one min. Reaction products were cloned into the Sma site of M13 mp10 and sequenced. Two products, 1074 bp and 288 bp in length, contained DNA 3' to the oligonucleotide sequences encoded the additional amino acid sequence of the fasciclin IV peptide from which the oligonuceotides were derived.

cDNA Isolation and Sequence Analysis

Both PCR products were used to screen $1 \times 10^6$ clones from a grasshopper embryonic cDNA library (Snow et al., 1988). 21 clones that hybridized to both fragments were recovered, and one 2600 bp clone was sequenced using the dideoxy chain termination method (Sanger et al., 1977) and Sequenase (US Biochemical Corp.). Templates were made from M13 mp10 vectors containing inserts generated by sonication of plasmid clones. One cDNA was completely sequenced on both strands using Oligonucleotides and double strand sequencing of plasmid DNA (Sambrook et al., 1989) to fill gaps. Two additional cDNAs were analyzed by double strand sequencing to obtain the 3' 402 bp of the transcript. All three cDNAs were used to construct a plasmid containing the entire transcript. The complete transcript sequence is 2860 bp in length with 452 bp of 5' and 217 bp of 3' untranslated sequences containing stop codons in all reading frames. The predicted protein sequence was analyzed using the FASTDB and BLASTP programs (Intelligenetics). The fasciclin IV ORF unambiguously contains 10 of the 11 peptide sequences determined by microsequencing the fasciclin IV trypsin and Lys-C peptides.

Generation of Polyclonal Antibodies from Bacterial Fusion Proteins

Bacterial trpE fusion proteins were constructed using pATH (Koerner et al., 1991) vectors, three restriction fragments encoding extracellular sequences, and one fragment (770 bp HindIII/ Eco R1, which includes amino acids 476–730) encoding both extracellular and intracellular sequences (designated #98-3). Fusion proteins were isolated by making an extract of purified inclusion bodies (Spindler et al., 1984), and rats were immunized with ~70 mg of protein emulsified in RIBI adjuvant (Immunochem Research). Rats were injected at two week intervals and serum was collected 7 days following each injection. Sera were tested histologically on grasshopper embryos at 45% of development. Construct #98-3 showed a strong response and exhibited a staining pattern identical to that of MAb 6F8. Two of the extracellular constructs responded weakly but also showed the fasciclin IV staining pattern. All preimmune sera failed to stain grasshopper embryos.

S2 Cell Transfections, Aggregation Assays, and Western Analysis

A restriction fragment containing the full length fasciclin IV cDNA was cloned into pRmHa-3 (Bunch et al, 1988) and co-transformed into Drosophila S2 cells (Schneider, 1972)

with the plasmid pPC4 (Jokerst et al., 1989), which confers a-amanitin resistance. S2 cells were transformed using the Lipofectin Reagent and recommended protocol (BRL) with minor modifications. All other S2 cell manipulations are essentially as described (Snow et al.,1989), including adhesion assays. Fasciclin IV expression in transformed cell lines was induced for adhesion assays and histology by adding $CuSO_4$ to 0.7 mM and incubating for at least 48 hrs. Northern analysis confirmed transcription of fasciclin IV and surface-associated staining of the S2 cells with polyclonal serum #98-3 strongly suggests fasciclin IV is being transported to the cell surface. Preparation of membranes from S2 cells and from grasshopper embryos, PAGE, and Western blot were performed as previously described (Elkins et al., 1990b) except that signal was detected using the enhanced chemiluminescence immunodetection system kit (Amersham). Amount of protein per lane in each sample loaded: fasciclin IV protein, ~5 ng; S2 cell membranes, 40 mg; grasshopper membranes 80 mg. Amounts of protein loaded were verified by Ponceau S staining of the blot prior to incubation with the antibody.

References Cited in Example I

Altschul, S. F., Gish, W., Miller, W., Myers, E. W., and Lipman, D. J. (1990). Basic local alignment search tool. J. Mol. Biol. 215, 403–410.

Bastiani, M. J., de Couet, H. G., Quinn, J. M. A., Karlstrom, R. O., Kotrla, K., Goodman, C. S., and Ball, E. E. (1992). Position-specific expression of the annulin protein during grasshopper embryogenesis. Dev. Biol., in press.

Bastiani, M. J., du Lac, S., and Goodman, C. S. (1986). Guidance of neuronal growth cones in the grasshopper embryo. I. Recognition of a specific axonal pathway by the pCC neuron. J. Neurosci. 6, 3518–3531.

Bastiani, M. J., and Goodman, C. S. (1986). Guidance of neuronal growth cones in the grasshopper embryo: III. Recognition of specific glial pathways. J. Neurosci. 6, 3542–3551.

Bastiani, M. J., Harrelson, A. L., Snow, P. M., and Goodman, C. S. (1987). Expression of fasciclin I and II glycoproteins on subsets of axon pathways during neuronal development in the grasshopper. Cell 48, 745–755.

Bastiani, M. J., Raper, J. A., and Goodman, C. S. (1984). Pathfinding by neuronal growth cones in grasshopper embryos. III. Selective affinity of the G growth cone for the P cells within the A/P fascicle. J. Neurosci. 4, 2311–2328.

Bentley, D., and Caudy, M. (1983). Pioneer axons lose directed growth after selective killing of guidepost cells. Nature. 304, 62–65.

Bentley, D., Keshishian, H., Shankland, M., and Toroian-Raymond, A. (1979). Quantitative staging of embryonic development of the grasshopper, Schistocerca nitens. J. Embryol. Exp. Morph. 54, 47–74.

Bentley, D., and O'Connor, T. P. (1992). Guidance and steering of peripheral pioneer growth cones in grasshopper embryos. In The Nerve Growth Cone, P. C. Letourneau, S. B. Kater, and E. R. Macagno eds. (New York: Raven Press, Ltd.), pp. 265–282.

Bunch, T. A., Grinblat, Y., and Goldstein, L. S. B. (1988). Characterization and use of the Drosophila metallothionein promoter in cultured Drosophila melanogaster cells. Nucleic Acids Res. 16, 1043–1061.

Chang, W. S., Serikawa, K., Allen, K., and Bentley, D. (1992). Disruption of pioneer growth cone guidance in vivo by removal of glycosyl-phosphatidylinositol-anchored cell surface proteins. Development. 114, 507–519.

Caudy, M., and Bentley, D. (1987). Pioneer growth cone behavior at a differentiating limb segment boundary in the grasshopper embryo. Dev. Biol. 119, 454–465.

Chou, P. Y., and Fasman, G. D. (1974). Prediction of protein conformation. Biochemistry. 13, 222–245.

Elkins, T., Zinn, K., McAllister, L., Hoffmann, F. M., and Goodman, C. S. (1990a). Genetic analysis of a Drosophila neural cell adhesion molecule: Interaction of fasciclin I and abelson tyrosine kinase mutations. Cell. 60, 565–575.

Elkins, T., Hortsch, M., Bieber, A. J., Snow, P. M., and Goodman, C. S. (1990b). Drosophila fasciclin I is a novel homophilic adhesion molecule that along with fasciclin III can mediate cell sorting. J. Cell Biol. 110, 1825–1832.

Goodman, C. S., Bate, C. M., and Spitzer, N. C. (1981). Embryonic development of identified neurons: Origin and transformation of the H cell. J. Neurosci. 1, 94–102.

Grenningloh, G., Bieber, A., Rehm, J., Snow, P. M., Traquina, Z., Hortsch, M., Patel, N. H., and Goodman, C. S. (1990). Molecular genetics of neuronal recognition in Drosophila: Evolution and function of immunoglobulin superfamily cell adhesion molecules. Cold Spring Harbor Symp. Quant. Biol. 55, 327–340.

Grenningloh, G., Rehm, E. J., and Goodman, C. S. (1991). Genetic analysis of growth cone guidance in Drosophila: Fasciclin II functions as a neuronal recognition molecule. Cell. 67, 45–57.

Harrelson, A. L., and Goodman, C. S. (1988). Growth cone guidance in insects: Fasciclin II is a member of the immunoglobulin superfamily. Science. 242, 700–708.

Jacobs, J. R., and Goodman, C. S. (1989). Embryonic development of axon pathways in the Drosophila CNS. I. A glial scaffold appears before the first growth cones. J. Neurosci. 7, 2402–2411.

Jay, D. J., and Keshishian, H. (1990). Laser inactivation of fasciclin I disrupts axon adhesion of grasshopper pioneer neurons. Nature. 348,548–551.

Jokerst, R. S., Weeks, J. R. Zehring, W. A., and Greenleaf, A. L. (1989). Analysis of the gene encoding the largest subunit of RNA polymerase II in Drosophila. Mol. Gen. Genet. 215, 266–275.

Koerner, T. J., Hill, J. E., Myers, A. M., and Tzagoloff, A. (1991). High-expression vectors with multiple cloning sites for construction of trpE-fusion genes: pATH vectors. Methods Enzymol. 194, 477–490.

Landmesser, L., Dahm L., Schultz, K., and Rutishauser, U. (1988). Distinct roles for adhesion molecules during innervation of embryonic chick muscle. Dev. Biol. 130, 645–670.

Lefcort, F., and Bentley, D. (1987). Pathfinding by pioneer neurons in isolated, opened and mesoderm-free limb buds of embryonic grasshoppers. Dev. Biol. 119, 466–480.

Lefcort, F., and Bentley, D. (1989). Organization of cytoskeletal elements and organelles preceding growth cone emergence from an identified neuron in situ. J. Cell. Biol. 108, 1737–1749.

O'Connor, T. P., Duerr, J. S., and Bentley, D. (1990). Pioneer growth cone steering decisions mediated by single filopodial contacts in situ. J. Neurosci. 10, 3935–3946.

Patel, N. H., Martin-Blanco, E., Coleman, K. G., Poole, S. J., Ellis, M. C., Kornberg, T. B., and Goodman, C. S. (1989). Expression of engrailed proteins in arthropods, annelids, and chordates. Cell. 58, 955–968.

Patel, N. H., Snow, P. M., and Goodman, C. S. (1987). Characterization and cloning of fasciclin III: A glycoprotein expressed on a subset of neurons and axon pathways in Drosophila. Cell. 48, 975–988.

Raper, J. A., Bastiani, M. J., and Goodman, C. S. (1984). Pathfinding by neuronal growth cones in grasshopper embryos. IV. The effects of ablating the A and P axons upon the behavior of the G growth cone. J. Neurosci. 4, 2329–2345.

Saiki, R. K., Gelfand, D. H., Stoffel, S., Scharf, S. J., Higuchi, R., Horn, G. T., Mullis, K. B., and Ehrlich, H. A. (1988). Primer-directed enzymatic amplification of DNA with a thermostable DNA polymerase. Science 239, 487–494.

Sambrook, J., Fritsch, E. F., and Maniatis, T. (1989). Molecular Cloning: A Laboratory Manual (Cold Spring Harbor, N.Y.: Cold Spring Harbor Laboratory).

Sanger, F., Nicklen, S., and Coulson, A. R. (1977). DNA sequencing with chain-terminating inhibitors. Proc. Natl. Acad. Sci. USA. 74, 5463–5467.

Schneider, I. (1972). Cell lines derived from late embryonic stages of Drosophila melanogaster. J. Embryol. Exp. Morphol. 27, 353–365.

Snow, P. M., Bieber, A. J., and Goodman, C. S. (1989). Fasciclin III: a novel homophilic adhesion molecule in Drosophila. Cell. 59, 313–323.

Snow, P. M., Zinn, K., Harrelson, A. L., McAllister, L., Schilling, J., Bastiani, M. J., Makk, G., and Goodman, C. S. (1988). Characterization and cloning of fasciclin I and fasciclin II glycoproteins in the grasshopper. Proc. Natl. Acad. Sci. USA 85, 5291–5295.

Spindler, K. R., Rosser, D. S., and Berk, A. J. (1984). Analysis of adenovirus transforming proteins from early regions 1A and 1B with antisera to inducible fusion antigens produced in Escherichia coli. J. Virol. 49, 132–141.

Wang, L., and Denburg, J. L. (1992). A role for proteoglycans in the guidance of a subset of pioneer axons in cultured embryos of the cockroach. (1992). Neuron. 8, 701–714.

Wang, L. S., Feng, Y., and Denburg, J. L. (1992). A multifunctional cell surface developmental stage-specific antigen in the cockroach embryo: involvement in pathfinding by CNS pioneer axons. J. Cell Biol. 118, 163–176.

Zinn, K., McAllister, L., and Goodman, C. S. (1988). Sequence analysis and neuronal expression of fasciclin I in grasshopper and Drosophila. Cell. 53, 577–587.

Genbank Accession Number:

The accession number for the sequence reported in this paper is L00709.

II. Isolation and Characterization of Tribolium (SEQ ID NOS:63 and 64) and Drosophila (SEQ ID NOS:59 and 60) Semaphorin I, Drosophila Semaphorin II (SEQ ID NOS:61 and 62), Human Semaphorin III (SEQ ID NOS:53 and 54) and Vaccinia Virus Semaphorin IV (SEQ ID NOS:55 and 56) and Variola Major (smallpox) Virus Semaphorin V (SEQ ID NOS:67 and 68).

We used our G-Semaphorin I cDNA in standard low stringency screening methods (of both cDNA and genomic libraries) in an attempt to isolate a potential Semaphorin I homologue from *Drosophila*. We were unsuccessful in these screens. Since the sequence was novel and shared no similarity to anything else in the data base, we then attempted to see if we could identify a Semaphorin I homologue in other, more closely related insects. If possible, we would then compare these sequences to find the most conserved regions, and then to use probes (i.e., oligonucleotide primers for PCR) based on these conserved regions to find a *Drosophila* homologue.

In the process, we used the G-Semaphorin I cDNA in low stringency screens to clone Semaphorin I cDNAs from libraries made from locust *Locusta migratoria* embryonic RNA and from a cDNA embryonic library from the cricket *Acheta domestica*. We used PCR to clone genomic fragments from genomic DNA in the beetle *Tribolium*, and from the moth *Manduca*. We then used the *Tribolium* genomic DNA fragment to isolate cDNA clones and ultimately sequenced the complete ORF for the *Tribolium* cDNA.

In the meantime, we used the partial *Tribolium* and *Manduca* sequences in combination with the complete grasshopper sequence to identify conserved regions that allowed us to design primers for PCR in an attempt to clone a *Drosophila* Semaphorin I homologue. Several pairs of primers generated several different bands, which were subcloned and sequenced and several of the bands gave partial sequences of the Drosophila Semaphorin homologue. One of the bands gave a partial sequence of what was clearly a different, more divergent gene, which we call D-Semaphorin II.

Based on the sequence of PCR products, we knew we had identified two different *Drosophila* genes, one of which appeared to be the Semaphorin I homologue, and the other a second related gene. The complete ORF sequence of the D-Semaphorin I homologue revealed an overall structure identical to G-Semaphorin I: a signal sequence, an extracellular domain of around 550 amino acids containing 16 cysteines, a transmembrane domain of 25 amino acids, and a cytoplasmic domain of 117 amino acids. When we had finished the sequence for D-Semaphorin II, we were able to begin to run homology searches in the data base, which revealed some of its structural features further described herein. The Semaphorin II sequence revealed a different structure: a signal sequence of 16 amino acids, a ~525 amino acid domain containing 16 cysteines, with a single immunoglobulin (Ig) domain of 66 amino acids, followed by a short unique region of 73 amino acids. There is no evidence for either a transmembrane domain or a potential phospholipid linkage in the C-terminus of this protein. Thus, it appears that the D-Semaphorin II protein is secreted from the cells that produce it. The grasshopper, *Tribolium*, and *Drosophila* Semaphorin I cDNA sequences, as well as the sequence of the D-Semaphorin II cDNA, are shown herein. In addition, we used this same technique to identify Semaphorin I genes in a moth, Manduca sexta, a locust, Locusta migratoria, and a cricket, *Acheta domestica*.

With this large family of insect Semaphorin genes, we identified a number of good stretches of the right amino acids (with the least degeneracy based on their codons) with strong homology for designing primers for PCR to look for human genes. We designed a set of oligonucleotide primers, and plated out several human cDNA libraries: a fetal brain library (Stratagene), and an adult hippocampus library. We ultimately obtained a human cDNA PCR bands of the right size that did not autoprime and thus were good candidates to be bonafide Semaphorin-like cDNAs from humans. These bands were purified, subcloned, and sequenced.

Whole-mount in situ hybridization experiments showed that D-Semaphorin I and II are expressed by different subsets of neurons in the embryonic CNS. D-Semaphorin I is expressed by certain cells along the midline as well as by other neurons, whereas D-Semaphorin II is not expressed at the midline, but is expressed by a different subset of neurons. In addition, D-Semaphorin II is expressed by a subset of muscles prior to and during the period of innervation by specific motoneuron. On the polytene chromosomes, the D-Semaphorin I gene maps to (gene-band-chromosome) 29E1-22L and that of D-Semaphorin II to 53C9-102R. We have identified loss of function mutations in the D-Semaphorin I gene and a pair of P-element transposon insertions in the D-Semaphorin II gene which appear to cause severe phenotypes.

When we lined up the G-Semaphorin I, T-Semaphorin I, D-Semaphorin I, and D-Semaphorin II sequences and ran the sequences through a sequence data base in search of other sequences with significant similarity, we discovered a curious finding: these Semaphorins share sequence similarity with the A39R open reading frame (ORF) from Vaccinia virus and the A43R ORF from Variola Major (smallpox) virus and we discovered that the amino acids shared with the virus ORF were in the same regions where the insect proteins shared their greatest similarity. The viral ORF began with a putative signal sequence, continued for several hundred amino acids with sequence similarity to the i Semaphorin genes, and then ended without any membrane linkage signal (suggesting that the protein as made by the infected cell would likely be secreted).

We reasoned that the virus semaphorins were appropriated host proteins advantageously exploited by the viruses, which would have host counterparts that most likely function in the immune system to inhibit or decrease an immune response, just as in the nervous system they appear to function by inhibiting growth cone extension. Analogous to situations where viruses are thought to encode a secreted form of a host cellular receptor, here the virus may cause the infected cell to make a lot of the secreted ligand to mimic an inhibitory signal and thus help decrease the immune response.

III. Isolation and Characterization of Murine CNS Semaphorin III Receptor Using Epitope Tagged Human Semaphorin III (hSIII)

mRNA was isolated from murine fetal brain tissue and used to construct a cDNA library in a mammalian exprssion vector, pCMX, essentially as in Davis et al. (1991) Science 253, 59.

The transfection and screening procedure is modified from Lin et al (1992) Cell 68, 775. COS cells grown on glass slide flaskettes are transfected with pools of the cDNA clones, allowed to bind radioiodinated hSIII truncated at the C-terminus end of the semaphorin domain. In parallel, similarly treated COS cells are allowed to bind unlabelled human semaphorin m truncated at the C-terminus end of the semaphorin domain and there joined to a 10-amino acid extension derived from the human c-myc proto-oncogene product. This modified hSIII allows the identification of hSIII receptors with the use of the tagged ligand as a bridge between the receptor and a murine monoclonal antibody which is specific for an epitope in the c-myc tag. Accordingly, after binding unlabelled hSIII the cells are exposed to the monoclonal which may be labeled directly or subsequently decorated with a secondary anti-mouse labeled antibody for enhanced signal amplification.

Cells are then fixed and screened using dark-field microscopy essentially as in Lin et al. (supra). Positive clones are identified and sequence analysis of murine CNS Semphorin III receptor cDNA clones by the dideoxy chain termination method is used to construct full-length receptor coding sequences.

It is evident from the above results that one can use the methods and compositions disclosed herein for making and identifying diagnostic probes and therapeutic drugs. It will also be clear to one skilled in the art from a reading of this disclosure that advantage can be taken to effect alterations of semaphorin responsiveness in a host.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

TABLE 1

Deduced amino-acid sequence of semaphorin gene family. Approximate position of enumerated peptide classes are indicated by parenthetical (a) through (o); semaphorin domains are bounded by arrows; G: grasshopper semaphorin I (SEQ ID NO:58), T: Tribolium semaphorin I (SEQ ID NO:64), D1: Drosophila semaphorin I (SEQ ID NO:60), D2: Drosophila semaphorin II (SEQ ID NO:62), H3: Human semaphorin I (SEQ ID NO:54), V4: Vaccinia virus semaphorin IV (SEQ ID NO:56), V5: Variola virus (human small pox) semaphorin IV (SEQ ID NO:66); small case residues: conserved residues; underline: signal sequence; solid bar: transmembrane domain; double dashes: immunoglobulin domain.

```
G            MRAALVAVAALLWVVALHAAAWVNDVSPKMYVQFGEERVQR
T             MVVKILVWSICLIALCHAWMPDSSSKLINHFKSVESKS
D1
D2   MSLLQLSPLLALLLLLCSSVSETAADYENTWNFYYERPCCTGNDQGNNNYGKHGADHVRE
H3              MGWLTRIVCLFWGVLLTARANYQNGKNNVPRLKLSYKEMLESNNVIT
V4                      MMVLLHAVYSIVFVDVIIIKVQRYINDI

↓
G    f-Lg--nESHKDHfKLLeKDHNSlLvga--rNI---VYnISLRDLTEFTEQRiEwHSsGAHRELcY
T    fT-g--nATFPDHfIVLNQDETSILvgG--rNR---VYnLSIFDLSERKGGRiDwPSsDAHGQLcI
D1
D2   fNCgKLY---YRTfHMNeDRDT-lYvgaMDrVF---RVnLQNISSSNCNRDAiNLEPTRDDVVScV
H3   fN-gLAnSSSYHTfLLDeERSR-lYvgaKDHIFSFDLVnI-------KDFQKiVwPVsYTRRDEcK
V4   LTLDIFYLFKKMIPLLFILFYFANGIEWHKFETSEEIISTYLLDDV------LYTGVNGAVYTFSN
```

TABLE 1-continued

Deduced amino-acid sequence of semaphorin gene family.
Approximate position of enumerated peptide classes are indicated by
parenthetical (a) through (o); semaphorin domains are bounded by arrows;
G: grasshopper semaphorin I (SEQ ID NO:58), T: Tribolium semaphorin I
(SEQ ID NO:64), D1: Drosophila semaphorin I (SEQ ID NO:60), D2:
Drosophila semaphorin II (SEQ ID NO:62), H3: Human semaphorin I
(SEQ ID NO:54), V4: Vaccinia virus semaphorin IV (SEQ ID NO:56), V5:
Variola virus (human small pox) semaphorin IV (SEQ ID NO:66); small case
residues: conserved residues; underline: signal sequence; solid bar:
transmembrane domain; double dashes: immunoglobulin domain.

```
                 A
         F       V
     DDCQN-YIR(a)        ICGTN(b)
G   LkgkS-Eddcqn-yir--VlAKIDDDrVLIcgtnaYKpLcRHyALKd-----GDyVVeKEYEgRg----
T   LkgkT-Dddcqn-yir--ilYSSEPGKlVIcgtnSYKpLcRTyAFKE-----GKyLVeKEVEgIg----
D1       Eddcqn-yir--iMVVPSPGrlFvcgtnSFRpMcNTyIISd-----SNyTLeATKNgQA----
D2  SkgkSQIFdcKnHViQ--SMDQGD--rlYvcgtnaHNpKDYViYANL-----THLPRSEYVIgVgLGIA
H3  WAgkDILKEcAn--FiK--VlKAYNQTHlYAcgtGaFHpIcTYiEIGHPEDNIFKLENSHFENgRg----
V4  NkLNKTGLTNNn--yiTTSiKVEDADKDTLvcgtnNGNpKcWKiDGSd----------------------

S F                          A
     CPYDP(c)                  TVADFSG(d)
G   LcpFdpDh---------nstAIYSEgQ-------lysAtvadfsgTdpLiyrGpl------------
T   LcpyNpEh---------nstsVSYNgQ-------lFsAtvadfsgGdpLiyrEpQ------------
D1  VcpydpRh---------nstsVLADNE-------lysgtvadfsgSdpIiyrEpl------------
D2  KcpydpLD---------nstAIYVENGNPGGLPGlysgtNaEfTKAdTViFrTDlYNTSAKRLEYKF
H3  KSpydpKL---------LTAsLLIDgE-------lysgtAadfMgRdFAiFrT-1GHHHPIRTEQHD
V4  ----dpKhRGRGYAPYQnsKVTIISHNGcYLSDINIsKEGIKRWRRFDGPcGYDl------------
V5                                                   MIYl------------

N
      LNAPNFV(e)   (f)FFFRETA EYINCGK(g)        (h)DKGG
G   -rteRSdLkQ-lnapnfv-NTMEyNdFIFfffretaveyincgkaiysrvarvckHdkgg
T   -rteLSdLkQ-lnapnfv-NsVAygdYIFffYretaveyMncgkViysrvarvckDdkgg
D1  -QteQYdSLS-lnapnfv-SsFtQgdFvyfffretaveFincgkaiysrvarvckWdkgg
D2  KrtLKYdSkW-lDKpnfv-GsFDIgEYvyfffretaveyincgkaVysrriarvckKdVgg
H3  -SRWLNdpkF-ISaHLISEsdNPEDdkvyfffreNaIDGEHSgkaTHAriGQIckndFgg
V4  YTADNVIpkDGlRGA-fvDKdGty-dkvyILfTDtIG-SKRIVkIPy--iaQMcLndEgg
V5  YTADNVIpkDGlQGA-fvDKdGty-dkvyILfTVtIG-SKRIVkIPy--iaQMcLndECg SSY(i)      V
    PH      WTTFLKAR    NCSIPG(j)
G   phQF-GDrwtsflkSrlncsVpgDypfyf---neiqs---tsdIIegNyGGQVEkliygv
T   phQ-SRDrwtsflkarlncsipgEypfyf---Deiqs---tsdIvegRyNsDDsklIiygI
D1  phRF-RNrwtsflkSrlncsipgDypfyf---neiqs---AsNLvegQyGsMsskliygv
D2  KNLl-AhNwAtYlkarlncsiSgEFpfyf---neigs---VYQL-----PsDKsRF-FAT
H3  -hRSLVNKwttflkarllcsVpgPNGIDTHf-DeLq------dVFLMNFKDPKNPVVygv
V4  pSSlSShrwStflkVElEcDiDgRSYRQIIHSRTiKTDNDtILYvF--FDsPYsk-----
V5  pSSlSShrwStLlkVElEcDiDgRSYSQINHSKTiKQIMIRYYMYSLIVLFQVRIMYLFY V
      GSAVC(k)        NSNWLPV(l)     PRPGTCVND(m)
G   fttpVnSiGgsavcafsmKSiLESfDgPfkeqETMnsnwlAvPSLKvpeprpgQcvndsr
T   LttpVnAiGgsaIcayQmAdiLRVfEgsSfkHqETInsnwlpvPQNLvpeprpgQcvRdsr
D1  fNtpSnSiPgsavcafALQdiADTfEgQfkeqTGInsnwlpvNNAKvpDprpgScHndsr
D2  fttSTnGLIgsavcSfHINEiQAAfNgKfkeqSSSnsAwlpvLNSRvpeprpgTcvndTS
H3  fttSSnIFKgsavcMysmSdVRRVfLgPYAHRDGPnYQwVp--YQGRvpYprpgTc--PsK
V4  ---------saLcTYsmNTiKQSfSTSKLeg----------YTKQLpSpApgIcLPAGK
V5  EYH G   ---------TlpdVSVnfV-kShTlmdEAvpaFfTRpilIrIslQyrftKiAvdQqvRtPDgKAYdvLf
T   ---------IlpdKNVnfi-kThSlmED-vpaLfGKpVlVrVslQyrftAiTvdPqvKtINNQYLdvLY
D1  ---------AlpdPTLnfi-kThSlmdENvpaFfSQpilVrTsTIyrftQiAvdAqIKtPGgKTYdvIf
D2  ---------NlpdTVLnfi-RShPlmdKAvNHEHnNpVYYKRDlVFTK-LVVDKIRIDILNQEYI-vYY
H3  TFGGFDSTKDlpdDVITfA-rshPAmYNPvFPMNnRpiVIKTDVNyQftQiVvd-RvDAEDgQY-dvMf
V4  ---------VVpHTTFEViEKYNVlDdIIKP-LSnQpiFEGPSGVKWFDIKEKENEHREYRIYFIKENS G   igtdddgkvIkALnSAsFDSSDTvDSvVIeeLQvLPPGVpVKnlYVvr-------Mdg--d
T   igtdddgkvLkAvnIPKRHAKALLYRKYRTSVHPHGA--pVKQlKIAp------------G
D1  VgtdHgkIIkSvnAEsADSADKvTSvVIeeIDvLTKSEpIRnlEIvrTMQYDQPKdgSYd
D2  VgtNLgRIYkIvnGEsLSKLLDIFEvAPNeAIQVMEISQTR------------------
H3  IgtdVgTvLkVvSIPKETWY-DLEEvLLeeMTvFREPTAISA---------MELSTK
V4  iYSFdTkSKQTRSSQVDARLFSvMVTSKPLFIADIGIGVGMPQMKKILKM*
```

TABLE 1-continued

Deduced amino-acid sequence of semaphorin gene family.
Approximate position of enumerated peptide classes are indicated by
parenthetical (a) through (o); semaphorin domains are bounded by arrows;
G: grasshopper semaphorin I (SEQ ID NO:58), T: Tribolium semaphorin I
(SEQ ID NO:64), D1: Drosophila semaphorin I (SEQ ID NO:60), D2:
Drosophila semaphorin II (SEQ ID NO:62), H3: Human semaphorin I
(SEQ ID NO:54), V4: Vaccinia virus semaphorin IV (SEQ ID NO:56), V5:
Variola virus (human small pox) semaphorin IV (SEQ ID NO:66); small case
residues: conserved residues; underline: signal sequence; solid bar:
transmembrane domain; double dashes: immunoglobulin domain.

```
                      DPYCAWD(n)
G    dSklVVvSdDEiLAiKlhrcGSdkItNcRecvSlqdpycawdNVELKcTAVgSpDwSAG
T    YGkVVVvGKDEiRLANlNHcAS-k-tRcKDcvElqdpHcawdAKQNLcVSIDTVTSY--
D1   dGklIivTdSQVVAiQlhrcHNdkItScSecvAlqdpycawdKIAGKcRSHgApRw-LE
D2   -KSlYiGTdHRiKQiDlAMC-NRRYDNcFRcv--RdpycGwdKEANTcRPY--------
H3   QQQlYiGSTAGVAQLPlhrcDIYG-KAcAecCLARdpycawd--GSAcS---RYFPTAK G    KrRFIqNISLgEH-KAcGGRPQTEIVASPVPTQPTTKSSGDPVHSIHQAEFEpeiDNEiVI
T    -rFLIqdvVRgDD-NKcWsPQTDKkTVIKNKPSEVENEITNSIDEKDLDsSdpLiKTGLdD
D    ENYFYqNvATgQH-AAcPsGKINSkDANAGEGKGFRNDMDLLDSRRQ--sKdQeiIDNidK
D2   ELDLLqdvANETS-DIcDsSVLKKk
H3   RrTRRqdIRNgDPLTHcSDLHDNHH G    GVddSNVIPNTLAEINHAGSKLPSSQEKlPiytaetlTiaIvTSCLGAlVvgfIsgFLFs
T    DSdcDPVSENSIGGcAV--------RQQlViytaGtlHiVvvVVsiVGlFSWLYsgLSVF
D    NFEdD---------------------IINAQytVetlVMavLAGsiFSlLvgfFTgYFCG
                                                               ▬▬▬▬▬▬▬▬▬▬▬▬▬

G    rrcRGEDYTDMpFpdQRHQLNRLTEAGlNADsPYLPPCANnkAAInlvLNv-----PpkN
T    AKFHSd----SQypEAPFIEQHNHLERlsANQTGYLTPRAnk-AVnlvvKvSSSTPRpkK
D    rrcHKdEDDNLpypdTEYEYFEQRQNVNsFPsSCRIQQEPKLLPQVEEvTYAEPVLLpQP KKTYI(o)
G    AnGKNANsSAENKP----IQkktyi*
T    DnLDVSKDLNIASDGTLQKIkktyi*
D    PPPNKMHsPKNTLRKPPMHQMHQGPNSETLFQFHVTATTPSSRIVVATTSEHCVPTR*

D2            -----IVVTYg---QsVHlGcFVkIPEVlKNEQvTwYHHSKDKG
H3            GHSPEERIIygVENSsTFlEcSPkSQRAl----vYwQFQRRNEE
                                             ===============================

D2   rYeIRYSPTKYiETtERglVVVsVNEAdGgRyDchLGGSLLcSYNITVDAHRcTPPNKSN
H3   rKeE-IRVDDHiIRtDQglLLRSLQQKdSgNyLchAVEHGFIQTLLKVTLEVIDTEHLEE
     ========================================

D2   DYQKIYSDWcHEFEKYKTAMKSWEKKQGQcSTRQNFScNQHPNEIFRKPNV*
H3   LLHKDDDGDGSKTKEMSNSMTPSQKVWYRDFMQLINHPNLNTMDEFcEQVWKRDRKQRRQ

H3   RPGHTPGNSNKHLQENKKGRNRRTHEFERAPRSV*
```

---

What is claimed is:

1. A composition comprising an isolated polypeptide comprising the amino acid sequence of SEQ ID NO:54, and a physiologically acceptable carrier.

* * * * *

SEQUENCE LISTING (1) GENERAL INFORMATION:

(iii) NUMBER OF SEQUENCES: 100

(2) INFORMATION FOR SEQ ID NO: 1:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= SEQ01

-continued

/note= "Xaa denotes D or E at residue #1; Q,K,R,A
            or N at residue #3; and Y,F or V at residue #5"

(xi) SEQUENCE DESCRIPTION: SEQ ID NO: 1:

Xaa Cys Xaa Asn Xaa Ile
1               5

(2) INFORMATION FOR SEQ ID NO: 2:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= SEQ02
            /note= "Xaa denotes Q,K,R,A or N at residue #2;
            Y,F or V at residue #4; and R,K,Q or T at residue
            #6"

(xi) SEQUENCE DESCRIPTION: SEQ ID NO: 2:

Cys Xaa Asn Xaa Ile Xaa
1               5

(2) INFORMATION FOR SEQ ID NO: 3:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ03
            /note= "Xaa denotes N or G at residue #4; A,S or N
            at residue #5; Y,F,H or G at residue #6; and
            K,R,H,N or Q at residue #7"

(xi) SEQUENCE DESCRIPTION: SEQ ID NO: 3:

Cys Gly Thr Xaa Xaa Xaa Xaa
1               5

(2) INFORMATION FOR SEQ ID NO: 4:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ04
            /note= "Xaa denotes N or G at residue #4; and A,S
            or N at residue #5"

(xi) SEQUENCE DESCRIPTION: SEQ ID NO: 4:

Cys Gly Thr Xaa Xaa Xaa Xaa Pro
1               5

(2) INFORMATION FOR SEQ ID NO: 5:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..10
        (D) OTHER INFORMATION: /label= SEQ05
            /note= "Xaa denotes N or G at residue #4; and C or
            D at residue #10"

(xi) SEQUENCE DESCRIPTION: SEQ ID NO: 5:

```
Cys Gly Thr Xaa Xaa Xaa Xaa Pro Xaa Xaa
1               5                   10
```

(2) INFORMATION FOR SEQ ID NO: 6:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..13
        (D) OTHER INFORMATION: /label= SEQ06
            /note= "Xaa denotes C or D at residue #10; and Y
            or I at residue #13"

(xi) SEQUENCE DESCRIPTION: SEQ ID NO: 6:

```
Cys Gly Thr Xaa Xaa Xaa Xaa Pro Xaa Xaa Xaa Xaa Xaa
1               5                   10
```

(2) INFORMATION FOR SEQ ID NO: 7:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ07
            /note= "Xaa denotes R,I,Q or V at residue #1; G or
            A at residue #2; L,V or K at residue #3; C or S at
            residue #4; F or Y at residue #6; and D or N at
            residue #7"

(xi) SEQUENCE DESCRIPTION: SEQ ID NO: 7:

```
Xaa Xaa Xaa Xaa Pro Xaa Xaa
1               5
```

(2) INFORMATION FOR SEQ ID NO: 8:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
    (A) NAME/KEY: Peptide
    (B) LOCATION: 1..7
    (D) OTHER INFORMATION: /label= SEQ08
        /note= "Xaa denotes C or S at residue #1; F or Y
        at residue #3; D or N at residue #4; D,E,R or K at
        residue #6; and H,L or D at residue #7"

(xi) SEQUENCE DESCRIPTION: SEQ ID NO: 8:

Xaa Pro Xaa Xaa Pro Xaa Xaa
1               5

(2) INFORMATION FOR SEQ ID NO: 9:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= SEQ09
            /note= "Xaa denotes G or A at residue #3; C or S
            at residue #5; and D or N at residue #8"

(xi) SEQUENCE DESCRIPTION: SEQ ID NO: 9:

Gly Xaa Xaa Xaa Xaa Pro Tyr Xaa Pro
1               5

(2) INFORMATION FOR SEQ ID NO: 10:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ10
            /note= "Xaa denotes F or Y at residue #2; G or A
            at residue #4; and V,N or A at residue #6"

(xi) SEQUENCE DESCRIPTION: SEQ ID NO: 10:

Leu Xaa Ser Xaa Thr Xaa Ala
1               5

(2) INFORMATION FOR SEQ ID NO: 11:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= SEQ11
            /note= "Xaa denotes F or Y at residue #2; D or E
            at residue #8; and F or Y at residue #9"

(xi) SEQUENCE DESCRIPTION: SEQ ID NO: 11:

Leu Xaa Ser Xaa Thr Xaa Ala Xaa Xaa
1               5

(2) INFORMATION FOR SEQ ID NO: 12:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ12
            /note= "Xaa denotes F or Y at residue #1; G or A
            at residue #3; V,N or A at residue #5; D or E at
            residue #7; and F or Y at residue #8"

(xi) SEQUENCE DESCRIPTION: SEQ ID NO: 12:

Xaa Ser Xaa Thr Xaa Ala Xaa Xaa
1               5

(2) INFORMATION FOR SEQ ID NO: 13:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ13
            /note= "Xaa denotes N or D at residue #2; and A or
            K at residue #3"

(xi) SEQUENCE DESCRIPTION: SEQ ID NO: 13:

Leu Xaa Xaa Pro Asn Phe Val
1               5

(2) INFORMATION FOR SEQ ID NO: 14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

Phe Phe Phe Arg Glu
1               5

(2) INFORMATION FOR SEQ ID NO: 15:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide

```
    (ix) FEATURE:
         (A) NAME/KEY: Peptide
         (B) LOCATION: 1..6
         (D) OTHER INFORMATION: /label= SEQ15
             /note= "Xaa denotes F or Y at residue #3; and T or
             N at residue #6"

(xi) SEQUENCE DESCRIPTION: SEQ ID NO: 15:

Phe Phe Xaa Arg Glu Xaa
1               5

(2) INFORMATION FOR SEQ ID NO: 16:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..6
         (D) OTHER INFORMATION: /label= SEQ16
             /note= "Xaa denotes T or N at residue #5"

(xi) SEQUENCE DESCRIPTION: SEQ ID NO: 16:

Phe Phe Arg Glu Xaa Ala
1               5

(2) INFORMATION FOR SEQ ID NO: 17:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..6
         (D) OTHER INFORMATION: /label= SEQ17
             /note= "Xaa denotes F or Y at residue #2; and T or
             N at residue #5"

(xi) SEQUENCE DESCRIPTION: SEQ ID NO: 17:

Phe Xaa Arg Glu Xaa Ala
1               5

(2) INFORMATION FOR SEQ ID NO: 18:

(i) SEQUENCE CHARACTERISTICS:
         (A) LENGTH: 6 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..6
         (D) OTHER INFORMATION: /label= SEQ18
             /note= "Xaa denotes F or Y at residue #4"

(xi) SEQUENCE DESCRIPTION: SEQ ID NO: 18:

Tyr Phe Phe Xaa Arg Glu
1               5
```

(2) INFORMATION FOR SEQ ID NO: 19:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= SEQ19
            /note= "Xaa denotes F or Y at residue #1; and F or
            Y at residue #4"

(xi) SEQUENCE DESCRIPTION: SEQ ID NO: 19:

Xaa Phe Phe Xaa Arg Glu
    1               5

(2) INFORMATION FOR SEQ ID NO: 20:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ20
            /note= "Xaa denotes F or Y at residue #1; F or Y
            at residue #2; F or Y at residue #3; and T or N at
            residue #6"

(xi) SEQUENCE DESCRIPTION: SEQ ID NO: 20:

Xaa Xaa Xaa Arg Glu Xaa Ala
1               5

(2) INFORMATION FOR SEQ ID NO: 21:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ21
            /note= "Xaa denotes I or V at residue #1; F or Y
            at residue #2; F or Y at residue #4; and F or Y at
            residue #5"

(xi) SEQUENCE DESCRIPTION: SEQ ID NO: 21:

Xaa Xaa Phe Xaa Xaa Arg Glu
1               5

(2) INFORMATION FOR SEQ ID NO: 22:

(i) SEQUENCE CHARACTERISTICS:
        (A) LENGTH: 7 amino acids
        (B) TYPE: amino acid
        (C) STRANDEDNESS: single

```
            (D) TOPOLOGY: linear (ii) MOLECULE TYPE: peptide (ix) FEATURE:
            (A) NAME/KEY: Peptide
            (B) LOCATION: 1..7
            (D) OTHER INFORMATION: /label= SEQ22
                /note= "Xaa denotes K,F or Y at residue #2; F or Y
                at residue #4; F,Y,I or L at residue #5; F,Y,I or
                L at residue #6; and F or Y at residue #7"

(xi) SEQUENCE DESCRIPTION: SEQ ID NO: 22:

Asp Xaa Val Xaa Xaa Xaa Xaa
1               5

(2) INFORMATION FOR SEQ ID NO: 23:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..8
            (D) OTHER INFORMATION: /label= SEQ23
                /note= "Xaa denotes V or I at residue #1; F or Y
                at residue #2; F,Y,I or L at residue #3; F,Y,I or
                L at residue #4; R or T at residue #6; and T or N
                at residue #8"

(xi) SEQUENCE DESCRIPTION: SEQ ID NO: 23:

Xaa Xaa Xaa Xaa Phe Xaa Xaa Xaa
    1               5

(2) INFORMATION FOR SEQ ID NO: 24:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..8
            (D) OTHER INFORMATION: /label= SEQ24
                /note= "Xaa denotes V or I at residue #1; F or Y
                at residue #2; F,Y,I or L at residue #3; F,Y,I or
                L at residue #4; F or Y at residue #5; R or T at
                residue #6; E,D or V at residue #7; and T or N at
                residue #8"

(xi) SEQUENCE DESCRIPTION: SEQ ID NO: 24:

Xaa Xaa Xaa Xaa Xaa Xaa Xaa Xaa
1               5

(2) INFORMATION FOR SEQ ID NO: 25:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide
```

(ix) FEATURE:
            (A) NAME/KEY: Peptide
            (B) LOCATION: 1..7
            (D) OTHER INFORMATION: /label= SEQ25
                /note= "Xaa denotes F or Y at residue #2; and C or
                S at residue #5"

(xi) SEQUENCE DESCRIPTION: SEQ ID NO: 25:

Glu Xaa Ile Asn Xaa Gly Lys
1               5

(2) INFORMATION FOR SEQ ID NO: 26:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..7
            (D) OTHER INFORMATION: /label= SEQ26
                /note= "Xaa denotes F or Y at residue #1; and A,V
                or I at residue #7"

(xi) SEQUENCE DESCRIPTION: SEQ ID NO: 26:

Xaa Ile Asn Cys Gly Lys Xaa
1               5

(2) INFORMATION FOR SEQ ID NO: 27:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..7
            (D) OTHER INFORMATION: /label= SEQ27
                /note= "Xaa denotes V or I at residue #2; A or G
                at residue #3; R or Q at residue #4; and V or I at
                residue #5"

(xi) SEQUENCE DESCRIPTION: SEQ ID NO: 27:

Arg Xaa Xaa Xaa Xaa Cys Lys
1               5

(2) INFORMATION FOR SEQ ID NO: 28:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..9
            (D) OTHER INFORMATION: /label= SEQ28
                /note= "Xaa denotes V or I at residue #2; R or Q
                at residue #4; and V or I at residue #5"

(xi) SEQUENCE DESCRIPTION: SEQ ID NO: 28:

```
Arg Xaa Xaa Xaa Xaa Cys Xaa Xaa Asp
1               5
```

(2) INFORMATION FOR SEQ ID NO: 29:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..13
        (D) OTHER INFORMATION: /label= SEQ29
            /note= "Xaa denotes V,A or I at residue #3; and
            V,A or I at residue #8"

(xi) SEQUENCE DESCRIPTION: SEQ ID NO: 29:

```
Gly Lys Xaa Xaa Xaa Xaa Arg Xaa Xaa Xaa Xaa Cys Lys
1               5                   10
```

(2) INFORMATION FOR SEQ ID NO: 30:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ30
            /note= "Xaa denotes R,K or N at residue #1; T,A or
            S at residue #3; T,A or S at residue #4; F,Y or L
            at residue #5; and K or R at residue #7"

(xi) SEQUENCE DESCRIPTION: SEQ ID NO: 30:

```
Xaa Trp Xaa Xaa Xaa Leu Xaa
1               5
```

(2) INFORMATION FOR SEQ ID NO: 31:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ31
            /note= "Xaa denotes F or Y at residue #1; K or R
            at residue #3; A or S at residue #4; and N or I at
            residue #7"

(xi) SEQUENCE DESCRIPTION: SEQ ID NO: 31:

```
Xaa Leu Xaa Xaa Arg Leu Xaa Cys
1               5
```

(2) INFORMATION FOR SEQ ID NO: 32:

(i) SEQUENCE CHARACTERISTICS:
        (A) LENGTH: 6 amino acids (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..6
            (D) OTHER INFORMATION: /label= SEQ32
                /note= "Xaa denotes N or I at residue #1; I or V
                at residue #4; and P or S at residue #5"

(xi) SEQUENCE DESCRIPTION: SEQ ID NO: 32:

Xaa Cys Ser Xaa Xaa Gly
1               5

(2) INFORMATION FOR SEQ ID NO: 33:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..9
            (D) OTHER INFORMATION: /label= SEQ33
                /note= "Xaa denotes T,A or S at residue #2; T,A or
                S at residue #3; F,Y or L at residue #4; and
                A,S,V,I or L at residue #7"

(xi) SEQUENCE DESCRIPTION: SEQ ID NO: 33:

Trp Xaa Xaa Xaa Leu Lys Xaa Xaa Leu
1               5

(2) INFORMATION FOR SEQ ID NO: 34:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..11
            (D) OTHER INFORMATION: /label= SEQ34
                /note= "Xaa denotes T,A or S at residue #2; and
                T,A or S at residue #3"

(xi) SEQUENCE DESCRIPTION: SEQ ID NO: 34:

Trp Xaa Xaa Xaa Leu Lys Xaa Xaa Leu Xaa Cys
1               5                   10

(2) INFORMATION FOR SEQ ID NO: 35:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..11

(D) OTHER INFORMATION: /label= SEQ35
            /note= "Xaa denotes T or S at residue #3"

(xi) SEQUENCE DESCRIPTION: SEQ ID NO: 35:

Trp Xaa Xaa Xaa Leu Lys Xaa Xaa Leu Xaa Cys
1               5                   10

(2) INFORMATION FOR SEQ ID NO: 36:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ36
            /note= "Xaa denotes F or Y at residue #1; F or Y
            at residue #2; and N or D at residue #3"

(xi) SEQUENCE DESCRIPTION: SEQ ID NO: 36:

Xaa Xaa Xaa Glu Ile Gln Ser
1               5

(2) INFORMATION FOR SEQ ID NO: 37:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ37
            /note= "Xaa denotes F or Y at residue #1; F or Y
            at residue #3; F or Y at residue #4; F or Y at
            residue #5; and N or D at residue #6"

(xi) SEQUENCE DESCRIPTION: SEQ ID NO: 37:

Xaa Pro Xaa Xaa Xaa Xaa Glu
1               5

(2) INFORMATION FOR SEQ ID NO: 38:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ38
            /note= "Xaa denotes V,I or L at residue #4; and F
            or Y at residue #7"

(xi) SEQUENCE DESCRIPTION: SEQ ID NO: 38:

Gly Ser Ala Xaa Cys Xaa Xaa
1               5

(2) INFORMATION FOR SEQ ID NO: 39:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION: 1..8
      (D) OTHER INFORMATION: /label= SEQ39
         /note= "Xaa denotes V,I or L at residue #3; and F
         or Y at residue #6"

(xi) SEQUENCE DESCRIPTION: SEQ ID NO: 39:

Ser Ala Xaa Cys Xaa Xaa Xaa Met
1          5

(2) INFORMATION FOR SEQ ID NO: 40:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION: 1..7
      (D) OTHER INFORMATION: /label= SEQ40
         /note= "Xaa denotes N or A at residue #3; and P or
         A at residue #6"

(xi) SEQUENCE DESCRIPTION: SEQ ID NO: 40:

Asn Ser Xaa Trp Leu Xaa Val
1          5

(2) INFORMATION FOR SEQ ID NO: 41:

(i) SEQUENCE CHARACTERISTICS:
      (A) LENGTH: 7 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide
      (B) LOCATION: 1..7
      (D) OTHER INFORMATION: /label= SEQ41
         /note= "Xaa denotes V,L or I at residue #1; and
         E,D,Y,S or F at residue #3"

(xi) SEQUENCE DESCRIPTION: SEQ ID NO: 41:

Xaa Pro Xaa Pro Arg Pro Gly
1          5

(2) INFORMATION FOR SEQ ID NO: 42:

(i) SEQUENCE CHARACTERISTICS:
      (A) LENGTH: 9 amino acids
      (B) TYPE: amino acid
      (C) STRANDEDNESS: single
      (D) TOPOLOGY: linear (ii) MOLECULE TYPE: peptide (ix) FEATURE:
            (A) NAME/KEY: Peptide
            (B) LOCATION: 1..9
            (D) OTHER INFORMATION: /label= SEQ42
                /note= "Xaa denotes V,L or I at residue #1; and R
                or A at residue #5"

(xi) SEQUENCE DESCRIPTION: SEQ ID NO: 42:

Xaa Pro Xaa Pro Xaa Pro Gly Xaa Cys
1               5

(2) INFORMATION FOR SEQ ID NO: 43:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ43
            /note= "Xaa denotes E,D,Y,S or F at residue #2;
            and T,Q or S at residue #7"

(xi) SEQUENCE DESCRIPTION: SEQ ID NO: 43:

Pro Xaa Pro Arg Pro Gly Xaa Cys
1               5

(2) INFORMATION FOR SEQ ID NO: 44:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= SEQ44
            /note= "Xaa denotes H,F or Y at residue #3; and A
            or G at residue #5"

(xi) SEQUENCE DESCRIPTION: SEQ ID NO: 44:

Asp Pro Xaa Cys Xaa Trp
1               5

(2) INFORMATION FOR SEQ ID NO: 45:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..6
        (D) OTHER INFORMATION: /label= SEQ45
            /note= "Xaa denotes H,F or Y at residue #2; and A
            or G at residue #4"

(xi) SEQUENCE DESCRIPTION: SEQ ID NO: 45:

Pro Xaa Cys Xaa Trp Asp (2) INFORMATION FOR SEQ ID NO: 46:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ46
            /note= "Xaa denotes A or G at residue #5"

(xi) SEQUENCE DESCRIPTION: SEQ ID NO: 46:

Asp Pro Xaa Cys Xaa Trp Asp
1               5

(2) INFORMATION FOR SEQ ID NO: 47:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 47:

Cys Xaa Xaa Xaa Xaa Asp Pro Xaa Cys Xaa Trp Asp
1               5                   10

(2) INFORMATION FOR SEQ ID NO: 48:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 48:

Cys Xaa Xaa Xaa Asp Pro Xaa Cys Xaa Trp Asp
1               5                   10

(2) INFORMATION FOR SEQ ID NO: 49:

(i) SEQUENCE CHARACTERISTICS:
        (A) LENGTH: 10 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 49:

Cys Xaa Xaa Asp Pro Xaa Cys Xaa Trp Asp
1               5                   10

(2) INFORMATION FOR SEQ ID NO: 50:

(i) SEQUENCE CHARACTERISTICS:
        (A) LENGTH: 15 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 50:

Cys Xaa Xaa Cys Xaa Xaa Xaa Xaa Asp Xaa Xaa Cys Xaa Trp Asp
1               5                   10                  15

(2) INFORMATION FOR SEQ ID NO: 51:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 51:

Cys Xaa Xaa Cys Xaa Xaa Xaa Asp Xaa Xaa Cys Xaa Trp Asp
1               5                   10

(2) INFORMATION FOR SEQ ID NO: 52:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 52:

Cys Xaa Xaa Cys Xaa Xaa Asp Xaa Xaa Cys Xaa Trp Asp
1               5                   10

(2) INFORMATION FOR SEQ ID NO: 53:

(i) SEQUENCE CHARACTERISTICS:
        (A) LENGTH: 2601 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 16..2331

(xi) SEQUENCE DESCRIPTION: SEQ ID NO: 53:

```
GGAATTCCCT GCAGC ATG GGC TGG TTA ACT AGG ATT GTC TGT CTT TTC TGG         51
               Met Gly Trp Leu Thr Arg Ile Val Cys Leu Phe Trp
                 1               5                  10

GGA GTA TTA CTT ACA GCA AGA GCA AAC TAT CAG AAT GGG AAG AAC AAT          99
Gly Val Leu Leu Thr Ala Arg Ala Asn Tyr Gln Asn Gly Lys Asn Asn
             15                  20                  25

GTG CCA AGG CTG AAA TTA TCC TAC AAA GAA ATG TTG GAA TCC AAC AAT         147
Val Pro Arg Leu Lys Leu Ser Tyr Lys Glu Met Leu Glu Ser Asn Asn
         30                  35                  40

GTG ATC ACT TTC AAT GGC TTG GCC AAC AGC TCC AGT TAT CAT ACC TTC         195
Val Ile Thr Phe Asn Gly Leu Ala Asn Ser Ser Ser Tyr His Thr Phe
 45                  50                  55                  60

CTT TTG GAT GAG GAA CGG AGT AGG CTG TAT GTT GGA GCA AAG GAT CAC         243
Leu Leu Asp Glu Glu Arg Ser Arg Leu Tyr Val Gly Ala Lys Asp His
                 65                  70                  75

ATA TTT TCA TTC GAC CTG GTT AAT ATC AAG GAT TTT CAA AAG ATT GTG         291
```

-continued

```
                Ile Phe Ser Phe Asp Leu Val Asn Ile Lys Asp Phe Gln Lys Ile Val
                                80                  85                  90

TGG CCA GTA TCT TAC ACC AGA AGA GAT GAA TGC AAG TGG GCT GGA AAA                     339
Trp Pro Val Ser Tyr Thr Arg Arg Asp Glu Cys Lys Trp Ala Gly Lys
            95                  100                 105

GAC ATC CTG AAA GAA TGT GCT AAT TTC ATC AAG GTA CTT AAG GCA TAT                     387
Asp Ile Leu Lys Glu Cys Ala Asn Phe Ile Lys Val Leu Lys Ala Tyr
        110                 115                 120

AAT CAG ACT CAC TTG TAC GCC TGT GGA ACG GGG GCT TTT CAT CCA ATT                     435
Asn Gln Thr His Leu Tyr Ala Cys Gly Thr Gly Ala Phe His Pro Ile
125                 130                 135                 140

TGC ACC TAC ATT GAA ATT GGA CAT CAT CCT GAG GAC AAT ATT TTT AAG                     483
Cys Thr Tyr Ile Glu Ile Gly His His Pro Glu Asp Asn Ile Phe Lys
                145                 150                 155

CTG GAG AAC TCA CAT TTT GAA AAC GGC CGT GGG AAG AGT CCA TAT GAC                     531
Leu Glu Asn Ser His Phe Glu Asn Gly Arg Gly Lys Ser Pro Tyr Asp
            160                 165                 170

CCT AAG CTG CTG ACA GCA TCC CTT TTA ATA GAT GGA GAA TTA TAC TCT                     579
Pro Lys Leu Leu Thr Ala Ser Leu Leu Ile Asp Gly Glu Leu Tyr Ser
        175                 180                 185

GGA ACT GCA GCT GAT TTT ATG GGG CGA GAC TTT GCT ATC TTC CGA ACT                     627
Gly Thr Ala Ala Asp Phe Met Gly Arg Asp Phe Ala Ile Phe Arg Thr
190                 195                 200

CTT GGG CAC CAC CAC CCA ATC AGG ACA GAG CAG CAT GAT TCC AGG TGG                     675
Leu Gly His His His Pro Ile Arg Thr Glu Gln His Asp Ser Arg Trp
205                 210                 215                 220

CTC AAT GAT CCA AAG TTC ATT AGT GCC CAC CTC ATC TCA GAG AGT GAC                     723
Leu Asn Asp Pro Lys Phe Ile Ser Ala His Leu Ile Ser Glu Ser Asp
                225                 230                 235

AAT CCT GAA GAT GAC AAA GTA TAC TTT TTC TTC CGT GAA AAT GCA ATA                     771
Asn Pro Glu Asp Asp Lys Val Tyr Phe Phe Phe Arg Glu Asn Ala Ile
            240                 245                 250

GAT GGA GAA CAC TCT GGA AAA GCT ACT CAC GCT AGA ATA GGT CAG ATA                     819
Asp Gly Glu His Ser Gly Lys Ala Thr His Ala Arg Ile Gly Gln Ile
        255                 260                 265

TGC AAG AAT GAC TTT GGA GGG CAC AGA AGT CTG GTG AAT AAA TGG ACA                     867
Cys Lys Asn Asp Phe Gly Gly His Arg Ser Leu Val Asn Lys Trp Thr
270                 275                 280

ACA TTC CTC AAA GCT CGT CTG ATT TGC TCA GTG CCA GGT CCA AAT GGC                     915
Thr Phe Leu Lys Ala Arg Leu Ile Cys Ser Val Pro Gly Pro Asn Gly
285                 290                 295                 300

ATT GAC ACT CAT TTT GAT GAA CTG CAG GAT GTA TTC CTA ATG AAC TTT                     963
Ile Asp Thr His Phe Asp Glu Leu Gln Asp Val Phe Leu Met Asn Phe
                305                 310                 315

AAA GAT CCT AAA AAT CCA GTT GTA TAT GGA GTG TTT ACG ACT TCC AGT                    1011
Lys Asp Pro Lys Asn Pro Val Val Tyr Gly Val Phe Thr Thr Ser Ser
            320                 325                 330

AAC ATT TTC AAG GGA TCA GCC GTG TGT ATG TAT AGC ATG AGT GAT GTG                    1059
Asn Ile Phe Lys Gly Ser Ala Val Cys Met Tyr Ser Met Ser Asp Val
        335                 340                 345

AGA AGG GTG TTC CTT GGT CCA TAT GCC CAC AGG GAT GGA CCC AAC TAT                    1107
Arg Arg Val Phe Leu Gly Pro Tyr Ala His Arg Asp Gly Pro Asn Tyr
350                 355                 360

CAA TGG GTG CCT TAT CAA GGA AGA GTC CCC TAT CCA CGG CCA GGA ACT                    1155
Gln Trp Val Pro Tyr Gln Gly Arg Val Pro Tyr Pro Arg Pro Gly Thr
365                 370                 375                 380

TGT CCC AGC AAA ACA TTT GGT GGT TTT GAC TCT ACA AAG GAC CTT CCT                    1203
Cys Pro Ser Lys Thr Phe Gly Gly Phe Asp Ser Thr Lys Asp Leu Pro
                385                 390                 395
```

```
                                                     -continued
GAT GAT GTT ATA ACC TTT GCA AGA AGT CAT CCA GCC ATG TAC AAT CCA    1251
Asp Asp Val Ile Thr Phe Ala Arg Ser His Pro Ala Met Tyr Asn Pro
            400                 405                 410

GTG TTT CCT ATG AAC AAT CGC CCA ATA GTG ATC AAA ACG GAT GTA AAT    1299
Val Phe Pro Met Asn Asn Arg Pro Ile Val Ile Lys Thr Asp Val Asn
        415                 420                 425

TAT CAA TTT ACA CAA ATT GTC GTA GAC CGA GTG GAT GCA GAA GAT GGA    1347
Tyr Gln Phe Thr Gln Ile Val Val Asp Arg Val Asp Ala Glu Asp Gly
    430                 435                 440

CAG TAT GAT GTT ATG TTT ATC GGA ACA GAT GTT GGG ACC GTT CTT AAA    1395
Gln Tyr Asp Val Met Phe Ile Gly Thr Asp Val Gly Thr Val Leu Lys
445                 450                 455                 460

GTA GTT TCA ATT CCT AAG GAG ACT TGG TAT GAT TTA GAA GAG GTT CTG    1443
Val Val Ser Ile Pro Lys Glu Thr Trp Tyr Asp Leu Glu Glu Val Leu
                465                 470                 475

CTG GAA GAA ATG ACA GTT TTT CGG GAA CCG ACT GCT ATT TCA GCA ATG    1491
Leu Glu Glu Met Thr Val Phe Arg Glu Pro Thr Ala Ile Ser Ala Met
            480                 485                 490

GAG CTT TCC ACT AAG CAG CAA CAA CTA TAT ATT GGT TCA ACG GCT GGG    1539
Glu Leu Ser Thr Lys Gln Gln Gln Leu Tyr Ile Gly Ser Thr Ala Gly
        495                 500                 505

GTT GCC CAG CTC CCT TTA CAC CGG TGT GAT ATT TAC GGG AAA GCG TGT    1587
Val Ala Gln Leu Pro Leu His Arg Cys Asp Ile Tyr Gly Lys Ala Cys
    510                 515                 520

GCT GAG TGT TGC CTC GCC CGA GAC CCT TAC TGT GCT TGG GAT GGT TCT    1635
Ala Glu Cys Cys Leu Ala Arg Asp Pro Tyr Cys Ala Trp Asp Gly Ser
525                 530                 535                 540

GCA TGT TCT CGC TAT TTT CCC ACT GCA AAG AGA CGC ACA AGA CGA CAA    1683
Ala Cys Ser Arg Tyr Phe Pro Thr Ala Lys Arg Arg Thr Arg Arg Gln
                545                 550                 555

GAT ATA AGA AAT GGA GAC CCA CTG ACT CAC TGT TCA GAC TTA CAC CAT    1731
Asp Ile Arg Asn Gly Asp Pro Leu Thr His Cys Ser Asp Leu His His
            560                 565                 570

GAT AAT CAC CAT GGC CAC AGC CCT GAA GAG AGA ATC ATC TAT GGT GTA    1779
Asp Asn His His Gly His Ser Pro Glu Glu Arg Ile Ile Tyr Gly Val
        575                 580                 585

GAG AAT AGT AGC ACA TTT TTG GAA TGC AGT CCG AAG TCG CAG AGA GCG    1827
Glu Asn Ser Ser Thr Phe Leu Glu Cys Ser Pro Lys Ser Gln Arg Ala
    590                 595                 600

CTG GTC TAT TGG CAA TTC CAG AGG CGA AAT GAA GAG CGA AAA GAA GAG    1875
Leu Val Tyr Trp Gln Phe Gln Arg Arg Asn Glu Glu Arg Lys Glu Glu
605                 610                 615                 620

ATC AGA GTG GAT GAT CAT ATC ATC AGG ACA GAT CAA GGC CTT CTG CTA    1923
Ile Arg Val Asp Asp His Ile Ile Arg Thr Asp Gln Gly Leu Leu Leu
                625                 630                 635

CGT AGT CTA CAA CAG AAG GAT TCA GGC AAT TAC CTC TGC CAT GCG GTG    1971
Arg Ser Leu Gln Gln Lys Asp Ser Gly Asn Tyr Leu Cys His Ala Val
            640                 645                 650

GAA CAT GGG TTC ATA CAA ACT CTT CTT AAG GTA ACC CTG GAA GTC ATT    2019
Glu His Gly Phe Ile Gln Thr Leu Leu Lys Val Thr Leu Glu Val Ile
        655                 660                 665

GAC ACA GAG CAT TTG GAA GAA CTT CTT CAT AAA GAT GAT GAT GGA GAT    2067
Asp Thr Glu His Leu Glu Glu Leu Leu His Lys Asp Asp Asp Gly Asp
    670                 675                 680

GGC TCT AAG ACC AAA GAA ATG TCC AAT AGC ATG ACA CCT AGC CAG AAG    2115
Gly Ser Lys Thr Lys Glu Met Ser Asn Ser Met Thr Pro Ser Gln Lys
685                 690                 695                 700

GTC TGG TAC AGA GAC TTC ATG CAG CTC ATC AAC CAC CCC AAT CTC AAC    2163
Val Trp Tyr Arg Asp Phe Met Gln Leu Ile Asn His Pro Asn Leu Asn
                705                 710                 715
```

-continued

```
ACG ATG GAT GAG TTC TGT GAA CAA GTT TGG AAA AGG GAC CGA AAA CAA      2211
Thr Met Asp Glu Phe Cys Glu Gln Val Trp Lys Arg Asp Arg Lys Gln
        720                 725                 730

CGT CGG CAA AGG CCA GGA CAT ACC CCA GGG AAC AGT AAC AAA TGG AAG      2259
Arg Arg Gln Arg Pro Gly His Thr Pro Gly Asn Ser Asn Lys Trp Lys
            735                 740                 745

CAC TTA CAA GAA AAT AAG AAA GGT AGA AAC AGG AGG ACC CAC GAA TTT      2307
His Leu Gln Glu Asn Lys Lys Gly Arg Asn Arg Arg Thr His Glu Phe
        750                 755                 760

GAG AGG GCA CCC AGG AGT GTC TGAGCTGCAT TACCTCTAGA AACCTCAAAC         2358
Glu Arg Ala Pro Arg Ser Val
765                 770

AAGTAGAAAC TTGCCTAGAC AATAACTGGA AAAACAAATG CAATATACAT GAACTTTTTT    2418

CATGGCATTA TGTGGATGTT TACAATGGTG GGAAATTCAG CTGAGTTCCA CCAATTATAA    2478

ATTAAATCCA TGAGTAACTT TCCTAATAGG CTTTTTTTTC CTAATACCAC CGGGTTAAAA    2538

GTAAGAGACA GCTGAACCCT CGTGGAGCCA TTCATACAGG TCCCTATTTA AGGAACGGAA    2598

TTC                                                                 2601
```

(2) INFORMATION FOR SEQ ID NO: 54:

(i) SEQUENCE CHARACTERISTICS:
        (A) LENGTH: 771 amino acids
        (B) TYPE: amino acid
        (D) TOPOLOGY: linear (ii) MOLECULE TYPE: protein (xi) SEQUENCE DESCRIPTION: SEQ ID NO: 54:

```
Met Gly Trp Leu Thr Arg Ile Val Cys Leu Phe Trp Gly Val Leu Leu
 1               5                  10                  15

Thr Ala Arg Ala Asn Tyr Gln Asn Gly Lys Asn Asn Val Pro Arg Leu
            20                  25                  30

Lys Leu Ser Tyr Lys Glu Met Leu Glu Ser Asn Asn Val Ile Thr Phe
        35                  40                  45

Asn Gly Leu Ala Asn Ser Ser Ser Tyr His Thr Phe Leu Leu Asp Glu
    50                  55                  60

Glu Arg Ser Arg Leu Tyr Val Gly Ala Lys Asp His Ile Phe Ser Phe
65                  70                  75                  80

Asp Leu Val Asn Ile Lys Asp Phe Gln Lys Ile Val Trp Pro Val Ser
                85                  90                  95

Tyr Thr Arg Arg Asp Glu Cys Lys Trp Ala Gly Lys Asp Ile Leu Lys
            100                 105                 110

Glu Cys Ala Asn Phe Ile Lys Val Leu Lys Ala Tyr Asn Gln Thr His
        115                 120                 125

Leu Tyr Ala Cys Gly Thr Gly Ala Phe His Pro Ile Cys Thr Tyr Ile
    130                 135                 140

Glu Ile Gly His His Pro Glu Asp Asn Ile Phe Lys Leu Glu Asn Ser
145                 150                 155                 160

His Phe Glu Asn Gly Arg Gly Lys Ser Pro Tyr Asp Pro Lys Leu Leu
                165                 170                 175

Thr Ala Ser Leu Leu Ile Asp Gly Glu Leu Tyr Ser Gly Thr Ala Ala
            180                 185                 190

Asp Phe Met Gly Arg Asp Phe Ala Ile Phe Arg Thr Leu Gly His His
        195                 200                 205

His Pro Ile Arg Thr Glu Gln His Asp Ser Arg Trp Leu Asn Asp Pro
```

-continued

```
                210                 215                 220
Lys Phe Ile Ser Ala His Leu Ile Ser Glu Ser Asp Asn Pro Glu Asp
225                 230                 235                 240

Asp Lys Val Tyr Phe Phe Arg Glu Asn Ala Ile Asp Gly Glu His
                245                 250                 255

Ser Gly Lys Ala Thr His Ala Arg Ile Gly Gln Ile Cys Lys Asn Asp
                260                 265                 270

Phe Gly Gly His Arg Ser Leu Val Asn Lys Trp Thr Thr Phe Leu Lys
                275                 280                 285

Ala Arg Leu Ile Cys Ser Val Pro Gly Pro Asn Gly Ile Asp Thr His
290                 295                 300

Phe Asp Glu Leu Gln Asp Val Phe Leu Met Asn Phe Lys Asp Pro Lys
305                 310                 315                 320

Asn Pro Val Val Tyr Gly Val Phe Thr Thr Ser Ser Asn Ile Phe Lys
                325                 330                 335

Gly Ser Ala Val Cys Met Tyr Ser Met Ser Asp Val Arg Arg Val Phe
                340                 345                 350

Leu Gly Pro Tyr Ala His Arg Asp Gly Pro Asn Tyr Gln Trp Val Pro
                355                 360                 365

Tyr Gln Gly Arg Val Pro Tyr Pro Arg Pro Gly Thr Cys Pro Ser Lys
370                 375                 380

Thr Phe Gly Gly Phe Asp Ser Thr Lys Asp Leu Pro Asp Asp Val Ile
385                 390                 395                 400

Thr Phe Ala Arg Ser His Pro Ala Met Tyr Asn Pro Val Phe Pro Met
                405                 410                 415

Asn Asn Arg Pro Ile Val Ile Lys Thr Asp Val Asn Tyr Gln Phe Thr
                420                 425                 430

Gln Ile Val Val Asp Arg Val Asp Ala Glu Asp Gly Gln Tyr Asp Val
                435                 440                 445

Met Phe Ile Gly Thr Asp Val Gly Thr Val Leu Lys Val Val Ser Ile
                450                 455                 460

Pro Lys Glu Thr Trp Tyr Asp Leu Glu Glu Val Leu Leu Glu Glu Met
465                 470                 475                 480

Thr Val Phe Arg Glu Pro Thr Ala Ile Ser Ala Met Glu Leu Ser Thr
                485                 490                 495

Lys Gln Gln Gln Leu Tyr Ile Gly Ser Thr Ala Gly Val Ala Gln Leu
                500                 505                 510

Pro Leu His Arg Cys Asp Ile Tyr Gly Lys Ala Cys Ala Glu Cys Cys
                515                 520                 525

Leu Ala Arg Asp Pro Tyr Cys Ala Trp Asp Gly Ser Ala Cys Ser Arg
530                 535                 540

Tyr Phe Pro Thr Ala Lys Arg Arg Thr Arg Arg Gln Asp Ile Arg Asn
545                 550                 555                 560

Gly Asp Pro Leu Thr His Cys Ser Asp Leu His Asp Asn His His
                565                 570                 575

Gly His Ser Pro Glu Glu Arg Ile Ile Tyr Gly Val Glu Asn Ser Ser
                580                 585                 590

Thr Phe Leu Glu Cys Ser Pro Lys Ser Gln Arg Ala Leu Val Tyr Trp
                595                 600                 605

Gln Phe Gln Arg Arg Asn Glu Glu Arg Lys Glu Glu Ile Arg Val Asp
                610                 615                 620

Asp His Ile Ile Arg Thr Asp Gln Gly Leu Leu Leu Arg Ser Leu Gln
625                 630                 635                 640
```

```
Gln Lys Asp Ser Gly Asn Tyr Leu Cys His Ala Val Glu His Gly Phe
            645                 650                 655

Ile Gln Thr Leu Leu Lys Val Thr Leu Glu Val Ile Asp Thr Glu His
            660                 665                 670

Leu Glu Glu Leu Leu His Lys Asp Asp Gly Asp Gly Ser Lys Thr
            675                 680                 685

Lys Glu Met Ser Asn Ser Met Thr Pro Ser Gln Lys Val Trp Tyr Arg
690                 695                 700

Asp Phe Met Gln Leu Ile Asn His Pro Asn Leu Asn Thr Met Asp Glu
705                 710                 715                 720

Phe Cys Glu Gln Val Trp Lys Arg Asp Arg Lys Gln Arg Arg Gln Arg
                725                 730                 735

Pro Gly His Thr Pro Gly Asn Ser Asn Lys Trp Lys His Leu Gln Glu
            740                 745                 750

Asn Lys Lys Gly Arg Asn Arg Arg Thr His Glu Phe Glu Arg Ala Pro
            755                 760                 765

Arg Ser Val
    770
```

(2) INFORMATION FOR SEQ ID NO: 55:

(i) SEQUENCE CHARACTERISTICS:
        (A) LENGTH: 1332 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 7..1329

(xi) SEQUENCE DESCRIPTION: SEQ ID NO: 55:

```
GGAATA ATG ATG GTA TTA TTA CAT GCT GTA TAC TCT ATA GTC TTT GTA          48
       Met Met Val Leu Leu His Ala Val Tyr Ser Ile Val Phe Val
         1               5                  10

GAT GTT ATA ATC ATA AAA GTA CAG AGG TAT ATC AAC GAT ATT CTA ACT         96
Asp Val Ile Ile Ile Lys Val Gln Arg Tyr Ile Asn Asp Ile Leu Thr
15                  20                  25                  30

CTT GAC ATT TTT TAT TTA TTT AAA ATG ATA CCT TTG TTA TTT ATT TTA        144
Leu Asp Ile Phe Tyr Leu Phe Lys Met Ile Pro Leu Leu Phe Ile Leu
                35                  40                  45

TTC TAT TTT GCT AAC GGT ATC GAA TGG CAT AAG TTT GAA ACG AGT GAA        192
Phe Tyr Phe Ala Asn Gly Ile Glu Trp His Lys Phe Glu Thr Ser Glu
            50                  55                  60

GAA ATA ATT TCT ACT TAC TTA TTA GAC GAC GTA TTA TAC ACG GGT GTT        240
Glu Ile Ile Ser Thr Tyr Leu Leu Asp Asp Val Leu Tyr Thr Gly Val
            65                  70                  75

AAT GGG GCG GTA TAC ACA TTT TCA AAT AAT AAA CTA AAC AAA ACT GGT        288
Asn Gly Ala Val Tyr Thr Phe Ser Asn Asn Lys Leu Asn Lys Thr Gly
    80                  85                  90

TTA ACT AAT AAT AAT TAT ATA ACA ACA TCT ATA AAA GTA GAG GAT GCG        336
Leu Thr Asn Asn Asn Tyr Ile Thr Thr Ser Ile Lys Val Glu Asp Ala
 95                 100                 105                 110

GAT AAG GAT ACA TTA GTA TGC GGA ACC AAT AAC GGA AAT CCC AAA TGT        384
Asp Lys Asp Thr Leu Val Cys Gly Thr Asn Asn Gly Asn Pro Lys Cys
                115                 120                 125

TGG AAA ATA GAC GGT TCA GAC GAC CCA AAA CAT AGA GGT AGA GGA TAC        432
Trp Lys Ile Asp Gly Ser Asp Asp Pro Lys His Arg Gly Arg Gly Tyr
```

```
                 130                 135                 140
GCT CCT TAT CAA AAT AGC AAA GTA ACG ATA ATC AGT CAC AAC GGA TGT        480
Ala Pro Tyr Gln Asn Ser Lys Val Thr Ile Ile Ser His Asn Gly Cys
        145                 150                 155

GTA CTA TCT GAC ATA AAC ATA TCA AAA GAA GGA ATT AAA CGA TGG AGA        528
Val Leu Ser Asp Ile Asn Ile Ser Lys Glu Gly Ile Lys Arg Trp Arg
        160                 165                 170

AGA TTT GAC GGA CCA TGT GGT TAT GAT TTA TAC ACG GCG GAT AAC GTA        576
Arg Phe Asp Gly Pro Cys Gly Tyr Asp Leu Tyr Thr Ala Asp Asn Val
175                 180                 185                 190

ATT CCA AAA GAT GGT TTA CGA GGA GCA TTC GTC GAT AAA GAT GGT ACT        624
Ile Pro Lys Asp Gly Leu Arg Gly Ala Phe Val Asp Lys Asp Gly Thr
                195                 200                 205

TAT GAC AAA GTT TAC ATT CTT TTC ACT GAT ACT ATC GGC TCA AAG AGA        672
Tyr Asp Lys Val Tyr Ile Leu Phe Thr Asp Thr Ile Gly Ser Lys Arg
        210                 215                 220

ATT GTC AAA ATT CCG TAT ATA GCA CAA ATG TGC CTA AAC GAC GAA GGT        720
Ile Val Lys Ile Pro Tyr Ile Ala Gln Met Cys Leu Asn Asp Glu Gly
        225                 230                 235

GGT CCA TCA TCA TTG TCT AGT CAT AGA TGG TCG ACG TTT CTC AAA GTC        768
Gly Pro Ser Ser Leu Ser Ser His Arg Trp Ser Thr Phe Leu Lys Val
        240                 245                 250

GAA TTA GAA TGT GAT ATC GAC GGA AGA AGT TAT AGA CAA ATT ATT CAT        816
Glu Leu Glu Cys Asp Ile Asp Gly Arg Ser Tyr Arg Gln Ile Ile His
255                 260                 265                 270

TCT AGA ACT ATA AAA ACA GAT AAT GAT ACG ATA CTA TAT GTA TTC TTC        864
Ser Arg Thr Ile Lys Thr Asp Asn Asp Thr Ile Leu Tyr Val Phe Phe
                275                 280                 285

GAT AGT CCT TAT TCC AAG TCC GCA TTA TGT ACC TAT TCT ATG AAT ACC        912
Asp Ser Pro Tyr Ser Lys Ser Ala Leu Cys Thr Tyr Ser Met Asn Thr
        290                 295                 300

ATT AAA CAA TCT TTT TCT ACG TCA AAA TTG GAA GGA TAT ACA AAG CAA        960
Ile Lys Gln Ser Phe Ser Thr Ser Lys Leu Glu Gly Tyr Thr Lys Gln
        305                 310                 315

TTG CCG TCG CCA GCC TCT GGT ATA TGT CTA CCA GCT GGA AAA GTT GTT       1008
Leu Pro Ser Pro Ala Ser Gly Ile Cys Leu Pro Ala Gly Lys Val Val
        320                 325                 330

CCA CAT ACC ACG TTT GAA GTC ATA GAA AAA TAT AAT GTA CTA GAT GAT       1056
Pro His Thr Thr Phe Glu Val Ile Glu Lys Tyr Asn Val Leu Asp Asp
335                 340                 345                 350

ATT ATA AAG CCT TTA TCT AAC CAA CCT ATC TTC GAA GGA CCG TCT GGT       1104
Ile Ile Lys Pro Leu Ser Asn Gln Pro Ile Phe Glu Gly Pro Ser Gly
                355                 360                 365

GTT AAA TGG TTC GAT ATA AAG GAG AAG GAA AAT GAA CAT CGG GAA TAT       1152
Val Lys Trp Phe Asp Ile Lys Glu Lys Glu Asn Glu His Arg Glu Tyr
        370                 375                 380

AGA ATA TAC TTC ATA AAA GAA AAT TCT ATA TAT TCG TTC GAT ACA AAA       1200
Arg Ile Tyr Phe Ile Lys Glu Asn Ser Ile Tyr Ser Phe Asp Thr Lys
        385                 390                 395

TCT AAA CAA ACT CGT AGC TCG CAA GTC GAT GCG CGA CTA TTT TCA GTA       1248
Ser Lys Gln Thr Arg Ser Ser Gln Val Asp Ala Arg Leu Phe Ser Val
        400                 405                 410

ATG GTA ACT TCG AAA CCG TTA TTT ATA GCA GAT ATA GGG ATA GGA GTA       1296
Met Val Thr Ser Lys Pro Leu Phe Ile Ala Asp Ile Gly Ile Gly Val
415                 420                 425                 430

GGA ATG CCA CAA ATG AAA AAA ATA CTT AAA ATG TAA                       1332
Gly Met Pro Gln Met Lys Lys Ile Leu Lys Met
                435                 440
```

(2) INFORMATION FOR SEQ ID NO: 56:

(i) SEQUENCE CHARACTERISTICS:
        (A) LENGTH: 441 amino acids
        (B) TYPE: amino acid
        (D) TOPOLOGY: linear (ii) MOLECULE TYPE: protein (xi) SEQUENCE DESCRIPTION: SEQ ID NO: 56:

```
Met Met Val Leu Leu His Ala Val Tyr Ser Ile Val Phe Val Asp Val
 1               5                  10                  15

Ile Ile Ile Lys Val Gln Arg Tyr Ile Asn Asp Ile Leu Thr Leu Asp
                20                  25                  30

Ile Phe Tyr Leu Phe Lys Met Ile Pro Leu Leu Phe Ile Leu Phe Tyr
             35                  40                  45

Phe Ala Asn Gly Ile Glu Trp His Lys Phe Glu Thr Ser Glu Glu Ile
 50                  55                  60

Ile Ser Thr Tyr Leu Leu Asp Asp Val Leu Tyr Thr Gly Val Asn Gly
 65                  70                  75                  80

Ala Val Tyr Thr Phe Ser Asn Asn Lys Leu Asn Lys Thr Gly Leu Thr
                 85                  90                  95

Asn Asn Asn Tyr Ile Thr Thr Ser Ile Lys Val Glu Asp Ala Asp Lys
                100                 105                 110

Asp Thr Leu Val Cys Gly Thr Asn Asn Gly Asn Pro Lys Cys Trp Lys
            115                 120                 125

Ile Asp Gly Ser Asp Asp Pro Lys His Arg Gly Arg Gly Tyr Ala Pro
130                 135                 140

Tyr Gln Asn Ser Lys Val Thr Ile Ile Ser His Asn Gly Cys Val Leu
145                 150                 155                 160

Ser Asp Ile Asn Ile Ser Lys Glu Gly Ile Lys Arg Trp Arg Arg Phe
                165                 170                 175

Asp Gly Pro Cys Gly Tyr Asp Leu Tyr Thr Ala Asp Asn Val Ile Pro
            180                 185                 190

Lys Asp Gly Leu Arg Gly Ala Phe Val Asp Lys Asp Gly Thr Tyr Asp
            195                 200                 205

Lys Val Tyr Ile Leu Phe Thr Asp Thr Ile Gly Ser Lys Arg Ile Val
210                 215                 220

Lys Ile Pro Tyr Ile Ala Gln Met Cys Leu Asn Asp Glu Gly Gly Pro
225                 230                 235                 240

Ser Ser Leu Ser Ser His Arg Trp Ser Thr Phe Leu Lys Val Glu Leu
                245                 250                 255

Glu Cys Asp Ile Asp Gly Arg Ser Tyr Arg Gln Ile Ile His Ser Arg
            260                 265                 270

Thr Ile Lys Thr Asp Asn Asp Thr Ile Leu Tyr Val Phe Phe Asp Ser
            275                 280                 285

Pro Tyr Ser Lys Ser Ala Leu Cys Thr Tyr Ser Met Asn Thr Ile Lys
            290                 295                 300

Gln Ser Phe Ser Thr Ser Lys Leu Glu Gly Tyr Thr Lys Gln Leu Pro
305                 310                 315                 320

Ser Pro Ala Ser Gly Ile Cys Leu Pro Ala Gly Lys Val Val Pro His
                325                 330                 335

Thr Thr Phe Glu Val Ile Glu Lys Tyr Asn Val Leu Asp Asp Ile Ile
            340                 345                 350

Lys Pro Leu Ser Asn Gln Pro Ile Phe Glu Gly Pro Ser Gly Val Lys
            355                 360                 365
```

```
Trp Phe Asp Ile Lys Glu Lys Glu Asn Glu His Arg Glu Tyr Arg Ile
    370                 375                 380

Tyr Phe Ile Lys Glu Asn Ser Ile Tyr Ser Phe Asp Thr Lys Ser Lys
385                 390                 395                 400

Gln Thr Arg Ser Ser Gln Val Asp Ala Arg Leu Phe Ser Val Met Val
                405                 410                 415

Thr Ser Lys Pro Leu Phe Ile Ala Asp Ile Gly Ile Gly Val Gly Met
            420                 425                 430

Pro Gln Met Lys Lys Ile Leu Lys Met
        435                 440
```

(2) INFORMATION FOR SEQ ID NO: 57:

(i) SEQUENCE CHARACTERISTICS:
        (A) LENGTH: 2854 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 451..2640

(xi) SEQUENCE DESCRIPTION: SEQ ID NO: 57:

```
ATTCCACCTC CCGCTGACCG CCTACGCCGC GACGATCTTT CCTCTCGCCA GGCGAAAACT      60

ACGACGTGTC AACAACATTT TGTTTTTTC TGCTTCCGTG TTTTCATGTT CCGTGAAACC     120

GCTTCTCGCA TTACCACTCT TCCGTTTCCC AGTGTTTGTT TTCTCCGTTT CTTTCATCGT    180

GGATGTTTTG TTTTGGTGTA GCGAGTGACG AGCTTATGTC ATTAAACGTA CATCCAATCT    240

GTCGGTATAT TGGTGTGTGA TATTTTACTA TTATATATTT AGCCATCACT TGAAAGCCGT    300

GAAAAATTTT TGAAAGTGGA GAGGAAAAAG AAAAGGCGCA GAAGGCTTTT TAAGCTTCAT    360

GGATATGTGC TCTACGCTTC AACTACTGTC GCAGAATCAT CTTCCGGGAA AGGAAATTTC    420

GCCTGAAATG GTGCCGCGGC CGCACTGAAC ATG CGG GCG GCG CTG GTG GCC GTC    474
                                  Met Arg Ala Ala Leu Val Ala Val
                                    1               5

GCG GCG CTG CTT TGG GTG GCG CTG CAC GCC GCC GCA TGG GTC AAC GAC     522
Ala Ala Leu Leu Trp Val Ala Leu His Ala Ala Ala Trp Val Asn Asp
        10                  15                  20

GTC AGC CCC AAG ATG TAC GTC CAG TTC GGT GAG GAA CGG GTG CAA CGC     570
Val Ser Pro Lys Met Tyr Val Gln Phe Gly Glu Glu Arg Val Gln Arg
 25                  30                  35                  40

TTC CTG GGC AAT GAA TCG CAC AAA GAC CAC TTC AAG CTG CTG GAG AAG     618
Phe Leu Gly Asn Glu Ser His Lys Asp His Phe Lys Leu Leu Glu Lys
                 45                  50                  55

GAC CAC AAC TCG CTC CTC GTA GGA GCT AGG AAC ATC GTC TAC AAT ATC     666
Asp His Asn Ser Leu Leu Val Gly Ala Arg Asn Ile Val Tyr Asn Ile
             60                  65                  70

AGC CTT CGA GAC CTC ACA GAA TTC ACC GAG CAG AGG ATC GAG TGG CAC     714
Ser Leu Arg Asp Leu Thr Glu Phe Thr Glu Gln Arg Ile Glu Trp His
         75                  80                  85

TCG TCA GGT GCC CAT CGC GAG CTC TGC TAC CTC AAG GGG AAG TCA GAG     762
Ser Ser Gly Ala His Arg Glu Leu Cys Tyr Leu Lys Gly Lys Ser Glu
     90                  95                 100

GAC GAC TGC CAG AAC TAC ATC CGA GTC CTG GCG AAA ATT GAC GAT GAC     810
Asp Asp Cys Gln Asn Tyr Ile Arg Val Leu Ala Lys Ile Asp Asp Asp
105                 110                 115                 120
```

-continued

| | |
|---|---|
| CGC GTA CTC ATC TGC GGT ACG AAC GCC TAT AAG CCA CTA TGT CGG CAC<br>Arg Val Leu Ile Cys Gly Thr Asn Ala Tyr Lys Pro Leu Cys Arg His<br>            125                  130                  135 | 858 |
| TAC GCC CTC AAG GAT GGA GAT TAT GTT GTA GAG AAA GAA TAT GAG GGA<br>Tyr Ala Leu Lys Asp Gly Asp Tyr Val Val Glu Lys Glu Tyr Glu Gly<br>            140                  145                  150 | 906 |
| AGA GGA TTG TGC CCA TTT GAC CCT GAC CAC AAC AGC ACT GCA ATA TAC<br>Arg Gly Leu Cys Pro Phe Asp Pro Asp His Asn Ser Thr Ala Ile Tyr<br>            155                  160                  165 | 954 |
| AGT GAG GGA CAA TTG TAC TCA GCA ACA GTG GCA GAC TTC TCT GGA ACT<br>Ser Glu Gly Gln Leu Tyr Ser Ala Thr Val Ala Asp Phe Ser Gly Thr<br>170                  175                  180 | 1002 |
| GAC CCT CTC ATA TAC CGC GGC CCT CTA AGA ACA GAG AGA TCT GAC CTC<br>Asp Pro Leu Ile Tyr Arg Gly Pro Leu Arg Thr Glu Arg Ser Asp Leu<br>185                  190                  195                  200 | 1050 |
| AAA CAA TTA AAT GCT CCT AAC TTT GTC AAC ACA ATG GAG TAC AAT GAT<br>Lys Gln Leu Asn Ala Pro Asn Phe Val Asn Thr Met Glu Tyr Asn Asp<br>                    205                  210                  215 | 1098 |
| TTT ATA TTC TTC TTC TTC CGA GAG ACT GCT GTT GAG TAC ATC AAC TGC<br>Phe Ile Phe Phe Phe Phe Arg Glu Thr Ala Val Glu Tyr Ile Asn Cys<br>            220                  225                  230 | 1146 |
| GGA AAG GCT ATC TAT TCA AGA GTT GCC AGA GTC TGT AAA CAT GAC AAG<br>Gly Lys Ala Ile Tyr Ser Arg Val Ala Arg Val Cys Lys His Asp Lys<br>                  235                  240                  245 | 1194 |
| GGC GGC CCT CAT CAG GGT GGT GAC AGA TGG ACT TCT TTT TTG AAA TCA<br>Gly Gly Pro His Gln Gly Gly Asp Arg Trp Thr Ser Phe Leu Lys Ser<br>250                  255                  260 | 1242 |
| CGT CTG AAC TGT TCC GTC CCT GGA GAT TAT CCA TTT TAC TTC AAT GAA<br>Arg Leu Asn Cys Ser Val Pro Gly Asp Tyr Pro Phe Tyr Phe Asn Glu<br>265                  270                  275                  280 | 1290 |
| ATT CAG TCA ACA AGT GAC ATC ATT GAA GGA AAT TAT GGT GGT CAA GTG<br>Ile Gln Ser Thr Ser Asp Ile Ile Glu Gly Asn Tyr Gly Gly Gln Val<br>                    285                  290                  295 | 1338 |
| GAG AAA CTC ATC TAC GGT GTC TTC ACG ACA CCA GTG AAC TCT ATT GGT<br>Glu Lys Leu Ile Tyr Gly Val Phe Thr Thr Pro Val Asn Ser Ile Gly<br>            300                  305                  310 | 1386 |
| GGC TCT GCT GTT TGT GCC TTC AGT ATG AAG TCA ATA CTT GAG TCA TTT<br>Gly Ser Ala Val Cys Ala Phe Ser Met Lys Ser Ile Leu Glu Ser Phe<br>            315                  320                  325 | 1434 |
| GAT GGT CCA TTT AAA GAG CAG GAA ACG ATG AAC TCA AAC TGG TTG GCA<br>Asp Gly Pro Phe Lys Glu Gln Glu Thr Met Asn Ser Asn Trp Leu Ala<br>330                  335                  340 | 1482 |
| GTG CCA AGC CTT AAA GTG CCA GAA CCA AGG CCT GGA CAA TGT GTG AAT<br>Val Pro Ser Leu Lys Val Pro Glu Pro Arg Pro Gly Gln Cys Val Asn<br>345                  350                  355                  360 | 1530 |
| GAC AGT CGT ACA CTT CCT GAT GTG TCT GTC AAT TTT GTA AAG TCA CAT<br>Asp Ser Arg Thr Leu Pro Asp Val Ser Val Asn Phe Val Lys Ser His<br>                    365                  370                  375 | 1578 |
| ACA CTG ATG GAT GAG GCC GTG CCA GCA TTT TTT ACT CGG CCA ATT CTC<br>Thr Leu Met Asp Glu Ala Val Pro Ala Phe Phe Thr Arg Pro Ile Leu<br>            380                  385                  390 | 1626 |
| ATT CGG ATC AGC TTA CAG TAC AGA TTT ACA AAA ATA GCT GTT GAT CAA<br>Ile Arg Ile Ser Leu Gln Tyr Arg Phe Thr Lys Ile Ala Val Asp Gln<br>                  395                  400                  405 | 1674 |
| CAA GTC CGA ACA CCA GAT GGG AAA GCG TAT GAT GTC CTG TTT ATA GGA<br>Gln Val Arg Thr Pro Asp Gly Lys Ala Tyr Asp Val Leu Phe Ile Gly<br>410                  415                  420 | 1722 |
| ACT GAT GAT GGC AAA GTG ATA AAA GCT TTG AAC TCT GCC TCC TTT GAT<br>Thr Asp Asp Gly Lys Val Ile Lys Ala Leu Asn Ser Ala Ser Phe Asp<br>425                  430                  435                  440 | 1770 |

-continued

| | |
|---|---|
| TCA TCT GAT ACT GTA GAT AGT GTT GTA ATA GAA GAA CTG CAA GTG TTG<br>Ser Ser Asp Thr Val Asp Ser Val Val Ile Glu Glu Leu Gln Val Leu<br>                     445                      450                     455 | 1818 |
| CCA CCT GGA GTA CCT GTT AAG AAC CTG TAT GTG GTG CGA ATG GAT GGG<br>Pro Pro Gly Val Pro Val Lys Asn Leu Tyr Val Val Arg Met Asp Gly<br>          460                     465                     470 | 1866 |
| GAT GAT AGC AAG CTG GTG GTT GTG TCT GAT GAT GAG ATT CTG GCA ATT<br>Asp Asp Ser Lys Leu Val Val Val Ser Asp Asp Glu Ile Leu Ala Ile<br>         475                     480                     485 | 1914 |
| AAG CTT CAT CGT TGT GGC TCA GAT AAA ATA ACA AAT TGT CGA GAA TGT<br>Lys Leu His Arg Cys Gly Ser Asp Lys Ile Thr Asn Cys Arg Glu Cys<br>      490                     495                     500 | 1962 |
| GTG TCC TTG CAA GAT CCT TAC TGT GCA TGG GAC AAT GTA GAA TTA AAA<br>Val Ser Leu Gln Asp Pro Tyr Cys Ala Trp Asp Asn Val Glu Leu Lys<br>505                     510                     515                     520 | 2010 |
| TGT ACA GCT GTA GGT TCA CCA GAC TGG AGT GCT GGA AAA AGA CGC TTT<br>Cys Thr Ala Val Gly Ser Pro Asp Trp Ser Ala Gly Lys Arg Arg Phe<br>                   525                     530                     535 | 2058 |
| ATT CAG AAC ATT TCA CTC GGT GAA CAT AAA GCT TGT GGT GGA CGT CCA<br>Ile Gln Asn Ile Ser Leu Gly Glu His Lys Ala Cys Gly Gly Arg Pro<br>             540                     545                     550 | 2106 |
| CAA ACA GAA ATC GTT GCT TCT CCT GTA CCA ACT CAG CCG ACG ACA AAA<br>Gln Thr Glu Ile Val Ala Ser Pro Val Pro Thr Gln Pro Thr Thr Lys<br>      555                     560                     565 | 2154 |
| TCT AGT GGC GAT CCC GTT CAT TCA ATC CAC CAG GCT GAA TTT GAA CCT<br>Ser Ser Gly Asp Pro Val His Ser Ile His Gln Ala Glu Phe Glu Pro<br>         570                     575                     580 | 2202 |
| GAA ATT GAC AAC GAG ATT GTT ATT GGA GTA GAT GAC AGC AAC GTC ATT<br>Glu Ile Asp Asn Glu Ile Val Ile Gly Val Asp Asp Ser Asn Val Ile<br>585                     590                     595                     600 | 2250 |
| CCT AAT ACC CTG GCT GAA ATA AAT CAT GCA GGT TCA AAG CTG CCT TCC<br>Pro Asn Thr Leu Ala Glu Ile Asn His Ala Gly Ser Lys Leu Pro Ser<br>             605                     610                     615 | 2298 |
| TCC CAG GAA AAG TTG CCT ATT TAT ACA GCG GAG ACT CTG ACT ATT GCT<br>Ser Gln Glu Lys Leu Pro Ile Tyr Thr Ala Glu Thr Leu Thr Ile Ala<br>         620                     625                     630 | 2346 |
| ATA GTT ACA TCA TGC CTT GGA GCT CTA GTT GTT GGC TTC ATC TCT GGA<br>Ile Val Thr Ser Cys Leu Gly Ala Leu Val Val Gly Phe Ile Ser Gly<br>      635                     640                     645 | 2394 |
| TTT CTT TTT TCT CGG CGA TGC AGG GGA GAG GAT TAC ACA GAC ATG CCT<br>Phe Leu Phe Ser Arg Arg Cys Arg Gly Glu Asp Tyr Thr Asp Met Pro<br>650                     655                     660 | 2442 |
| TTT CCA GAT CAA CGC CAT CAG CTA AAT AGG CTC ACT GAG GCT GGT CTG<br>Phe Pro Asp Gln Arg His Gln Leu Asn Arg Leu Thr Glu Ala Gly Leu<br>665                     670                     675                     680 | 2490 |
| AAT GCA GAC TCA CCC TAT CTT CCA CCC TGT GCC AAT AAC AAG GCA GCC<br>Asn Ala Asp Ser Pro Tyr Leu Pro Pro Cys Ala Asn Asn Lys Ala Ala<br>             685                     690                     695 | 2538 |
| ATA AAT CTT GTG CTC AAT GTC CCA CCA AAG AAT GCA AAT GGA AAA AAT<br>Ile Asn Leu Val Leu Asn Val Pro Pro Lys Asn Ala Asn Gly Lys Asn<br>         700                     705                     710 | 2586 |
| GCC AAC TCT TCA GCT GAA AAC AAA CCA ATA CAG AAA GTA AAA AAG ACA<br>Ala Asn Ser Ser Ala Glu Asn Lys Pro Ile Gln Lys Val Lys Lys Thr<br>      715                     720                     725 | 2634 |
| TAC ATT TAGCAGAAAT CTTTGGTATC TGTTTTGGTG CAGACCCATG CCACTAGAGT<br>Tyr Ile<br>      730 | 2690 |
| AACCAAGACT CTATTGAGAA ATGTCCTCAA GAAAGTTAAA AAGATGTAGA CTTCTGTAAT | 2750 |

```
CGAGAGCACC ACTTTCCATA GTAATACAGA ACAATGTGAA ATAAATACTA CAGAAGAAGT    2810

CTTTGTTACA CAAAAAAGTG TATAGTGATC TGTGATCAGT TTCG                    2854
```

(2) INFORMATION FOR SEQ ID NO: 58:

(i) SEQUENCE CHARACTERISTICS:
        (A) LENGTH: 730 amino acids
        (B) TYPE: amino acid
        (D) TOPOLOGY: linear (ii) MOLECULE TYPE: protein (xi) SEQUENCE DESCRIPTION: SEQ ID NO: 58:

```
Met Arg Ala Ala Leu Val Ala Val Ala Ala Leu Leu Trp Val Ala Leu
  1               5                  10                  15

His Ala Ala Ala Trp Val Asn Asp Val Ser Pro Lys Met Tyr Val Gln
             20                  25                  30

Phe Gly Glu Glu Arg Val Gln Arg Phe Leu Gly Asn Glu Ser His Lys
         35                  40                  45

Asp His Phe Lys Leu Leu Glu Lys Asp His Asn Ser Leu Leu Val Gly
     50                  55                  60

Ala Arg Asn Ile Val Tyr Asn Ile Ser Leu Arg Asp Leu Thr Glu Phe
 65                  70                  75                  80

Thr Glu Gln Arg Ile Glu Trp His Ser Ser Gly Ala His Arg Glu Leu
                 85                  90                  95

Cys Tyr Leu Lys Gly Lys Ser Glu Asp Asp Cys Gln Asn Tyr Ile Arg
            100                 105                 110

Val Leu Ala Lys Ile Asp Asp Arg Val Leu Ile Cys Gly Thr Asn
        115                 120                 125

Ala Tyr Lys Pro Leu Cys Arg His Tyr Ala Leu Lys Asp Gly Asp Tyr
    130                 135                 140

Val Val Glu Lys Glu Tyr Glu Gly Arg Gly Leu Cys Pro Phe Asp Pro
145                 150                 155                 160

Asp His Asn Ser Thr Ala Ile Tyr Ser Glu Gly Gln Leu Tyr Ser Ala
                165                 170                 175

Thr Val Ala Asp Phe Ser Gly Thr Asp Pro Leu Ile Tyr Arg Gly Pro
            180                 185                 190

Leu Arg Thr Glu Arg Ser Asp Leu Lys Gln Leu Asn Ala Pro Asn Phe
        195                 200                 205

Val Asn Thr Met Glu Tyr Asn Asp Phe Ile Phe Phe Phe Arg Glu
    210                 215                 220

Thr Ala Val Glu Tyr Ile Asn Cys Gly Lys Ala Ile Tyr Ser Arg Val
225                 230                 235                 240

Ala Arg Val Cys Lys His Asp Lys Gly Gly Pro His Gln Gly Gly Asp
                245                 250                 255

Arg Trp Thr Ser Phe Leu Lys Ser Arg Leu Asn Cys Ser Val Pro Gly
            260                 265                 270

Asp Tyr Pro Phe Tyr Phe Asn Glu Ile Gln Ser Thr Ser Asp Ile Ile
        275                 280                 285

Glu Gly Asn Tyr Gly Gly Gln Val Glu Lys Leu Ile Tyr Gly Val Phe
    290                 295                 300

Thr Thr Pro Val Asn Ser Ile Gly Gly Ser Ala Val Cys Ala Phe Ser
305                 310                 315                 320

Met Lys Ser Ile Leu Glu Ser Phe Asp Gly Pro Phe Lys Glu Gln Glu
                325                 330                 335
```

-continued

```
Thr Met Asn Ser Asn Trp Leu Ala Val Pro Ser Leu Lys Val Pro Glu
            340                 345                 350

Pro Arg Pro Gly Gln Cys Val Asn Asp Ser Arg Thr Leu Pro Asp Val
            355                 360                 365

Ser Val Asn Phe Val Lys Ser His Thr Leu Met Asp Glu Ala Val Pro
            370                 375                 380

Ala Phe Phe Thr Arg Pro Ile Leu Ile Arg Ile Ser Leu Gln Tyr Arg
385                 390                 395                 400

Phe Thr Lys Ile Ala Val Asp Gln Gln Val Arg Thr Pro Asp Gly Lys
                405                 410                 415

Ala Tyr Asp Val Leu Phe Ile Gly Thr Asp Asp Gly Lys Val Ile Lys
                420                 425                 430

Ala Leu Asn Ser Ala Ser Phe Asp Ser Ser Asp Thr Val Asp Ser Val
                435                 440                 445

Val Ile Glu Glu Leu Gln Val Leu Pro Pro Gly Val Pro Val Lys Asn
450                 455                 460

Leu Tyr Val Val Arg Met Asp Gly Asp Ser Lys Leu Val Val Val
465                 470                 475                 480

Ser Asp Asp Glu Ile Leu Ala Ile Lys Leu His Arg Cys Gly Ser Asp
                485                 490                 495

Lys Ile Thr Asn Cys Arg Glu Cys Val Ser Leu Gln Asp Pro Tyr Cys
                500                 505                 510

Ala Trp Asp Asn Val Glu Leu Lys Cys Thr Ala Val Gly Ser Pro Asp
            515                 520                 525

Trp Ser Ala Gly Lys Arg Arg Phe Ile Gln Asn Ile Ser Leu Gly Glu
            530                 535                 540

His Lys Ala Cys Gly Gly Arg Pro Gln Thr Glu Ile Val Ala Ser Pro
545                 550                 555                 560

Val Pro Thr Gln Pro Thr Thr Lys Ser Ser Gly Asp Pro Val His Ser
                565                 570                 575

Ile His Gln Ala Glu Phe Glu Pro Glu Ile Asp Asn Glu Ile Val Ile
                580                 585                 590

Gly Val Asp Asp Ser Asn Val Ile Pro Asn Thr Leu Ala Glu Ile Asn
            595                 600                 605

His Ala Gly Ser Lys Leu Pro Ser Ser Gln Glu Lys Leu Pro Ile Tyr
            610                 615                 620

Thr Ala Glu Thr Leu Thr Ile Ala Ile Val Thr Ser Cys Leu Gly Ala
625                 630                 635                 640

Leu Val Val Gly Phe Ile Ser Gly Phe Leu Phe Ser Arg Arg Cys Arg
                645                 650                 655

Gly Glu Asp Tyr Thr Asp Met Pro Phe Pro Asp Gln Arg His Gln Leu
                660                 665                 670

Asn Arg Leu Thr Glu Ala Gly Leu Asn Ala Asp Ser Pro Tyr Leu Pro
                675                 680                 685

Pro Cys Ala Asn Asn Lys Ala Ala Ile Asn Leu Val Leu Asn Val Pro
            690                 695                 700

Pro Lys Asn Ala Asn Gly Lys Asn Ala Asn Ser Ser Ala Glu Asn Lys
705                 710                 715                 720

Pro Ile Gln Lys Val Lys Lys Thr Tyr Ile
                725                 730
```

(2) INFORMATION FOR SEQ ID NO: 59:

(i) SEQUENCE CHARACTERISTICS:

(A) LENGTH: 3560 base pairs
(B) TYPE: nucleic acid
(C) STRANDEDNESS: double
(D) TOPOLOGY: linear (ii) MOLECULE TYPE: cDNA (ix) FEATURE:
(A) NAME/KEY: CDS
(B) LOCATION: 1..1953

(xi) SEQUENCE DESCRIPTION: SEQ ID NO: 59:

| | | | | | | | | | | | | | | | | |
|---|---|---|---|---|---|---|---|---|---|---|---|---|---|---|---|---|
| GAG | GAT | GAT | TGT | CAG | AAT | TAC | ATC | CGC | ATC | ATG | GTG | GTG | CCA | TCG | CCG | 48 |
| Glu | Asp | Asp | Cys | Gln | Asn | Tyr | Ile | Arg | Ile | Met | Val | Val | Pro | Ser | Pro | |
| 1 | | | | 5 | | | | | 10 | | | | | 15 | | |
| GGT | CGC | CTT | TTC | GTT | TGT | GGC | ACC | AAC | TCG | TTC | CGG | CCC | ATG | TGC | AAC | 96 |
| Gly | Arg | Leu | Phe | Val | Cys | Gly | Thr | Asn | Ser | Phe | Arg | Pro | Met | Cys | Asn | |
| | | | 20 | | | | | 25 | | | | | 30 | | | |
| ACG | TAT | ATC | ATT | AGT | GAC | AGC | AAC | TAC | ACG | CTG | GAG | GCC | ACG | AAG | AAC | 144 |
| Thr | Tyr | Ile | Ile | Ser | Asp | Ser | Asn | Tyr | Thr | Leu | Glu | Ala | Thr | Lys | Asn | |
| | | | | 35 | | | | | 40 | | | | | 45 | | |
| GGA | CAG | GCG | GTG | TGC | CCC | TAC | GAT | CCA | CGT | CAC | AAC | TCC | ACC | TCT | GTG | 192 |
| Gly | Gln | Ala | Val | Cys | Pro | Tyr | Asp | Pro | Arg | His | Asn | Ser | Thr | Ser | Val | |
| | 50 | | | | | 55 | | | | | 60 | | | | | |
| CTG | GCC | GAC | AAC | GAA | CTG | TAT | TCC | GGT | ACC | GTG | GCG | GAT | TTC | AGT | GGC | 240 |
| Leu | Ala | Asp | Asn | Glu | Leu | Tyr | Ser | Gly | Thr | Val | Ala | Asp | Phe | Ser | Gly | |
| 65 | | | | | 70 | | | | | 75 | | | | | 80 | |
| AGC | GAT | CCG | ATT | ATC | TAC | CGG | GAG | CCC | CTG | CAG | ACC | GAG | CAG | TAC | GAT | 288 |
| Ser | Asp | Pro | Ile | Ile | Tyr | Arg | Glu | Pro | Leu | Gln | Thr | Glu | Gln | Tyr | Asp | |
| | | | | 85 | | | | | 90 | | | | | 95 | | |
| AGC | CTA | AGT | CTC | AAC | GCA | CCG | AAC | TTT | GTG | AGC | TCA | TTT | ACG | CAG | GGC | 336 |
| Ser | Leu | Ser | Leu | Asn | Ala | Pro | Asn | Phe | Val | Ser | Ser | Phe | Thr | Gln | Gly | |
| | | | 100 | | | | | 105 | | | | | 110 | | | |
| GAC | TTT | GTC | TAT | TTC | TTC | TTT | CGG | GAA | ACC | GCC | GTT | GAG | TTT | ATC | AAC | 384 |
| Asp | Phe | Val | Tyr | Phe | Phe | Phe | Arg | Glu | Thr | Ala | Val | Glu | Phe | Ile | Asn | |
| | | | | 115 | | | | | 120 | | | | | 125 | | |
| TGT | GGC | AAG | GCG | ATT | TAT | TCG | CGC | GTT | GCC | CGC | GTC | TGC | AAA | TGG | GAC | 432 |
| Cys | Gly | Lys | Ala | Ile | Tyr | Ser | Arg | Val | Ala | Arg | Val | Cys | Lys | Trp | Asp | |
| | 130 | | | | | 135 | | | | | 140 | | | | | |
| AAA | GGT | GGC | CCG | CAT | CGA | TTC | CGC | AAC | CGC | TGG | ACA | TCC | TTC | CTC | AAG | 480 |
| Lys | Gly | Gly | Pro | His | Arg | Phe | Arg | Asn | Arg | Trp | Thr | Ser | Phe | Leu | Lys | |
| 145 | | | | | 150 | | | | | 155 | | | | | 160 | |
| TCC | CGC | CTC | AAC | TGC | TCC | ATT | CCC | GGC | GAT | TAT | CCT | TTC | TAC | TTT | AAT | 528 |
| Ser | Arg | Leu | Asn | Cys | Ser | Ile | Pro | Gly | Asp | Tyr | Pro | Phe | Tyr | Phe | Asn | |
| | | | | 165 | | | | | 170 | | | | | 175 | | |
| GAA | ATC | CAA | TCT | GCC | AGC | AAT | CTG | GTG | GAG | GGA | CAG | TAT | GGC | TCG | ATG | 576 |
| Glu | Ile | Gln | Ser | Ala | Ser | Asn | Leu | Val | Glu | Gly | Gln | Tyr | Gly | Ser | Met | |
| | | | 180 | | | | | 185 | | | | | 190 | | | |
| AGC | TCG | AAA | CTG | ATC | TAC | GGA | GTC | TTC | AAC | ACG | CCG | AGC | AAC | TCA | ATT | 624 |
| Ser | Ser | Lys | Leu | Ile | Tyr | Gly | Val | Phe | Asn | Thr | Pro | Ser | Asn | Ser | Ile | |
| | | | | 195 | | | | | 200 | | | | | 205 | | |
| CCC | GGC | TCA | GCG | GTT | TGT | GCC | TTT | GCC | CTC | CAG | GAC | ATT | GCC | GAT | ACG | 672 |
| Pro | Gly | Ser | Ala | Val | Cys | Ala | Phe | Ala | Leu | Gln | Asp | Ile | Ala | Asp | Thr | |
| | 210 | | | | | 215 | | | | | 220 | | | | | |
| TTT | GAG | GGT | CAG | TTC | AAG | GAG | CAG | ACT | GGC | ATC | AAC | TCC | AAC | TGG | CTG | 720 |
| Phe | Glu | Gly | Gln | Phe | Lys | Glu | Gln | Thr | Gly | Ile | Asn | Ser | Asn | Trp | Leu | |
| 225 | | | | | 230 | | | | | 235 | | | | | 240 | |
| CCA | GTG | AAC | AAC | GCC | AAG | GTA | CCC | GAT | CCT | CGA | CCC | GGT | TCC | TGT | CAC | 768 |
| Pro | Val | Asn | Asn | Ala | Lys | Val | Pro | Asp | Pro | Arg | Pro | Gly | Ser | Cys | His | |
| | | | | 245 | | | | | 250 | | | | | 255 | | |
| AAC | GAT | TCG | AGA | GCG | CTT | CCG | GAT | CCC | ACA | CTG | AAC | TTC | ATC | AAA | ACA | 816 |
| Asn | Asp | Ser | Arg | Ala | Leu | Pro | Asp | Pro | Thr | Leu | Asn | Phe | Ile | Lys | Thr | |

```
                    260                 265                 270
CAT TCG CTA ATG GAC GAG AAT GTG CCG GCA TTT TTC AGT CAA CCG ATT    864
His Ser Leu Met Asp Glu Asn Val Pro Ala Phe Phe Ser Gln Pro Ile
        275                 280                 285

TTG GTC CGG ACG AGC ACA ATA TAC CGC TTC ACT CAA ATC GCC GTA GAT    912
Leu Val Arg Thr Ser Thr Ile Tyr Arg Phe Thr Gln Ile Ala Val Asp
        290                 295                 300

GCG CAG ATT AAA ACT CCT GGC GGC AAG ACA TAT GAT GTT ATC TTT GTG    960
Ala Gln Ile Lys Thr Pro Gly Gly Lys Thr Tyr Asp Val Ile Phe Val
305                 310                 315                 320

GGC ACA GAT CAT GGA AAG ATT ATT AAG TCA GTG AAT GCT GAA TCT GCC    1008
Gly Thr Asp His Gly Lys Ile Ile Lys Ser Val Asn Ala Glu Ser Ala
                325                 330                 335

GAT TCA GCG GAT AAA GTC ACC TCC GTA GTC ATC GAG GAG ATC GAT GTC    1056
Asp Ser Ala Asp Lys Val Thr Ser Val Val Ile Glu Glu Ile Asp Val
                340                 345                 350

CTG ACC AAG AGT GAA CCC ATA CGC AAT CTG GAG ATA GTC AGA ACC ATG    1104
Leu Thr Lys Ser Glu Pro Ile Arg Asn Leu Glu Ile Val Arg Thr Met
                355                 360                 365

CAG TAC GAT CAA CCC AAA GAT GGC AGC TAC GAC GAT GGT AAA TTA ATC    1152
Gln Tyr Asp Gln Pro Lys Asp Gly Ser Tyr Asp Asp Gly Lys Leu Ile
        370                 375                 380

ATT GTG ACG GAC AGT CAG GTG GTA GCC ATA CAA TTG CAT CGT TGT CAC    1200
Ile Val Thr Asp Ser Gln Val Val Ala Ile Gln Leu His Arg Cys His
385                 390                 395                 400

AAT GAC AAA ATC ACC AGC TGC AGC GAG TGC GTC GCA TTG CAG GAT CCG    1248
Asn Asp Lys Ile Thr Ser Cys Ser Glu Cys Val Ala Leu Gln Asp Pro
                405                 410                 415

TAC TGC GCC TGG GAC AAA ATC GCT GGC AAG TGC CGT TCC CAC GGC GCT    1296
Tyr Cys Ala Trp Asp Lys Ile Ala Gly Lys Cys Arg Ser His Gly Ala
                420                 425                 430

CCC CGA TGG CTA GAG GAG AAC TAT TTC TAC CAG AAT GTG GCC ACT GGC    1344
Pro Arg Trp Leu Glu Glu Asn Tyr Phe Tyr Gln Asn Val Ala Thr Gly
        435                 440                 445

CAG CAT GCG GCC TGC CCC TCA GGC AAA ATC AAT TCA AAG GAT GCC AAC    1392
Gln His Ala Ala Cys Pro Ser Gly Lys Ile Asn Ser Lys Asp Ala Asn
        450                 455                 460

GCT GGG GAG CAG AAG GGC TTC CGC AAC GAC ATG GAC TTA TTG GAT TCG    1440
Ala Gly Glu Gln Lys Gly Phe Arg Asn Asp Met Asp Leu Leu Asp Ser
465                 470                 475                 480

CGA CGC CAG AGC AAG GAT CAG GAA ATA ATC GAC AAT ATT GAT AAG AAC    1488
Arg Arg Gln Ser Lys Asp Gln Glu Ile Ile Asp Asn Ile Asp Lys Asn
                485                 490                 495

TTT GAA GAT ATA ATC AAC GCC CAG TAC ACT GTG GAG ACC CTC GTG ATG    1536
Phe Glu Asp Ile Ile Asn Ala Gln Tyr Thr Val Glu Thr Leu Val Met
                500                 505                 510

GCC GTT CTG GCC GGT TCG ATC TTT TCG CTG CTG GTC GGC TTC TTT ACA    1584
Ala Val Leu Ala Gly Ser Ile Phe Ser Leu Leu Val Gly Phe Phe Thr
                515                 520                 525

GGC TAC TTC TGC GGT CGC CGT TGT CAC AAG GAC GAG GAT GAT AAT CTG    1632
Gly Tyr Phe Cys Gly Arg Arg Cys His Lys Asp Glu Asp Asp Asn Leu
        530                 535                 540

CCG TAT CCG GAT ACG GAG TAC GAG TAC TTC GAG CAG CGA CAG AAT GTC    1680
Pro Tyr Pro Asp Thr Glu Tyr Glu Tyr Phe Glu Gln Arg Gln Asn Val
545                 550                 555                 560

AAT AGC TTC CCC TCG TCC TGT CGC ATC CAG CAG GAG CCC AAG CTG CTG    1728
Asn Ser Phe Pro Ser Ser Cys Arg Ile Gln Gln Glu Pro Lys Leu Leu
                565                 570                 575

CCC CAA GTG GAG GAG GTG ACG TAT GCG GAC GCA GTG CTC CTG CCA CAG    1776
```

-continued

```
Pro Gln Val Glu Glu Val Thr Tyr Ala Asp Ala Val Leu Leu Pro Gln
            580                 585                 590

CCT CCG CCG CCC AAT AAG ATG CAC TCG CCG AAG AAC ACG CTG CGT AAG        1824
Pro Pro Pro Pro Asn Lys Met His Ser Pro Lys Asn Thr Leu Arg Lys
            595                 600                 605

CCC CCG ATG CAC CAG ATG CAC CAG GGT CCC AAC TCG GAG ACC CTC TTC        1872
Pro Pro Met His Gln Met His Gln Gly Pro Asn Ser Glu Thr Leu Phe
            610                 615                 620

CAG TTC CAC GTG ACG GCT ACA ACA CCC AGC AGT CGT ATC GTG GTC GCG        1920
Gln Phe His Val Thr Ala Thr Thr Pro Ser Ser Arg Ile Val Val Ala
625                 630                 635                 640

ACA ACT TCG GAA CAC TGC GTT CCC ACC AGG TGATGGGCGA CAATTACAGG          1970
Thr Thr Ser Glu His Cys Val Pro Thr Arg
                645                 650

CGCGGCGATG GCTTTTCCAC CACCCGCAGC GTCAAGAAGG TTTACCTTTG AGACGGGAGT      2030

GGGGCGGCTG AAACCAGTCA GGGACTAATT ACCCAAAATA TGGCTGTAAA CAACACAAAC      2090

ACACGTAACA GAAGTCTTGG TCGCGCAAGA AGACAGCCGC CCCGTCATGG CATTGTAACT      2150

CAACACCGCT CGAATAGCCC CCAGCAGCAG CAGCAGCAGT CGCAGCAGCC GCACTCCAGT      2210

TCGGGCTCCT CGCCCGTAAT GTCCAACAGC AGCAGCAGTC CGGCTCCGCC CTCCAGCAGT      2270

CCCAGTCCGC AGGAGAGCCC CAAGAACTGC AGCTACATCT ACCGTGATTG ATTGATATGC      2330

AACACCAAAT CGATGCCACT CATCCAGGCC CAGTCCACGC ACGCCCAGCC ACACTCACAC      2390

CCGCACCCGC ACCCGCTTCC GCCACCCGGT CCGACCACGC CCCCAGCACA GCCACGCGCC      2450

AGAAGTCCAA TGATCGGCAG GACATATGCC AAGTCCATGC CCGTGACACC AGTTCAACCG      2510

CAATCGCCGC TGGCTGAGAC GCCCTCCTAT GAGCTCTACG AACGCCACTC GGATGCGGCC      2570

ACCTTCCACT TTGGGGATGA GGACGATGAC GATGATGATG AGCACGACCA GGAGGACACC      2630

TCATCGCTGG CCATGATCAC ACCGCCGCCG CCCTACGACA CTCCGCATCT GATTGCATCG      2690

CCACCGCTGC CGCCGCCTCG TAGATTTCGC TTTGGCAACA GGGAGCTGTT CAGCATGAGT      2750

CCAGCCGGAG GTGGAACCAC GCCCACCGCC TCGGCAGGCC AACGCGGCAG CAGCGCCATC      2810

ACGCCCACAA AGTTGAGTGC GGCGGCAGCG GCCATGTTTG CCGCACCCCA AATGGCCACC      2870

CAACTCAACC GGAAGTGGGC TCATTTGCAA AGGAAGCGGC GCAGGCGCAA CAGCAGCTCC      2930

GGCGATTCTA AGGAGCTCGA CAAACTGGTC CTGCAATCGG TCGACTGGGA TGAGAATGAG      2990

ATGTACTAGA ACGCAAACCA ACAATGAGAT AGCAGAAACA CTTTGATTCG GAATTTATAC      3050

ACCTTTGCAT ATTTTGAATA TGACTTCAAT TTTAAAATGC GTAATTATGT TCTTATTTTT      3110

TAAAGAACGC TTTAGAGAAG TTTTCTGCTA CCTTAAATAG TACACACAAC TCATATCTAA      3170

CGTGGCGCTG CGATATAGGA ATAACCACTC CCCCTTCCCT TAAACTTAAA GTAGCAATCG      3230

AAAAGATCAT TCATTAGCGA CAGAAACTGG ATGGGGATTT ACTTACACAC AAAAAGCCAG      3290

AGAAGTTATA CACGAAGTTT ATAGTTATAT AGCCTTTATA CATACTCCCC GATCTGCTAA      3350

GTATACACAA GCAAGCATAA CATAACATAC GTATATATGA CTCTATATAT ACCAATAGAT      3410

TTCATAGACG ATTCACATGG ATCGGCTACG CTAAATTAGA GCTGCAAAAT GATATTGTTA      3470

ATTACGATTA GAGAAAAAAA AAAAGGAATT CGATATCAAG CKTATCGATA CCNTCGACCT      3530

CGNNNNNGGG GCCCGGTACC CAATTCGCCC                                       3560
```

(2) INFORMATION FOR SEQ ID NO: 60:

(i) SEQUENCE CHARACTERISTICS:
        (A) LENGTH: 650 amino acids
        (B) TYPE: amino acid (D) TOPOLOGY: linear (ii) MOLECULE TYPE: protein (xi) SEQUENCE DESCRIPTION: SEQ ID NO: 60:

Glu Asp Asp Cys Gln Asn Tyr Ile Arg Ile Met Val Val Pro Ser Pro
 1               5                  10                  15

Gly Arg Leu Phe Val Cys Gly Thr Asn Ser Phe Arg Pro Met Cys Asn
             20                  25                  30

Thr Tyr Ile Ile Ser Asp Ser Asn Tyr Thr Leu Glu Ala Thr Lys Asn
         35                  40                  45

Gly Gln Ala Val Cys Pro Tyr Asp Pro Arg His Asn Ser Thr Ser Val
     50                  55                  60

Leu Ala Asp Asn Glu Leu Tyr Ser Gly Thr Val Ala Asp Phe Ser Gly
 65                  70                  75                  80

Ser Asp Pro Ile Ile Tyr Arg Glu Pro Leu Gln Thr Glu Gln Tyr Asp
                 85                  90                  95

Ser Leu Ser Leu Asn Ala Pro Asn Phe Val Ser Ser Phe Thr Gln Gly
             100                 105                 110

Asp Phe Val Tyr Phe Phe Phe Arg Glu Thr Ala Val Glu Phe Ile Asn
         115                 120                 125

Cys Gly Lys Ala Ile Tyr Ser Arg Val Ala Arg Val Cys Lys Trp Asp
    130                 135                 140

Lys Gly Gly Pro His Arg Phe Arg Asn Arg Trp Thr Ser Phe Leu Lys
145                 150                 155                 160

Ser Arg Leu Asn Cys Ser Ile Pro Gly Asp Tyr Pro Phe Tyr Phe Asn
                165                 170                 175

Glu Ile Gln Ser Ala Ser Asn Leu Val Glu Gly Gln Tyr Gly Ser Met
            180                 185                 190

Ser Ser Lys Leu Ile Tyr Gly Val Phe Asn Thr Pro Ser Asn Ser Ile
        195                 200                 205

Pro Gly Ser Ala Val Cys Ala Phe Ala Leu Gln Asp Ile Ala Asp Thr
    210                 215                 220

Phe Glu Gly Gln Phe Lys Glu Gln Thr Gly Ile Asn Ser Asn Trp Leu
225                 230                 235                 240

Pro Val Asn Asn Ala Lys Val Pro Asp Pro Arg Pro Gly Ser Cys His
                245                 250                 255

Asn Asp Ser Arg Ala Leu Pro Asp Pro Thr Leu Asn Phe Ile Lys Thr
            260                 265                 270

His Ser Leu Met Asp Glu Asn Val Pro Ala Phe Phe Ser Gln Pro Ile
        275                 280                 285

Leu Val Arg Thr Ser Thr Ile Tyr Arg Phe Thr Gln Ile Ala Val Asp
    290                 295                 300

Ala Gln Ile Lys Thr Pro Gly Gly Lys Thr Tyr Asp Val Ile Phe Val
305                 310                 315                 320

Gly Thr Asp His Gly Lys Ile Ile Lys Ser Val Asn Ala Glu Ser Ala
                325                 330                 335

Asp Ser Ala Asp Lys Val Thr Ser Val Ile Glu Glu Ile Asp Val
            340                 345                 350

Leu Thr Lys Ser Glu Pro Ile Arg Asn Leu Glu Ile Val Arg Thr Met
        355                 360                 365

Gln Tyr Asp Gln Pro Lys Asp Gly Ser Tyr Asp Asp Gly Lys Leu Ile
    370                 375                 380

Ile Val Thr Asp Ser Gln Val Val Ala Ile Gln Leu His Arg Cys His

```
                385                 390                 395                 400
         Asn Asp Lys Ile Thr Ser Cys Ser Glu Cys Val Ala Leu Gln Asp Pro
                         405                 410                 415

Tyr Cys Ala Trp Asp Lys Ile Ala Gly Lys Cys Arg Ser His Gly Ala
                         420                 425                 430

Pro Arg Trp Leu Glu Glu Asn Tyr Phe Tyr Gln Asn Val Ala Thr Gly
                         435                 440                 445

Gln His Ala Ala Cys Pro Ser Gly Lys Ile Asn Ser Lys Asp Ala Asn
                         450                 455                 460

Ala Gly Glu Gln Lys Gly Phe Arg Asn Asp Met Asp Leu Leu Asp Ser
         465                 470                 475                 480

Arg Arg Gln Ser Lys Asp Gln Glu Ile Ile Asp Asn Ile Asp Lys Asn
                         485                 490                 495

Phe Glu Asp Ile Ile Asn Ala Gln Tyr Thr Val Glu Thr Leu Val Met
                         500                 505                 510

Ala Val Leu Ala Gly Ser Ile Phe Ser Leu Leu Val Gly Phe Phe Thr
                         515                 520                 525

Gly Tyr Phe Cys Gly Arg Arg Cys His Lys Asp Glu Asp Asp Asn Leu
                         530                 535                 540

Pro Tyr Pro Asp Thr Glu Tyr Glu Tyr Phe Glu Gln Arg Gln Asn Val
         545                 550                 555                 560

Asn Ser Phe Pro Ser Ser Cys Arg Ile Gln Gln Glu Pro Lys Leu Leu
                         565                 570                 575

Pro Gln Val Glu Glu Val Thr Tyr Ala Asp Ala Val Leu Leu Pro Gln
                         580                 585                 590

Pro Pro Pro Asn Lys Met His Ser Pro Lys Asn Thr Leu Arg Lys
                         595                 600                 605

Pro Pro Met His Gln Met His Gln Gly Pro Asn Ser Glu Thr Leu Phe
         610                 615                 620

Gln Phe His Val Thr Ala Thr Thr Pro Ser Ser Arg Ile Val Val Ala
         625                 630                 635                 640

Thr Thr Ser Glu His Cys Val Pro Thr Arg
                         645                 650

(2) INFORMATION FOR SEQ ID NO: 61:

(i) SEQUENCE CHARACTERISTICS:
         (A) LENGTH: 2670 base pairs
         (B) TYPE: nucleic acid
         (C) STRANDEDNESS: double
         (D) TOPOLOGY: linear (ii) MOLECULE TYPE: cDNA (ix) FEATURE:
         (A) NAME/KEY: CDS
         (B) LOCATION: 268..2439

(xi) SEQUENCE DESCRIPTION: SEQ ID NO: 61:

GAAAATCGAA CWCCGAATTG AATGAACWGC AAAACGCCAA TTAGATAGTT GCAAGCCTAA        60

TGCATTTCAG AKATTTNMMC GATGCGAAAC AAGTTCCGCC ACGAAAGTGA ACAGTGGTAA       120

AATGCCCAAG AATCTCGAGC GGAAACACCA AACACAAAAG AACAAGCAAC CGCCTCTCAC      180

TCGCTCTTGC ACTTTAATCC AATTGAGGTT GGTGGGGTCG CATTCGCCCC CCGGTCGACC      240

ACCCCTCTCG CTCGCACCGC CCTCGCA ATG TCT CTT CTA CAG CTA TCG CCG CTC     294
                                Met Ser Leu Leu Gln Leu Ser Pro Leu
                                  1               5
```

```
CTC GCA CTC CTG CTA CTC CTC TGC AGT AGT GTG AGC GAG ACG GCT GCG        342
Leu Ala Leu Leu Leu Leu Leu Cys Ser Ser Val Ser Glu Thr Ala Ala
 10              15                  20                  25

GAC TAC GAG AAC ACC TGG AAC TTC TAC TAC GAG CGT CCC TGT TGC ACT        390
Asp Tyr Glu Asn Thr Trp Asn Phe Tyr Tyr Glu Arg Pro Cys Cys Thr
                 30                  35                  40

GGA AAC GAT CAG GGG AAC AAC AAT TAC GGA AAA CAC GGC GCA GAT CAT        438
Gly Asn Asp Gln Gly Asn Asn Asn Tyr Gly Lys His Gly Ala Asp His
             45                  50                  55

GTG CGG GAG TTC AAC TGC GGC AAG CTG TAC TAT CGT ACA TTC CAT ATG        486
Val Arg Glu Phe Asn Cys Gly Lys Leu Tyr Tyr Arg Thr Phe His Met
         60                  65                  70

AAC GAA GAT CGA GAT ACG CTC TAT GTG GGA GCC ATG GAT CGC GTA TTC        534
Asn Glu Asp Arg Asp Thr Leu Tyr Val Gly Ala Met Asp Arg Val Phe
 75                  80                  85

CGT GTG AAC CTG CAG AAT ATC TCC TCA TCC AAT TGT AAT CGG GAT GCG        582
Arg Val Asn Leu Gln Asn Ile Ser Ser Ser Asn Cys Asn Arg Asp Ala
 90                  95                 100                 105

ATC AAC TTG GAG CCA ACA CGG GAT GAT GTG GTT AGC TGC GTC TCC AAA        630
Ile Asn Leu Glu Pro Thr Arg Asp Asp Val Val Ser Cys Val Ser Lys
                110                 115                 120

GGC AAA AGT CAG ATC TTC GAC TGC AAG AAC CAT GTG CGT GTC ATC CAG        678
Gly Lys Ser Gln Ile Phe Asp Cys Lys Asn His Val Arg Val Ile Gln
            125                 130                 135

TCA ATG GAC CAG GGG GAT AGG CTC TAT GTA TGC GGC ACC AAC GCC CAC        726
Ser Met Asp Gln Gly Asp Arg Leu Tyr Val Cys Gly Thr Asn Ala His
            140                 145                 150

AAT CCC AAG GAT TAT GTT ATC TAT GCG AAT CTA ACC CAC CTG CCG CGC        774
Asn Pro Lys Asp Tyr Val Ile Tyr Ala Asn Leu Thr His Leu Pro Arg
155                 160                 165

TCG GAA TAT GTG ATT GGC GTG GGT CTG GGC ATT GCC AAG TGC CCC TAC        822
Ser Glu Tyr Val Ile Gly Val Gly Leu Gly Ile Ala Lys Cys Pro Tyr
170                 175                 180                 185

GAT CCC CTC GAC AAC TCA ACT GCG ATT TAT GTG GAG AAT GGC AAT CCG        870
Asp Pro Leu Asp Asn Ser Thr Ala Ile Tyr Val Glu Asn Gly Asn Pro
                190                 195                 200

GGT GGT CTG CCC GGT TTG TAC TCC GGC ACC AAT GCG GAG TTC ACC AAG        918
Gly Gly Leu Pro Gly Leu Tyr Ser Gly Thr Asn Ala Glu Phe Thr Lys
            205                 210                 215

GCG GAT ACG GTT ATT TTC CGC ACT GAT CTG TAT AAT ACT TCG GCT AAA        966
Ala Asp Thr Val Ile Phe Arg Thr Asp Leu Tyr Asn Thr Ser Ala Lys
            220                 225                 230

CGT TTG GAA TAT AAA TTC AAG AGG ACT CTG AAA TAC GAC TCC AAG TGG       1014
Arg Leu Glu Tyr Lys Phe Lys Arg Thr Leu Lys Tyr Asp Ser Lys Trp
235                 240                 245

TTG GAC AAA CCA AAC TTT GTC GGC TCC TTT GAT ATT GGG GAG TAC GTG      1062
Leu Asp Lys Pro Asn Phe Val Gly Ser Phe Asp Ile Gly Glu Tyr Val
250                 255                 260                 265

TAT TTC TTT TTC CGT GAA ACC GCC GTG GAA TAC ATC AAC TGC GGC AAG       1110
Tyr Phe Phe Phe Arg Glu Thr Ala Val Glu Tyr Ile Asn Cys Gly Lys
                270                 275                 280

GCT GTC TAT TCG CGC ATC GCA CGG GTG TGC AAG AAG GAT GTG GGT GGA       1158
Ala Val Tyr Ser Arg Ile Ala Arg Val Cys Lys Lys Asp Val Gly Gly
            285                 290                 295

AAG AAT CTG CTG GCC CAC AAC TGG GCC ACC TAC CTG AAG GCC AGA CTC       1206
Lys Asn Leu Leu Ala His Asn Trp Ala Thr Tyr Leu Lys Ala Arg Leu
            300                 305                 310

AAC TGC AGC ATC TCC GGC GAA TTT CCG TTC TAT TTC AAC GAG ATC CAA       1254
Asn Cys Ser Ile Ser Gly Glu Phe Pro Phe Tyr Phe Asn Glu Ile Gln
315                 320                 325
```

```
TCG GTC TAC CAG CTG CCC TCC GAT AAG AGT CGA TTC TTC GCC ACA TTC      1302
Ser Val Tyr Gln Leu Pro Ser Asp Lys Ser Arg Phe Phe Ala Thr Phe
330                 335                 340                 345

ACG ACG AGC ACT AAT GGC CTG ATT GGA TCT GCC GTA TGC AGT TTC CAC      1350
Thr Thr Ser Thr Asn Gly Leu Ile Gly Ser Ala Val Cys Ser Phe His
                350                 355                 360

ATT AAC GAG ATT CAG GCT GCC TTC AAT GGC AAA TTC AAG GAG CAA TCT      1398
Ile Asn Glu Ile Gln Ala Ala Phe Asn Gly Lys Phe Lys Glu Gln Ser
            365                 370                 375

TCA TCG AAT TCC GCA TGG CTG CCG GTG CTT AAC TCC CGG GTG CCG GAA      1446
Ser Ser Asn Ser Ala Trp Leu Pro Val Leu Asn Ser Arg Val Pro Glu
        380                 385                 390

CCA CGG CCG GGT ACA TGT GTC AAC GAT ACA TCA AAC CTG CCC GAT ACC      1494
Pro Arg Pro Gly Thr Cys Val Asn Asp Thr Ser Asn Leu Pro Asp Thr
    395                 400                 405

GTA CTG AAT TTC ATC AGA TCC CAT CCA CTT ATG GAC AAA GCC GTA AAT      1542
Val Leu Asn Phe Ile Arg Ser His Pro Leu Met Asp Lys Ala Val Asn
410                 415                 420                 425

CAC GAG CAC AAC AAT CCA GTC TAT TAT AAA AGG GAT TTG GTC TTC ACC      1590
His Glu His Asn Asn Pro Val Tyr Tyr Lys Arg Asp Leu Val Phe Thr
                430                 435                 440

AAG CTC GTC GTT GAC AAA ATT CGC ATT GAC ATC CTC AAC CAG GAA TAC      1638
Lys Leu Val Val Asp Lys Ile Arg Ile Asp Ile Leu Asn Gln Glu Tyr
            445                 450                 455

ATT GTG TAC TAT GTG GGC ACC AAT CTG GGT CGC ATT TAC AAA ATC GTG      1686
Ile Val Tyr Tyr Val Gly Thr Asn Leu Gly Arg Ile Tyr Lys Ile Val
        460                 465                 470

CAG TAC TAC CGT AAC GGA GAG TCG CTG TCC AAG CTT CTG GAT ATC TTC      1734
Gln Tyr Tyr Arg Asn Gly Glu Ser Leu Ser Lys Leu Leu Asp Ile Phe
    475                 480                 485

GAG GTG GCT CCA AAC GAG GCC ATC CAA GTG ATG GAA ATC AGC CAG ACA      1782
Glu Val Ala Pro Asn Glu Ala Ile Gln Val Met Glu Ile Ser Gln Thr
490                 495                 500                 505

CGT AAG AGC CTC TAC ATT GGC ACC GAT CAT CGC ATC AAG CAA ATC GAC      1830
Arg Lys Ser Leu Tyr Ile Gly Thr Asp His Arg Ile Lys Gln Ile Asp
                510                 515                 520

CTG GCC ATG TGC AAT CGC CGT TAC GAC AAC TGC TTC CGC TGC GTC CGT      1878
Leu Ala Met Cys Asn Arg Arg Tyr Asp Asn Cys Phe Arg Cys Val Arg
            525                 530                 535

GAT CCC TAC TGC GGC TGG GAT AAG GAG GCC AAT ACG TGC CGA CCG TAC      1926
Asp Pro Tyr Cys Gly Trp Asp Lys Glu Ala Asn Thr Cys Arg Pro Tyr
        540                 545                 550

GAG CTG GAT TTA CTG CAG GAT GTG GCC AAT GAA ACG AGT GAC ATT TGC      1974
Glu Leu Asp Leu Leu Gln Asp Val Ala Asn Glu Thr Ser Asp Ile Cys
    555                 560                 565

GAT TCG AGT GTG CTG AAA AAG AAG ATT GTG GTG ACC TAT GGC CAG AGT      2022
Asp Ser Ser Val Leu Lys Lys Lys Ile Val Val Thr Tyr Gly Gln Ser
570                 575                 580                 585

GTA CAT CTG GGC TGT TTC GTC AAA ATA CCC GAA GTG CTG AAG AAT GAG      2070
Val His Leu Gly Cys Phe Val Lys Ile Pro Glu Val Leu Lys Asn Glu
                590                 595                 600

CAA GTG ACC TGG TAT CAT CAC TCC AAG GAC AAG GGA CGC TAC GAG ATT      2118
Gln Val Thr Trp Tyr His His Ser Lys Asp Lys Gly Arg Tyr Glu Ile
            605                 610                 615

CGT TAC TCG CCG ACC AAA TAC ATT GAG ACC ACC GAA CGT GGC CTG GTT      2166
Arg Tyr Ser Pro Thr Lys Tyr Ile Glu Thr Thr Glu Arg Gly Leu Val
        620                 625                 630

GTG GTT TCC GTG AAC GAA GCC GAT GGT GGT CGG TAC GAT TGC CAT TTG      2214
Val Val Ser Val Asn Glu Ala Asp Gly Gly Arg Tyr Asp Cys His Leu
```

```
              635                 640                 645
GGC GGC TCG CTT TTG TGC AGC TAC AAC ATT ACA GTG GAT GCC CAC AGA      2262
Gly Gly Ser Leu Leu Cys Ser Tyr Asn Ile Thr Val Asp Ala His Arg
650                 655                 660                 665

TGC ACT CCG CCG AAC AAG AGT AAT GAC TAT CAG AAA ATC TAC TCG GAC      2310
Cys Thr Pro Pro Asn Lys Ser Asn Asp Tyr Gln Lys Ile Tyr Ser Asp
                670                 675                 680

TGG TGC CAC GAG TTC GAG AAA TAC AAA ACA GCA ATG AAG TCC TGG GAA      2358
Trp Cys His Glu Phe Glu Lys Tyr Lys Thr Ala Met Lys Ser Trp Glu
                685                 690                 695

AAG AAG CAA GGC CAA TGC TCG ACA CGG CAG AAC TTC AGC TGC AAT CAG      2406
Lys Lys Gln Gly Gln Cys Ser Thr Arg Gln Asn Phe Ser Cys Asn Gln
            700                 705                 710

CAT CCG AAT GAG ATT TTC CGT AAG CCC AAT GTC TGATATCACG AAGAGAGTAT    2459
His Pro Asn Glu Ile Phe Arg Lys Pro Asn Val
            715                 720

CGCCCTCAAA ATGCCGTCAT CGTCGTCCAA TCAATTTTAG TTAATCGAAA GCGAAGAGGA    2519

TAATAACAGT GCGGAATAGA AAGCCCAGGA CGAGAAGAAC TCATTATAAT CATTATTATC    2579

AGCGACATCA TCATAGACAT ACTTTCTTCA GCAATGAACA GAAAACTCTT CCTAAAGGAT    2639

TATGCATTTA CCGAAGCATT TACAATGCAT C                                   2670

(2) INFORMATION FOR SEQ ID NO: 62:

(i) SEQUENCE CHARACTERISTICS:
        (A) LENGTH: 724 amino acids
        (B) TYPE: amino acid
        (D) TOPOLOGY: linear (ii) MOLECULE TYPE: protein (xi) SEQUENCE DESCRIPTION: SEQ ID NO: 62:

Met Ser Leu Leu Gln Leu Ser Pro Leu Leu Ala Leu Leu Leu Leu
 1               5                  10                  15

Cys Ser Ser Val Ser Glu Thr Ala Ala Asp Tyr Glu Asn Thr Trp Asn
                20                  25                  30

Phe Tyr Tyr Glu Arg Pro Cys Cys Thr Gly Asn Asp Gln Gly Asn Asn
            35                  40                  45

Asn Tyr Gly Lys His Gly Ala Asp His Val Arg Glu Phe Asn Cys Gly
    50                  55                  60

Lys Leu Tyr Tyr Arg Thr Phe His Met Asn Glu Asp Arg Asp Thr Leu
65                  70                  75                  80

Tyr Val Gly Ala Met Asp Arg Val Phe Arg Val Asn Leu Gln Asn Ile
                85                  90                  95

Ser Ser Ser Asn Cys Asn Arg Asp Ala Ile Asn Leu Glu Pro Thr Arg
                100                 105                 110

Asp Asp Val Val Ser Cys Val Ser Lys Gly Lys Ser Gln Ile Phe Asp
            115                 120                 125

Cys Lys Asn His Val Arg Val Ile Gln Ser Met Asp Gln Gly Asp Arg
        130                 135                 140

Leu Tyr Val Cys Gly Thr Asn Ala His Asn Pro Lys Asp Tyr Val Ile
145                 150                 155                 160

Tyr Ala Asn Leu Thr His Leu Pro Arg Ser Glu Tyr Val Ile Gly Val
                165                 170                 175

Gly Leu Gly Ile Ala Lys Cys Pro Tyr Asp Pro Leu Asp Asn Ser Thr
            180                 185                 190

Ala Ile Tyr Val Glu Asn Gly Asn Pro Gly Gly Leu Pro Gly Leu Tyr
```

-continued

```
            195                 200                 205
Ser Gly Thr Asn Ala Glu Phe Thr Lys Ala Asp Thr Val Ile Phe Arg
    210                 215                 220

Thr Asp Leu Tyr Asn Thr Ser Ala Lys Arg Leu Glu Tyr Lys Phe Lys
225                 230                 235                 240

Arg Thr Leu Lys Tyr Asp Ser Lys Trp Leu Asp Lys Pro Asn Phe Val
                245                 250                 255

Gly Ser Phe Asp Ile Gly Glu Tyr Val Tyr Phe Phe Arg Glu Thr
                260                 265                 270

Ala Val Glu Tyr Ile Asn Cys Gly Lys Ala Val Tyr Ser Arg Ile Ala
            275                 280                 285

Arg Val Cys Lys Lys Asp Val Gly Gly Lys Asn Leu Leu Ala His Asn
        290                 295                 300

Trp Ala Thr Tyr Leu Lys Ala Arg Leu Asn Cys Ser Ile Ser Gly Glu
305                 310                 315                 320

Phe Pro Phe Tyr Phe Asn Glu Ile Gln Ser Val Tyr Gln Leu Pro Ser
                325                 330                 335

Asp Lys Ser Arg Phe Ala Thr Phe Thr Thr Ser Thr Asn Gly Leu
                340                 345                 350

Ile Gly Ser Ala Val Cys Ser Phe His Ile Asn Glu Ile Gln Ala Ala
            355                 360                 365

Phe Asn Gly Lys Phe Lys Glu Gln Ser Ser Asn Ser Ala Trp Leu
    370                 375                 380

Pro Val Leu Asn Ser Arg Val Pro Glu Pro Arg Pro Gly Thr Cys Val
385                 390                 395                 400

Asn Asp Thr Ser Asn Leu Pro Asp Thr Val Leu Asn Phe Ile Arg Ser
                405                 410                 415

His Pro Leu Met Asp Lys Ala Val Asn His Glu His Asn Asn Pro Val
                420                 425                 430

Tyr Tyr Lys Arg Asp Leu Val Phe Thr Lys Leu Val Val Asp Lys Ile
            435                 440                 445

Arg Ile Asp Ile Leu Asn Gln Glu Tyr Ile Val Tyr Tyr Val Gly Thr
    450                 455                 460

Asn Leu Gly Arg Ile Tyr Lys Ile Val Gln Tyr Tyr Arg Asn Gly Glu
465                 470                 475                 480

Ser Leu Ser Lys Leu Leu Asp Ile Phe Glu Val Ala Pro Asn Glu Ala
                485                 490                 495

Ile Gln Val Met Glu Ile Ser Gln Thr Arg Lys Ser Leu Tyr Ile Gly
            500                 505                 510

Thr Asp His Arg Ile Lys Gln Ile Asp Leu Ala Met Cys Asn Arg Arg
        515                 520                 525

Tyr Asp Asn Cys Phe Arg Cys Val Arg Asp Pro Tyr Cys Gly Trp Asp
    530                 535                 540

Lys Glu Ala Asn Thr Cys Arg Pro Tyr Glu Leu Asp Leu Leu Gln Asp
545                 550                 555                 560

Val Ala Asn Glu Thr Ser Asp Ile Cys Asp Ser Ser Val Leu Lys Lys
                565                 570                 575

Lys Ile Val Val Thr Tyr Gly Gln Ser Val His Leu Gly Cys Phe Val
            580                 585                 590

Lys Ile Pro Glu Val Leu Lys Asn Glu Gln Val Thr Trp Tyr His His
        595                 600                 605

Ser Lys Asp Lys Gly Arg Tyr Glu Ile Arg Tyr Ser Pro Thr Lys Tyr
    610                 615                 620
```

```
Ile Glu Thr Thr Glu Arg Gly Leu Val Val Ser Val Asn Glu Ala
625                 630                 635                 640

Asp Gly Gly Arg Tyr Asp Cys His Leu Gly Gly Ser Leu Leu Cys Ser
                645                 650                 655

Tyr Asn Ile Thr Val Asp Ala His Arg Cys Thr Pro Pro Asn Lys Ser
            660                 665                 670

Asn Asp Tyr Gln Lys Ile Tyr Ser Asp Trp Cys His Glu Phe Glu Lys
            675                 680                 685

Tyr Lys Thr Ala Met Lys Ser Trp Glu Lys Lys Gln Gly Gln Cys Ser
            690                 695                 700

Thr Arg Gln Asn Phe Ser Cys Asn Gln His Pro Asn Glu Ile Phe Arg
705                 710                 715                 720

Lys Pro Asn Val
```

(2) INFORMATION FOR SEQ ID NO: 63:

(i) SEQUENCE CHARACTERISTICS:
        (A) LENGTH: 2504 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 355..2493

(xi) SEQUENCE DESCRIPTION: SEQ ID NO: 63:

```
GGCCGGTCGA CCACGAGCGA AGTTTAGTAT CAAGTTGAGA GTTTGTTTGG AGCGTAGTTT      60

ACGGAGCGTA CATTTAAATT TGCGGACAAA TCGTGTTTTG GTGCTTCTCT GTGGATTGTT     120

GTGTTCTTGA AGATGCTTCC CTTGGTTTTC GGATAAGCTT TCCTGTGGAT TGTTGTGTTC     180

TTGAAGATGC TTCCCTTGGT TTTCGGATAA GCTTTCCAGC GTGGTTTCAG CCTCGGCTTG     240

TTTGGACCCC GACATAATCT TCGAACTACA ATGAAGAGGA AATTTTGAAA CGCGTTTCAG     300

ACGCGTACAA TCGACAAAAT GTTTGGTTTC CAATTGATCT TGCAATGTAG CTAC ATG       357
                                                              Met
                                                                1

GTG GTG AAG ATC TTG GTT TGG TCG ATA TGT CTG ATA GCG CTG TGT CAT       405
Val Val Lys Ile Leu Val Trp Ser Ile Cys Leu Ile Ala Leu Cys His
            5                  10                  15

GCT TGG ATG CCG GAT AGT TCT TCC AAA TTA ATA AAC CAT TTT AAA TCA       453
Ala Trp Met Pro Asp Ser Ser Ser Lys Leu Ile Asn His Phe Lys Ser
        20                  25                  30

GTT GAA AGT AAA AGC TTT ACC GGG AAC GCC ACG TTC CCT GAT CAC TTT       501
Val Glu Ser Lys Ser Phe Thr Gly Asn Ala Thr Phe Pro Asp His Phe
    35                  40                  45

ATT GTC TTG AAT CAA GAC GAA ACT TCG ATA TTA GTA GGC GGT AGA AAT       549
Ile Val Leu Asn Gln Asp Glu Thr Ser Ile Leu Val Gly Gly Arg Asn
50                  55                  60                  65

AGG GTT TAC AAT TTA AGT ATA TTC GAC CTC AGT GAG CGT AAA GGG GGG       597
Arg Val Tyr Asn Leu Ser Ile Phe Asp Leu Ser Glu Arg Lys Gly Gly
                70                  75                  80

CGA ATC GAC TGG CCA TCG TCC GAT GCA CAT GGC CAG TTG TGT ATA TTG       645
Arg Ile Asp Trp Pro Ser Ser Asp Ala His Gly Gln Leu Cys Ile Leu
            85                  90                  95

AAA GGG AAA ACG GAC GAC GAC TGC CAA AAT TAC ATT AGA ATA CTG TAC       693
Lys Gly Lys Thr Asp Asp Asp Cys Gln Asn Tyr Ile Arg Ile Leu Tyr
```

-continued

|  |  |
|---|---|
| TCT TCA GAA CCG GGG AAA TTA GTT ATT TGC GGG ACC AAT TCG TAC AAA<br>Ser Ser Glu Pro Gly Lys Leu Val Ile Cys Gly Thr Asn Ser Tyr Lys<br>     115                120                   125 | 741 |
| CCC CTC TGT CGG ACG TAC GCA TTT AAG GAG GGA AAG TAC CTG GTT GAG<br>Pro Leu Cys Arg Thr Tyr Ala Phe Lys Glu Gly Lys Tyr Leu Val Glu<br>130               135               140              145 | 789 |
| AAA GAA GTA GAA GGG ATA GGC TTG TGT CCA TAC AAT CCG GAA CAC AAC<br>Lys Glu Val Glu Gly Ile Gly Leu Cys Pro Tyr Asn Pro Glu His Asn<br>               150               155              160 | 837 |
| AGC ACA TCT GTC TCC TAC AAT GGC CAA TTA TTT TCA GCG ACG GTC GCC<br>Ser Thr Ser Val Ser Tyr Asn Gly Gln Leu Phe Ser Ala Thr Val Ala<br>           165               170              175 | 885 |
| GAC TTT TCC GGG GGC GAC CCT CTC ATA TAC AGG GAG CCC CAG CGC ACC<br>Asp Phe Ser Gly Gly Asp Pro Leu Ile Tyr Arg Glu Pro Gln Arg Thr<br>        180               185              190 | 933 |
| GAA CTC TCA GAT CTC AAA CAA CTG AAC GCA CCG AAT TTC GTA AAC TCG<br>Glu Leu Ser Asp Leu Lys Gln Leu Asn Ala Pro Asn Phe Val Asn Ser<br>195               200               205 | 981 |
| GTG GCC TAT GGC GAC TAC ATA TTC TTC TTC TAC CGT GAA ACC GCC GTC<br>Val Ala Tyr Gly Asp Tyr Ile Phe Phe Phe Tyr Arg Glu Thr Ala Val<br>210               215              220              225 | 1029 |
| GAG TAC ATG AAC TGC GGA AAA GTC ATC TAC TCG CGG GTC GCC AGG GTG<br>Glu Tyr Met Asn Cys Gly Lys Val Ile Tyr Ser Arg Val Ala Arg Val<br>               230              235             240 | 1077 |
| TGC AAG GAC GAC AAA GGG GGC CCT CAC CAG TCA CGC GAC CGC TGG ACG<br>Cys Lys Asp Asp Lys Gly Gly Pro His Gln Ser Arg Asp Arg Trp Thr<br>           245              250              255 | 1125 |
| TCG TTC CTC AAA GCA CGT CTC AAT TGT TCA ATT CCC GGC GAG TAC CCC<br>Ser Phe Leu Lys Ala Arg Leu Asn Cys Ser Ile Pro Gly Glu Tyr Pro<br>        260               265              270 | 1173 |
| TTT TAC TTT GAT GAA ATC CAA TCA ACA AGT GAT ATA GTC GAG GGT CGG<br>Phe Tyr Phe Asp Glu Ile Gln Ser Thr Ser Asp Ile Val Glu Gly Arg<br>275               280               285 | 1221 |
| TAC AAT TCC GAC GAC AGC AAA AAG ATC ATT TAT GGA ATC CTC ACA ACT<br>Tyr Asn Ser Asp Asp Ser Lys Lys Ile Ile Tyr Gly Ile Leu Thr Thr<br>290               295              300              305 | 1269 |
| CCA GTT AAT GCC ATC GGC GGC TCG GCC ATT TGC GCG TAT CAA ATG GCC<br>Pro Val Asn Ala Ile Gly Gly Ser Ala Ile Cys Ala Tyr Gln Met Ala<br>               310              315             320 | 1317 |
| GAC ATC TTG CGC GTG TTT GAA GGG AGC TTC AAG CAC CAA GAG ACG ATC<br>Asp Ile Leu Arg Val Phe Glu Gly Ser Phe Lys His Gln Glu Thr Ile<br>           325              330              335 | 1365 |
| AAC TCG AAC TGG CTC CCC GTG CCC CAG AAC CTA GTC CCT GAA CCC AGG<br>Asn Ser Asn Trp Leu Pro Val Pro Gln Asn Leu Val Pro Glu Pro Arg<br>        340               345              350 | 1413 |
| CCC GGG CAG TGC GTA CGC GAC AGC AGG ATC CTG CCC GAC AAG AAC GTC<br>Pro Gly Gln Cys Val Arg Asp Ser Arg Ile Leu Pro Asp Lys Asn Val<br>355               360               365 | 1461 |
| AAC TTT ATT AAG ACC CAC TCT TTG ATG GAG GAC GTT CCG GCT CTT TTC<br>Asn Phe Ile Lys Thr His Ser Leu Met Glu Asp Val Pro Ala Leu Phe<br>370               375              380              385 | 1509 |
| GGA AAA CCA GTT CTG GTC CGA GTG AGT CTG CAG TAT CGG TTT ACA GCC<br>Gly Lys Pro Val Leu Val Arg Val Ser Leu Gln Tyr Arg Phe Thr Ala<br>           390              395              400 | 1557 |
| ATA ACA GTG GAT CCA CAA GTG AAA ACA ATC AAT AAT CAG TAT CTC GAT<br>Ile Thr Val Asp Pro Gln Val Lys Thr Ile Asn Asn Gln Tyr Leu Asp<br>           405              410              415 | 1605 |
| GTT TTG TAT ATC GGA ACA GAT GAT GGG AAG GTA CTA AAA GCT GTT AAT | 1653 |

```
                Val Leu Tyr Ile Gly Thr Asp Asp Gly Lys Val Leu Lys Ala Val Asn
                        420                 425                 430

ATA CCA AAG CGA CAC GCT AAA GCG TTG TTA TAT CGA AAA TAC CGT ACA         1701
Ile Pro Lys Arg His Ala Lys Ala Leu Leu Tyr Arg Lys Tyr Arg Thr
        435                 440                 445

TCC GTA CAT CCG CAC GGA GCT CCC GTA AAA CAG CTG AAG ATC GCT CCC         1749
Ser Val His Pro His Gly Ala Pro Val Lys Gln Leu Lys Ile Ala Pro
450                 455                 460                 465

GGT TAT GGC AAA GTT GTG GTG GTC GGG AAA GAC GAA ATC AGA CTT GCT         1797
Gly Tyr Gly Lys Val Val Val Val Gly Lys Asp Glu Ile Arg Leu Ala
                470                 475                 480

AAT CTC AAC CAT TGT GCA AGC AAA ACG CGG TGC AAG GAC TGT GTG GAA         1845
Asn Leu Asn His Cys Ala Ser Lys Thr Arg Cys Lys Asp Cys Val Glu
            485                 490                 495

CTG CAA GAC CCA CAT TGC GCC TGG GAC GCC AAA CAA AAC CTG TGT GTC         1893
Leu Gln Asp Pro His Cys Ala Trp Asp Ala Lys Gln Asn Leu Cys Val
        500                 505                 510

AGC ATT GAC ACC GTC ACT TCG TAT CGC TTC CTG ATC CAG GAC GTA GTT         1941
Ser Ile Asp Thr Val Thr Ser Tyr Arg Phe Leu Ile Gln Asp Val Val
    515                 520                 525

CGC GGC GAC GAC AAC AAA TGT TGG TCG CCG CAA ACA GAC AAA AAG ACT         1989
Arg Gly Asp Asp Asn Lys Cys Trp Ser Pro Gln Thr Asp Lys Lys Thr
530                 535                 540                 545

GTG ATT AAG AAT AAG CCC AGC GAG GTT GAG AAC GAG ATT ACG AAC TCC         2037
Val Ile Lys Asn Lys Pro Ser Glu Val Glu Asn Glu Ile Thr Asn Ser
                550                 555                 560

ATT GAC GAA AAG GAT CTC GAT TCA AGC GAT CCG CTC ATC AAA ACT GGT         2085
Ile Asp Glu Lys Asp Leu Asp Ser Ser Asp Pro Leu Ile Lys Thr Gly
            565                 570                 575

CTC GAT GAC GAT TCC GAT TGT GAT CCA GTC AGC GAG AAC AGC ATA GGC         2133
Leu Asp Asp Asp Ser Asp Cys Asp Pro Val Ser Glu Asn Ser Ile Gly
        580                 585                 590

GGA TGC GCC GTC CGC CAG CAA CTT GTT ATA TAC ACA GCT GGG ACT CTA         2181
Gly Cys Ala Val Arg Gln Gln Leu Val Ile Tyr Thr Ala Gly Thr Leu
    595                 600                 605

CAC ATT GTC GTG GTC GTC GTC AGC ATC GTG GGT TTA TTT TCT TGG CTT         2229
His Ile Val Val Val Val Val Ser Ile Val Gly Leu Phe Ser Trp Leu
610                 615                 620                 625

TAT AGC GGG TTA TCT GTT TTC GCA AAA TTT CAC TCG GAT TCG CAA TAT         2277
Tyr Ser Gly Leu Ser Val Phe Ala Lys Phe His Ser Asp Ser Gln Tyr
                630                 635                 640

CCT GAG GCG CCG TTT ATA GAG CAG CAC AAT CAT TTG GAA AGA TTA AGC         2325
Pro Glu Ala Pro Phe Ile Glu Gln His Asn His Leu Glu Arg Leu Ser
            645                 650                 655

GCC AAC CAG ACG GGG TAT TTG ACT CCG AGG GCC AAT AAA GCG GTC AAT         2373
Ala Asn Gln Thr Gly Tyr Leu Thr Pro Arg Ala Asn Lys Ala Val Asn
        660                 665                 670

TTG GTG GTG AAG GTG TCT AGT AGC ACG CCG CGG CCG AAA AAG GAC AAT         2421
Leu Val Val Lys Val Ser Ser Ser Thr Pro Arg Pro Lys Lys Asp Asn
    675                 680                 685

CTC GAT GTC AGC AAA GAC TTG AAC ATT GCG AGT GAC GGG ACT TTG CAA         2469
Leu Asp Val Ser Lys Asp Leu Asn Ile Ala Ser Asp Gly Thr Leu Gln
690                 695                 700                 705

AAA ATC AAG AAG ACT TAC ATT TAGTGCGACT TTTT                             2504
Lys Ile Lys Lys Thr Tyr Ile
                710
```

(2) INFORMATION FOR SEQ ID NO: 64:

(i) SEQUENCE CHARACTERISTICS:

(A) LENGTH: 712 amino acids
(B) TYPE: amino acid
(D) TOPOLOGY: linear (ii) MOLECULE TYPE: protein (xi) SEQUENCE DESCRIPTION: SEQ ID NO: 64:

```
Met Val Val Lys Ile Leu Val Trp Ser Ile Cys Leu Ile Ala Leu Cys
 1               5                  10                  15

His Ala Trp Met Pro Asp Ser Ser Lys Leu Ile Asn His Phe Lys
             20                  25                  30

Ser Val Glu Ser Lys Ser Phe Thr Gly Asn Ala Thr Phe Pro Asp His
         35                  40                  45

Phe Ile Val Leu Asn Gln Asp Glu Thr Ser Ile Leu Val Gly Gly Arg
     50                  55                  60

Asn Arg Val Tyr Asn Leu Ser Ile Phe Asp Leu Ser Glu Arg Lys Gly
 65                  70                  75                  80

Gly Arg Ile Asp Trp Pro Ser Ser Asp Ala His Gly Gln Leu Cys Ile
                 85                  90                  95

Leu Lys Gly Lys Thr Asp Asp Cys Gln Asn Tyr Ile Arg Ile Leu
                100                 105                 110

Tyr Ser Ser Glu Pro Gly Lys Leu Val Ile Cys Gly Thr Asn Ser Tyr
             115                 120                 125

Lys Pro Leu Cys Arg Thr Tyr Ala Phe Lys Glu Gly Lys Tyr Leu Val
         130                 135                 140

Glu Lys Glu Val Glu Gly Ile Gly Leu Cys Pro Tyr Asn Pro Glu His
145                 150                 155                 160

Asn Ser Thr Ser Val Ser Tyr Asn Gly Gln Leu Phe Ser Ala Thr Val
                 165                 170                 175

Ala Asp Phe Ser Gly Gly Asp Pro Leu Ile Tyr Arg Glu Pro Gln Arg
             180                 185                 190

Thr Glu Leu Ser Asp Leu Lys Gln Leu Asn Ala Pro Asn Phe Val Asn
         195                 200                 205

Ser Val Ala Tyr Gly Asp Tyr Ile Phe Phe Phe Tyr Arg Glu Thr Ala
210                 215                 220

Val Glu Tyr Met Asn Cys Gly Lys Val Ile Tyr Ser Arg Val Ala Arg
225                 230                 235                 240

Val Cys Lys Asp Asp Lys Gly Gly Pro His Gln Ser Arg Asp Arg Trp
                 245                 250                 255

Thr Ser Phe Leu Lys Ala Arg Leu Asn Cys Ser Ile Pro Gly Glu Tyr
             260                 265                 270

Pro Phe Tyr Phe Asp Glu Ile Gln Ser Thr Ser Asp Ile Val Glu Gly
         275                 280                 285

Arg Tyr Asn Ser Asp Asp Ser Lys Lys Ile Ile Tyr Gly Ile Leu Thr
290                 295                 300

Thr Pro Val Asn Ala Ile Gly Gly Ser Ala Ile Cys Ala Tyr Gln Met
305                 310                 315                 320

Ala Asp Ile Leu Arg Val Phe Glu Gly Ser Phe Lys His Gln Glu Thr
                 325                 330                 335

Ile Asn Ser Asn Trp Leu Pro Val Pro Gln Asn Leu Val Pro Glu Pro
             340                 345                 350

Arg Pro Gly Gln Cys Val Arg Asp Ser Arg Ile Leu Pro Asp Lys Asn
         355                 360                 365

Val Asn Phe Ile Lys Thr His Ser Leu Met Glu Asp Val Pro Ala Leu
370                 375                 380
```

-continued

Phe Gly Lys Pro Val Leu Val Arg Val Ser Leu Gln Tyr Arg Phe Thr
385                 390                 395                 400

Ala Ile Thr Val Asp Pro Gln Val Lys Thr Ile Asn Asn Gln Tyr Leu
            405                 410                 415

Asp Val Leu Tyr Ile Gly Thr Asp Asp Gly Lys Val Leu Lys Ala Val
                420                 425                 430

Asn Ile Pro Lys Arg His Ala Lys Ala Leu Leu Tyr Arg Lys Tyr Arg
            435                 440                 445

Thr Ser Val His Pro His Gly Ala Pro Val Lys Gln Leu Lys Ile Ala
450                 455                 460

Pro Gly Tyr Gly Lys Val Val Val Gly Lys Asp Glu Ile Arg Leu
465                 470                 475                 480

Ala Asn Leu Asn His Cys Ala Ser Lys Thr Arg Cys Lys Asp Cys Val
                485                 490                 495

Glu Leu Gln Asp Pro His Cys Ala Trp Asp Ala Lys Gln Asn Leu Cys
            500                 505                 510

Val Ser Ile Asp Thr Val Thr Ser Tyr Arg Phe Leu Ile Gln Asp Val
            515                 520                 525

Val Arg Gly Asp Asp Asn Lys Cys Trp Ser Pro Gln Thr Asp Lys Lys
530                 535                 540

Thr Val Ile Lys Asn Lys Pro Ser Glu Val Glu Asn Glu Ile Thr Asn
545                 550                 555                 560

Ser Ile Asp Glu Lys Asp Leu Asp Ser Ser Asp Pro Leu Ile Lys Thr
                565                 570                 575

Gly Leu Asp Asp Asp Ser Asp Cys Asp Pro Val Ser Glu Asn Ser Ile
            580                 585                 590

Gly Gly Cys Ala Val Arg Gln Gln Leu Val Ile Tyr Thr Ala Gly Thr
            595                 600                 605

Leu His Ile Val Val Val Val Ser Ile Val Gly Leu Phe Ser Trp
610                 615                 620

Leu Tyr Ser Gly Leu Ser Val Phe Ala Lys Phe His Ser Asp Ser Gln
625                 630                 635                 640

Tyr Pro Glu Ala Pro Phe Ile Glu Gln His Asn His Leu Glu Arg Leu
            645                 650                 655

Ser Ala Asn Gln Thr Gly Tyr Leu Thr Pro Arg Ala Asn Lys Ala Val
            660                 665                 670

Asn Leu Val Val Lys Val Ser Ser Thr Pro Arg Pro Lys Lys Asp
            675                 680                 685

Asn Leu Asp Val Ser Lys Asp Leu Asn Ile Ala Ser Asp Gly Thr Leu
690                 695                 700

Gln Lys Ile Lys Lys Thr Tyr Ile
705                 710

(2) INFORMATION FOR SEQ ID NO: 65:

(i) SEQUENCE CHARACTERISTICS:
        (A) LENGTH: 369 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..369

(xi) SEQUENCE DESCRIPTION: SEQ ID NO: 65:

| | | | | | | | | | | | | | | | | |
|---|---|---|---|---|---|---|---|---|---|---|---|---|---|---|---|---|
| ATG | ATT | TAT | TTA | TAC | ACG | GCG | GAT | AAC | GTA | ATT | CCA | AAA | GAT | GGT | TTA | 48 |
| Met | Ile | Tyr | Leu | Tyr | Thr | Ala | Asp | Asn | Val | Ile | Pro | Lys | Asp | Gly | Leu | |
| 1 | | | | 5 | | | | | 10 | | | | | 15 | | |
| CAA | GGA | GCA | TTT | GTC | GAT | AAA | GAC | GGT | ACT | TAT | GAC | AAA | GTT | TAC | ATT | 96 |
| Gln | Gly | Ala | Phe | Val | Asp | Lys | Asp | Gly | Thr | Tyr | Asp | Lys | Val | Tyr | Ile | |
| | | | 20 | | | | | 25 | | | | | 30 | | | |
| CTT | TTC | ACT | GTT | ACT | ATC | GGC | TCA | AAG | AGA | ATT | GTT | AAA | ATT | CCG | TAT | 144 |
| Leu | Phe | Thr | Val | Thr | Ile | Gly | Ser | Lys | Arg | Ile | Val | Lys | Ile | Pro | Tyr | |
| | | 35 | | | | | 40 | | | | | 45 | | | | |
| ATA | GCA | CAA | ATG | TGC | TTA | AAC | GAC | GAA | TGT | GGT | CCA | TCA | TCA | TTG | TCT | 192 |
| Ile | Ala | Gln | Met | Cys | Leu | Asn | Asp | Glu | Cys | Gly | Pro | Ser | Ser | Leu | Ser | |
| 50 | | | | | 55 | | | | | 60 | | | | | | |
| AGT | CAT | AGA | TGG | TCG | ACG | TTG | CTC | AAA | GTC | GAA | TTA | GAA | TGT | GAC | ATC | 240 |
| Ser | His | Arg | Trp | Ser | Thr | Leu | Leu | Lys | Val | Glu | Leu | Glu | Cys | Asp | Ile | |
| 65 | | | | | 70 | | | | | 75 | | | | | 80 | |
| GAC | GGA | AGA | AGT | TAT | AGT | CAA | ATT | AAT | CAT | TCT | AAA | ACT | ATA | AAA | CAG | 288 |
| Asp | Gly | Arg | Ser | Tyr | Ser | Gln | Ile | Asn | His | Ser | Lys | Thr | Ile | Lys | Gln | |
| | | | | 85 | | | | | 90 | | | | | 95 | | |
| ATA | ATG | ATA | CGA | TAC | TAT | ATG | TAT | TCT | TTG | ATA | GTC | CTT | TTC | CAA | GTC | 336 |
| Ile | Met | Ile | Arg | Tyr | Tyr | Met | Tyr | Ser | Leu | Ile | Val | Leu | Phe | Gln | Val | |
| | | | 100 | | | | | 105 | | | | | 110 | | | |
| CGC | ATT | ATG | TAC | CTA | TTC | TAT | GAA | TAC | CAT | TAA | | | | | | 369 |
| Arg | Ile | Met | Tyr | Leu | Phe | Tyr | Glu | Tyr | His | | | | | | | |
| | | 115 | | | | | 120 | | | | | | | | | |

(2) INFORMATION FOR SEQ ID NO: 66:

(i) SEQUENCE CHARACTERISTICS:
        (A) LENGTH: 122 amino acids
        (B) TYPE: amino acid
        (D) TOPOLOGY: linear (ii) MOLECULE TYPE: protein (xi) SEQUENCE DESCRIPTION: SEQ ID NO: 66:

| | | | | | | | | | | | | | | | |
|---|---|---|---|---|---|---|---|---|---|---|---|---|---|---|---|
| Met | Ile | Tyr | Leu | Tyr | Thr | Ala | Asp | Asn | Val | Ile | Pro | Lys | Asp | Gly | Leu |
| 1 | | | | 5 | | | | | 10 | | | | | 15 | |
| Gln | Gly | Ala | Phe | Val | Asp | Lys | Asp | Gly | Thr | Tyr | Asp | Lys | Val | Tyr | Ile |
| | | | 20 | | | | | 25 | | | | | 30 | | |
| Leu | Phe | Thr | Val | Thr | Ile | Gly | Ser | Lys | Arg | Ile | Val | Lys | Ile | Pro | Tyr |
| | | 35 | | | | | 40 | | | | | 45 | | | |
| Ile | Ala | Gln | Met | Cys | Leu | Asn | Asp | Glu | Cys | Gly | Pro | Ser | Ser | Leu | Ser |
| 50 | | | | | 55 | | | | | 60 | | | | | |
| Ser | His | Arg | Trp | Ser | Thr | Leu | Leu | Lys | Val | Glu | Leu | Glu | Cys | Asp | Ile |
| 65 | | | | | 70 | | | | | 75 | | | | | 80 |
| Asp | Gly | Arg | Ser | Tyr | Ser | Gln | Ile | Asn | His | Ser | Lys | Thr | Ile | Lys | Gln |
| | | | | 85 | | | | | 90 | | | | | 95 | |
| Ile | Met | Ile | Arg | Tyr | Tyr | Met | Tyr | Ser | Leu | Ile | Val | Leu | Phe | Gln | Val |
| | | | 100 | | | | | 105 | | | | | 110 | | |
| Arg | Ile | Met | Tyr | Leu | Phe | Tyr | Glu | Tyr | His | | | | | | |
| | | 115 | | | | | 120 | | | | | | | | |

(2) INFORMATION FOR SEQ ID NO: 67:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 67:

Asp Cys Gln Asn Tyr Ile
1               5

(2) INFORMATION FOR SEQ ID NO: 68:

(i) SEQUENCE CHARACTERISTICS:
            (A) LENGTH: 8 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..8
            (D) OTHER INFORMATION: /label= SEQ68
                  /note= "Xaa denotes N or G at residue #4; and A or S
                  at residue #5"

(xi) SEQUENCE DESCRIPTION: SEQ ID NO: 68:

Cys Gly Thr Xaa Xaa Xaa Xaa Pro
1               5

(2) INFORMATION FOR SEQ ID NO: 69:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..7
            (D) OTHER INFORMATION: /label= SEQ69
                  /note= "Xaa denotes S or C at residue #3"

(xi) SEQUENCE DESCRIPTION: SEQ ID NO: 69:

Gly Xaa Xaa Pro Tyr Asp Pro
1               5

(2) INFORMATION FOR SEQ ID NO: 70:

(i) SEQUENCE CHARACTERISTICS:
            (A) LENGTH: 7 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..7
            (D) OTHER INFORMATION: /label= SEQ70
                  /note= "Xaa denotes V, N or A"

(xi) SEQUENCE DESCRIPTION: SEQ ID NO: 70:

Leu Tyr Ser Gly Thr Xaa Ala
1               5

(2) INFORMATION FOR SEQ ID NO: 71:

(i) SEQUENCE CHARACTERISTICS:
            (A) LENGTH: 7 amino acids (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 71:

Leu Asn Ala Pro Asn Phe Val
1               5

(2) INFORMATION FOR SEQ ID NO: 72:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ72
            /note= "Xaa denotes V or I"

(xi) SEQUENCE DESCRIPTION: SEQ ID NO: 72:

Arg Xaa Ala Arg Val Cys Lys (2) INFORMATION FOR SEQ ID NO: 73:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= SEQ73
            /note= "Xaa denotes T or A at residue #2; T or S
            at residue #3; F or Y at residue #4; and A or S at
            residue #7"

(xi) SEQUENCE DESCRIPTION: SEQ ID NO: 73:

Trp Xaa Xaa Xaa Leu Lys Xaa Arg Leu
1               5

(2) INFORMATION FOR SEQ ID NO: 74:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..9
        (D) OTHER INFORMATION: /label= SEQ74
            /note= "Xaa denotes N or D"

(xi) SEQUENCE DESCRIPTION: SEQ ID NO: 74:

Pro Phe Tyr Phe Xaa Glu Ile Gln Ser
1               5

(2) INFORMATION FOR SEQ ID NO: 75:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ75
            /note= "Xaa denotes F or Y at residue #7"

(xi) SEQUENCE DESCRIPTION: SEQ ID NO: 75:

Gly Ser Ala Val Cys Xaa Xaa
1               5

(2) INFORMATION FOR SEQ ID NO: 76:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ76
            /note= "Xaa denotes P or A at residue #6"

(xi) SEQUENCE DESCRIPTION: SEQ ID NO: 76:

Asn Ser Asn Trp Leu Xaa Val
1               5

(2) INFORMATION FOR SEQ ID NO: 77:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ77
            /note= "Xaa denotes E or D at residue #2; T, Q or S
            at residue #7"

(xi) SEQUENCE DESCRIPTION: SEQ ID NO: 77:

Pro Xaa Pro Arg Pro Gly Xaa Cys
1               5

(2) INFORMATION FOR SEQ ID NO: 78:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide (B) LOCATION: 1..7
        (D) OTHER INFORMATION: /label= SEQ78
            /note= "Xaa denotes A or G"

(xi) SEQUENCE DESCRIPTION: SEQ ID NO: 78:

Asp Pro Tyr Cys Xaa Trp Asp
1               5

(2) INFORMATION FOR SEQ ID NO: 79:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ79
            /note= "Xaa denotes N or G at residue #4; A or S at
            residue #5; Y, F, H or G at residue #6; and K, R, H, N or
            Q at residue #7"

(xi) SEQUENCE DESCRIPTION: SEQ ID NO: 79:

Cys Gly Thr Xaa Xaa Xaa Xaa
1               5

(2) INFORMATION FOR SEQ ID NO: 80:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ80
            /note= "Xaa denotes N or G at residue #4; A, S or N
            at residue #5; Y, F or H at residue #6; and K, R, H, N or
            Q at residue #7"

(xi) SEQUENCE DESCRIPTION: SEQ ID NO: 80:

Cys Gly Thr Xaa Xaa Xaa Xaa
1               5

(2) INFORMATION FOR SEQ ID NO: 81:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ81
            /note= "Xaa denotes N or G at residue #4; and A or S
            at residue #5"

(xi) SEQUENCE DESCRIPTION: SEQ ID NO: 81:

Cys Gly Thr Xaa Xaa Xaa Xaa Pro
1               5

(2) INFORMATION FOR SEQ ID NO: 82:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ82
            /note= "Xaa denotes K, F or Y at residue #2; F or Y
            at residue #4; F, Y, I or L at residue #5; F, Y or I at
            residue #6; and F or Y at residue #7"

(xi) SEQUENCE DESCRIPTION: SEQ ID NO: 82:

Asp Xaa Val Xaa Xaa Xaa Xaa
1                5

(2) INFORMATION FOR SEQ ID NO: 83:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ83
            /note= "Xaa denotes V or I at residue #1; F or Y
            at residue #2; F, Y or L at residue #3; F, Y, I or L at
            residue #4; R or T at residue #6; and T or N at residue
            #8"

(xi) SEQUENCE DESCRIPTION: SEQ ID NO: 83:

Xaa Xaa Xaa Xaa Phe Xaa Xaa Xaa
1                5

(2) INFORMATION FOR SEQ ID NO: 84:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ84
            /note= "Xaa denotes V or I at residue #1; F or Y
            at residue #2; F, Y, I or L at residue #3; F, Y or I at
            residue #4; R or T at residue #6; and T or N at residue
            #8"

(xi) SEQUENCE DESCRIPTION: SEQ ID NO: 84:

Xaa Xaa Xaa Xaa Phe Xaa Xaa Xaa
1                5

(2) INFORMATION FOR SEQ ID NO: 85:

(i) SEQUENCE CHARACTERISTICS:

```
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ85
            /note= "Xaa denotes V or I at residue #1; F or Y
            at residue #2; F, Y, I or L at residue #3; F, Y, I or L at
            residue #4; and T or N at residue #8"

(xi) SEQUENCE DESCRIPTION: SEQ ID NO: 85:

Xaa Xaa Xaa Xaa Phe Arg Xaa Xaa
1               5

(2) INFORMATION FOR SEQ ID NO: 86:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ86
            /note= "Xaa denotes V or I at residue #1; F or Y
            at residue #2; F, Y or L at residue #3; F, Y, I or L at
            residue #4; F or Y at residue #5; R or T at residue #6, E,
            D or V at residue #7; and T or N at residue #8"

(xi) SEQUENCE DESCRIPTION: SEQ ID NO: 86:

Xaa Xaa Xaa Xaa Xaa Xaa Xaa Xaa
1               5

(2) INFORMATION FOR SEQ ID NO: 87:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ87
            /note= "Xaa denotes R, K or N at residue #1; T or A
            at residue #3; T, A or S at residue #4; F, Y or L at
            residue #5; and K or R at residue #7"

(xi) SEQUENCE DESCRIPTION: SEQ ID NO: 87:

Xaa Trp xaa Xaa Xaa Leu Xaa
1               5

(2) INFORMATION FOR SEQ ID NO: 88:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide
```

```
    (ix) FEATURE:
         (A) NAME/KEY: Peptide
         (B) LOCATION: 1..9
         (D) OTHER INFORMATION: /label= SEQ88
             /note= "Xaa denotes T or A at residue #2; T, A or S
             at residue #3; F, Y or L at residue #4; A, S, V, I or L at
             residue #7"

(xi) SEQUENCE DESCRIPTION: SEQ ID NO: 88:

Trp Xaa Xaa Xaa Leu Lys Xaa Xaa Leu
1               5

(2) INFORMATION FOR SEQ ID NO: 89:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..9
         (D) OTHER INFORMATION: /label= SEQ89
             /note= "Xaa denotes T, A or S at residue #2; T, A or S
             at residue #3; F, Y or L at residue #4; A, S, I or L at
             residue #7"

(xi) SEQUENCE DESCRIPTION: SEQ ID NO: 89:

Trp Xaa Xaa Xaa Leu Lys Xaa Xaa Leu
1               5

(2) INFORMATION FOR SEQ ID NO: 90:

(i) SEQUENCE CHARACTERISTICS:
         (A) LENGTH: 11 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..11
         (D) OTHER INFORMATION: /label= SEQ90
             /note= "Xaa denotes T or A at residue #2; and T, A or S
             at residue #3"

(xi) SEQUENCE DESCRIPTION: SEQ ID NO: 90:

Trp Xaa Xaa Xaa Leu Lys Xaa Xaa Leu Xaa Cys
1               5                   10

(2) INFORMATION FOR SEQ ID NO: 91:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..9
         (D) OTHER INFORMATION: /label= SEQ91
             /note= "Xaa denotes V, L or I at residue #1"

(xi) SEQUENCE DESCRIPTION: SEQ ID NO: 91:
```

```
Xaa Pro Xaa Pro Arg Pro Gly Xaa Cys
1               5

(2) INFORMATION FOR SEQ ID NO: 92:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ92
            /note= "Xaa denotes K or Y at residue #2; F or Y
            at residue #4; F, Y or L at residue #5; F, Y, I or L at
            residue #6; and F or Y at residue #7"

(xi) SEQUENCE DESCRIPTION: SEQ ID NO: 92:

Asp Xaa Val Xaa Xaa Xaa Xaa
1               5

(2) INFORMATION FOR SEQ ID NO: 93:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..7
        (D) OTHER INFORMATION: /label= SEQ93
            /note= "Xaa denotes K or Y at residue #2; F or Y
            at residue #4; F, Y, I or L at residue #5; F, Y or I at
            residue #6; and F or Y at residue #7"

(xi) SEQUENCE DESCRIPTION: SEQ ID NO: 93:

Asp Xaa Val Xaa Xaa Xaa Xaa
1               5

(2) INFORMATION FOR SEQ ID NO: 94:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ94
            /note= "Xaa denotes V or I at residue #1; F, Y or L
            at residue #3; F, Y, I or L at residue #4; R or T at
            residue #6; and T or N at residue #8"

(xi) SEQUENCE DESCRIPTION: SEQ ID NO: 94:

Xaa Tyr Xaa Xaa Phe Xaa Xaa Xaa
1               5

(2) INFORMATION FOR SEQ ID NO: 95:
```

```
    (i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ95
            /note= "Xaa denotes V or I at residue #1; F, Y, I or L
            at residue #3; F, Y or I at residue #4; R or T at
            residue #6; and T or N at residue #8"

(xi) SEQUENCE DESCRIPTION: SEQ ID NO: 95:

Xaa Tyr Xaa Xaa Phe Xaa Xaa Xaa
1               5

(2) INFORMATION FOR SEQ ID NO: 96:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ96
            /note= "Xaa denotes V or I at residue #1; F, Y, I or L
            at residue #3; F, Y, I or L at residue #4; and T or N at
            residue #8"

(xi) SEQUENCE DESCRIPTION: SEQ ID NO: 96:

Xaa Tyr Xaa Xaa Phe Arg Xaa Xaa
1               5

(2) INFORMATION FOR SEQ ID NO: 97:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Peptide
        (B) LOCATION: 1..8
        (D) OTHER INFORMATION: /label= SEQ97
            /note= "Xaa denotes F or Y at residue #2; F, Y or L
            at residue #3; F, Y, I or L at residue #4; F or Y at
            residue #5; R or T at residue #6; E, D, or V at residue
            #7; and T or N at residue #8"

(xi) SEQUENCE DESCRIPTION: SEQ ID NO: 97:

Val Xaa Xaa Xaa Xaa Xaa Xaa Xaa
1               5

(2) INFORMATION FOR SEQ ID NO: 98:

(i) SEQUENCE CHARACTERISTICS:
        (A) LENGTH: 8 amino acids
        (B) TYPE: amino acid
        (C) STRANDEDNESS: single
        (D) TOPOLOGY: linear
```

```
    (ii) MOLECULE TYPE: peptide (ix) FEATURE:
         (A) NAME/KEY: Peptide
         (B) LOCATION: 1..8
         (D) OTHER INFORMATION: /label= SEQ98
             /note= "Xaa denotes F or Y at residue #2; F, Y, I or L
             at residue #3; F, Y or I at residue #4; F or Y at
             residue #5; R or T at residue #6; E, D, or V at residue
             #7; and T or N at residue #8"

(xi) SEQUENCE DESCRIPTION: SEQ ID NO: 98:

Val Xaa Xaa Xaa Xaa Xaa Xaa Xaa
1               5

(2) INFORMATION FOR SEQ ID NO: 99:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..8
         (D) OTHER INFORMATION: /label= SEQ99
             /note= "Xaa denotes F or Y at residue #2; F, Y, I or L
             at residue #3; F, Y, I or L at residue #4; F or Y at
             residue #5; E, D, or V at residue #7; and T or N at
             residue #8"

(xi) SEQUENCE DESCRIPTION: SEQ ID NO: 99:

Val Xaa Xaa Xaa Xaa Arg Xaa Xaa
1               5

(2) INFORMATION FOR SEQ ID NO: 100:

(i) SEQUENCE CHARACTERISTICS:
         (A) LENGTH: 8 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Peptide
         (B) LOCATION: 1..8
         (D) OTHER INFORMATION: /label= SEQ100
             /note= "Xaa denotes F or Y at residue #2; F, Y, I or L
             at residue #3; F, Y, I or L at residue #4; F or Y at
             residue #5; R or T at residue #6; E, D, or V at residue
             #7; and T or N at residue #8"

(xi) SEQUENCE DESCRIPTION: SEQ ID NO: 100:

Val Xaa Xaa Xaa Xaa Xaa Xaa Xaa
1               5
```